(12) United States Patent
Hu et al.

(10) Patent No.: US 8,354,548 B2
(45) Date of Patent: Jan. 15, 2013

(54) GLYCINE CHROMAN-6-SULFONAMIDES FOR USE AS INHIBITORS OF DIACYLGLYCEROL LIPASE

(75) Inventors: Shuanghua Hu, Milford, CT (US); Yazhong Huang, Branford, CT (US); Min Ding, Glastonbury, CT (US); Louis S. Chupak, Old Saybrook, CT (US); Xiaofan Zheng, Cheshire, CT (US); Robert G. Gentles, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 104 days.

(21) Appl. No.: 13/025,674

(22) Filed: Feb. 11, 2011

(65) Prior Publication Data

US 2011/0207772 A1    Aug. 25, 2011

Related U.S. Application Data

(60) Provisional application No. 61/306,023, filed on Feb. 19, 2010.

(51) Int. Cl.
*C07D 311/00* (2006.01)
(52) U.S. Cl. .................................................... 549/409
(58) Field of Classification Search ................... 549/409
See application file for complete search history.

(56) References Cited

OTHER PUBLICATIONS

U.S. Appl. No. 13/025,674, filed Feb. 11, 2011, Chupak et al.
Bisogno, T. et al., "Development of the first potent and specific inhibitors of endocannabinoid biosynthesis", Biochimica et Biophysica Acta, vol. 1761, pp. 205-212 (2006).
CAS Registry No. 1223584-09-5 (Feb. 15, 2011).

*Primary Examiner* — Nizal Chandrakumar
(74) *Attorney, Agent, or Firm* — Pamela A. Mingo; Gary D. Greenblatt

(57) ABSTRACT

The present disclosure is generally directed to compounds that can inhibit DAGLα and/or β activity, compositions comprising such compounds, and methods for inhibiting DAGLα and/or β activity.

12 Claims, No Drawings

GLYCINE CHROMAN-6-SULFONAMIDES FOR USE AS INHIBITORS OF DIACYLGLYCEROL LIPASE

CROSS-REFERENCE TO RELATED APPLICATIONS

This application claims the benefit of U.S. Provisional Application Ser. No. 61/306,023 filed Feb. 19, 2010.

The present disclosure is generally directed to compounds that can inhibit DAGLα and/or β activity, compositions comprising such compounds, and methods for inhibiting DAGLα and/or β activity.

Diacylglycerol Lipase enzymes are esterases that hydrolyze diacylglycerol to form the endogenous cannabinoid 2-arachidonyl glycerol (2-AG) (*J Cell Biol* 2003; 163:463-8). There are two isoforms of the enzyme, DAGLα and DAGLβ. DAGLα is predominantly expressed throughout the CNS with limited expression in the periphery, whereas DAGLβ is predominantly expressed in peripheral tissues (*J Cell Biol* 2003; 163:463-8) Immunohistochemical studies have demonstrated DAGLα is localized post-synaptically, consistent with its role in generating 2-AG which acts as a retrograde messenger activating presynaptic cannabinoid receptors including CB1 (*J Neurosci* 2007; 27(14):3663-3676, PLoS August 2007; 8:e709).

Consistent with the proposed role for DAGLα and DAGLβ as key enzymes in endocannabinoid synthesis, genetically-modified mice that lack DAGLα expression (BMS, Lexicon) exhibit decreased tissue concentrations of 2-AG. In addition, the DAGLα knockout animals exhibit multiple phenotypes in animal models relevant to human diseases. For example, in models predictive of activity in affective disorders, DAGLα−/− animals exhibit anxiolytic and antidepressant phenotypes. DAGLα−/− animals also are resistant to diet-induced obesity, have decreased food intake. These animals also exhibit decreased body weight, body fat, sensitivity to pain, and improved cognitive performance demonstrating broad therapeutic potential for the enzyme.

Based on these data and the role of DAGL enzymes in endocannaboid synthesis, compounds that inhibit DAGLα and/or β activity are predicted to have therapeutic utility in the treatment of schizophrenia, psychosis, bipolar disorder, depression, anxiety, pain, cognitive impairment, diabetes, obesity, hepatic steatosis, dyslipidemias, and other related disease states.

Currently, the only reported inhibitors of DAGL are chemically reactive molecules, that as such, can be expected to have limited utility due to lack of selectivity (*Bioorganic & Medicinal Chemistry Letters* (2008), 18(22), 5838-5841).

In a first aspect the present disclosure provides a compound of Formula (I)

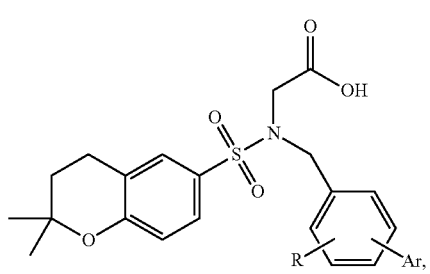

or a pharmaceutically acceptable salt thereof, wherein:

R is selected from hydrogen, cyano, halo, and $C_{1-6}$alkyl; and

Ar is selected from phenyl, naphthyl, or quinolinyl, wherein each are substituted with 0, 1, or 2 substituents selected from the group consisting of $C_{1-6}$alkyl, $C_{1-6}$alkoxy, trifluoromethyl, trifluoromethoxy, cyano, and halo.

In a first embodiment of the first aspect the present disclosure provides a compound of Formula (I), or a pharmaceutically acceptable salt thereof, wherein Ar is phenyl.

In a second embodiment of the first aspect the present disclosure provides a compound of Formula (I), or a pharmaceutically acceptable salt thereof, wherein Ar is phenyl and R is hydrogen.

In a third embodiment of the first aspect the present disclosure provides a compound of Formula (I), or a pharmaceutically acceptable salt thereof, wherein Ar is phenyl and R is selected from cyano, halo, and $C_1$ alkyl.

In a fourth embodiment of the first aspect the present disclosure provides a compound of Formula (I), or a pharmaceutically acceptable salt thereof, wherein Ar is naphthyl.

In a fifth embodiment of the first aspect the present disclosure provides a compound of Formula (I), or a pharmaceutically acceptable salt thereof, wherein Ar is naphthyl and R is hydrogen.

In a sixth embodiment of the first aspect the present disclosure provides a compound of Formula (I), or a pharmaceutically acceptable salt thereof, wherein Ar is naphthyl and R is selected from cyano, halo, and $C_1$ alkyl.

In a seventh embodiment of the first aspect the present disclosure provides a compound of Formula (I), or a pharmaceutically acceptable salt thereof, wherein Ar is quinolinyl.

In an eighth embodiment of the first aspect the present disclosure provides a compound of Formula (I), or a pharmaceutically acceptable salt thereof, wherein Ar is quinolinyl and R is hydrogen.

In a ninth embodiment of the first aspect the present disclosure provides a compound of Formula (I), or a pharmaceutically acceptable salt thereof, wherein Ar is quinolinyl and R is selected from cyano, halo, and $C_1$ alkyl.

In a second aspect the present disclosure provides a composition comprising a pharmaceutically acceptable amount of a compound of Formula (I), or a pharmaceutically acceptable salt thereof, and a pharmaceutically acceptable carrier.

In a third aspect the present disclosure provides a method for treating a disorder associated with DAGLα and/or DAGLβ activity, the method comprising administering to a patient in need thereof a therapeutically effective amount of a compound of Formula (I), or a pharmaceutically acceptable salt thereof. In a first embodiment of the third aspect the disorder is selected from schizophrenia, psychosis, bipolar disorder, depression, anxiety, pain, cognitive impairment, diabetes, obesity, hepatic steatosis, and dyslipidemia. In a second embodiment of the third aspect the disorder is selected from schizophrenia, bipolar disorder, depression, anxiety, diabetes, obesity, hepatic steatosis, and dyslipidemia.

Other embodiments of the present disclosure may comprise suitable combinations of two or more of embodiments and/or aspects disclosed herein.

Yet other embodiments and aspects of the disclosure will be apparent according to the description provided below.

The description of the present disclosure herein should be construed in congruity with the laws and principals of chemical bonding. In some instances it may be necessary to remove a hydrogen atom in order accommodate a substituent at any given location.

It should be understood that the compounds encompassed by the present disclosure are those that are suitably stable for use as pharmaceutical agent.

All patents, patent applications, and literature references cited in the specification are herein incorporated by reference in their entirety. In the case of inconsistencies, the present disclosure, including definitions, will prevail.

As used in the present specification, the following terms have the meanings indicated:

As used herein, the singular forms "a", "an", and "the" include plural reference unless the context clearly dictates otherwise.

In some instances, the number of carbon atoms in any particular group is denoted before the recitation of the group. For example, the term "$C_{2-6}$ alkenyl" denotes an alkenyl group containing two to six carbon atoms. Where these designations exist they supercede all other definitions contained herein.

The term "alkoxy," as used herein, refers to an alkyl group attached to the parent molecular moiety through an oxygen atom.

The term "alkyl," as used herein, refers to a group derived from a straight or branched chain saturated hydrocarbon containing from one to six carbon atoms.

The term "cyano," as used herein, refers to —CN.

The terms "halo" and "halogen," as used herein, refer to F, Cl, Br, or I.

Asymmetric centers may exist in the compounds of the present disclosure. These centers are designated by the symbols "R" or "S", depending on the configuration of substituents around the chiral carbon atom. It should be understood that the disclosure encompasses all stereochemical isomeric forms, or mixtures thereof, which possess the ability to inhibit DAGL. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The term "compounds of the present disclosure", and equivalent expressions, are meant to embrace compounds of Formula (I), and pharmaceutically acceptable enantiomers, diastereomers, and salts thereof. Similarly, references to intermediates are meant to embrace their salts where the context so permits.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, dihydrobromide, diydrochloride, dihydroiodide, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

When it is possible that, for use in therapy, therapeutically effective amounts of a compound of Formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of Formula (I) or pharmaceutically acceptable salts thereof, and one or more pharmaceutically acceptable carriers, diluents, or excipients. The term "therapeutically effective amount," as used herein, refers to the total amount of each active component that is sufficient to show a meaningful patient benefit. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of Formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing a compound of Formula (I), or a pharmaceutically acceptable salt thereof, with one or more pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Treatment may be initiated with small dosages substantially less than the optimum dose of the compound. Thereafter, the dosage is increased by small increments until the optimum effect under the circumstances is reached. In general, the compound is most desirably administered at a concentration level that will generally afford effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of Formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of Formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research* 1986, 3(6), 318.

Pharmaceutical formulations adapted for topical administration may be formulated as ointments, creams, suspensions, lotions, powders, solutions, pastes, gels, sprays, aerosols, or oils.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

This disclosure is intended to encompass compounds having Formula (I) when prepared by synthetic processes or by metabolic processes including those occurring in the human or animal body (in vivo) or processes occurring in vitro.

The abbreviations used in the present application, including particularly in the illustrative schemes and examples which follow, are well-known to those skilled in the art. Some of the abbreviations used are as follows: DMAP for N,N-dimethylaminopyridine; BEMP for 2-tert-butylimino-2-diethylamino-1,3-dimethylperhydro-1,3,2-diazaphosphorine; TFA for trifluoroacetic acid; DCM for dichloromethane; rt or RT or Rt for retention time or room temperature (context will dictate); DMSO for dimethylsulfoxide; EtOAc for ethyl acetate; MeCN or ACN for acetonitrile; $PPh_3$ for triphenylphosphine; and DMF for N,N-dimethylformamide.

EXAMPLES

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

The compounds of the present disclosure may be prepared using the reactions and techniques described in this section as well as other synthetic methods known to those of ordinary skill in the art. The reactions are performed in solvents appropriate to the reagents and materials employed and suitable for the transformation being effected. Also, in the description of the synthetic methods described below, it is to be understood that all proposed reaction conditions, including choice of solvents, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

The compounds of the invention can be made according to methods known in the art including those illustrated in Scheme 1 below. Intermediates A can be formed by sulfonylation of tert-butyl 2-aminoacetate in the presence of base and a catalytic amount of dimethylaminopyridine (DMAP) at room temperature. Alkylation of intermediates A with aryl methyl bromides in the presence of a base such as resin-supported 2-tert-butylimino-2-diethylamino-1,3-dimethylperhydro-1,3,2-diazaphosphorine (BEMP), at 90° C. can form intermediate esters B. Compounds C of the invention can be formed via de-protection of compounds B with, for example, TFA.

Additional methodology that can provide examples of this invention is depicted in Scheme 2. Bromo intermediates D can be obtained from intermediate A by alkylation with bromoaryl methyl bromides in the presence of a base such as resin-supported (BEMP) at 90° C. Intermediates D can then be coupled with a variety of boronic acids to provide intermediates E, using for example, Suzuki coupling conditions. The desired compounds F can be obtained by treatment of the Suzuki coupling products, with, for example, TFA in dichloromethane (DCM) at room temperature.

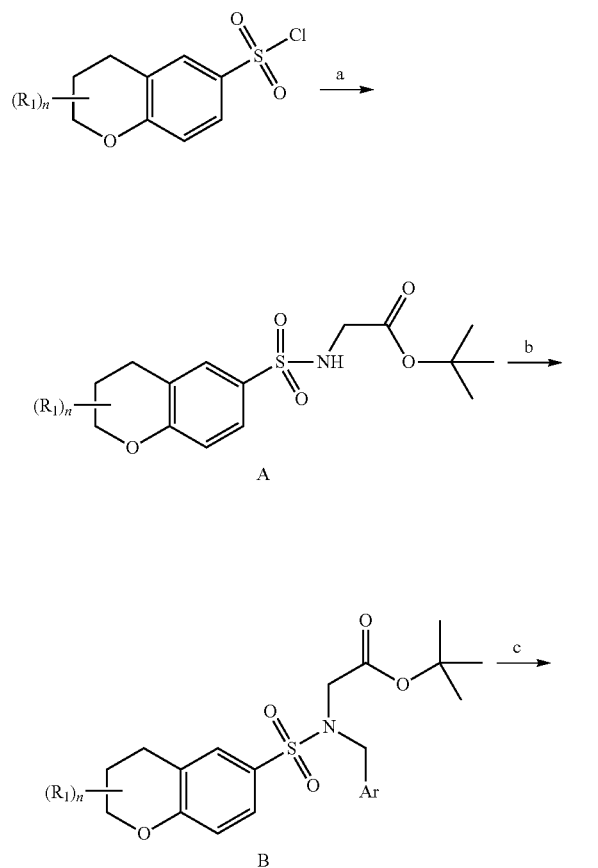

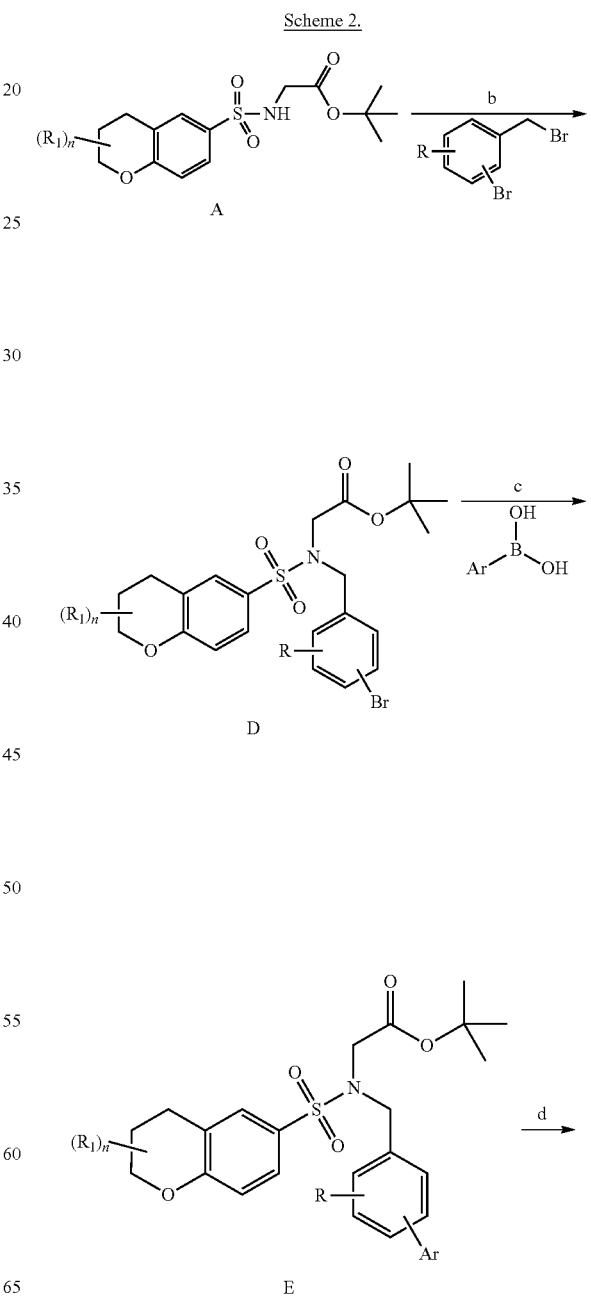

Reagents and conditions: a) tert-butyl 2-aminoacetate, Hunig's base, cat. DMAP, DCM, -30° C. to rt; b) Arylmethyl bromide, BEMP-resin, acetonitrile, 90° C.; c) TFA, DCM, rt.

-continued

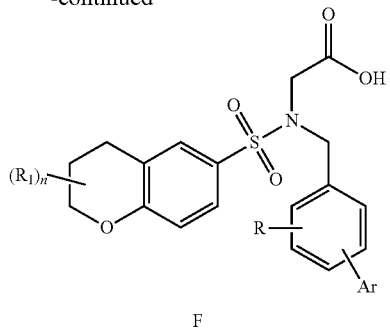

Reagents and conditions: a) tert-butyl 2-aminoacetate, Hunig's base, cat. DMAP, DCM, -30° C. to rt; b) bromoarylmethyl bromide, BEMP-resin, acetonitrile, microwave heat, 90° C.; c) TFA, DCM, rt.

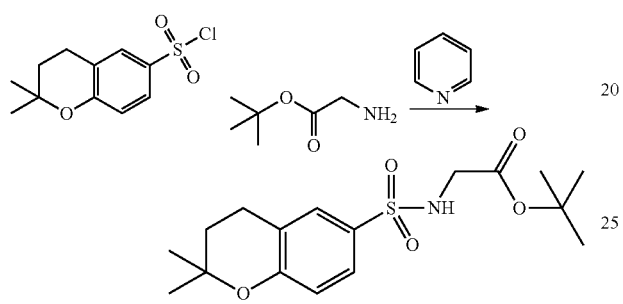

Intermediate A

Tert-butyl 2-(2,2-dimethylchroman-6-sulfonamido)acetate

To the solution of 2,2-dimethylchroman-6-sulfonyl chloride (3.165 g, 10.92 mmol) in DCM (50 mL) at −30° C. was added tert-butyl 2-aminoacetate (2.308 mL, 16.39 mmol), Hunig'sBase (3.82 mL, 21.85 mmol), and catalytic amount of DMAP. The mixture was stirred at 25° C. overnight while the reddish orange color of the reaction mixture turned bright yellow. The crude reaction mixture was diluted with EtOAc, washed with dilute aqueous hydrochloric acid solution, then aqueous NaHCO3 solution and brine. The organic layer was dried over MgSO4 and removed on a rotavapor to give a creamy powder. The crude material was purified by silica chromatography (15-30% EtOAc/Hexanes) to yield 3.6 grams of an off white powder (88%). $^1$H NMR (500 MHz, CDCl3) δ 7.58 (d, J=2.1 Hz, 1H), 7.55 (dd, J=8.6, 2.3 Hz, 1H), 6.81 (t, J=10.6 Hz, 1H), 4.90 (s, 1H), 3.64 (d, J=5.1 Hz, 2H), 2.81 (t, J=6.7 Hz, 2H), 1.81 (t, J=6.7 Hz, 2H), 1.35 (s, 9H), 1.34 (s, 6H). LRMS [ESI, (M−H)$^-$] m/z calcd for C17H24NO5S 354.14, found 354.2.

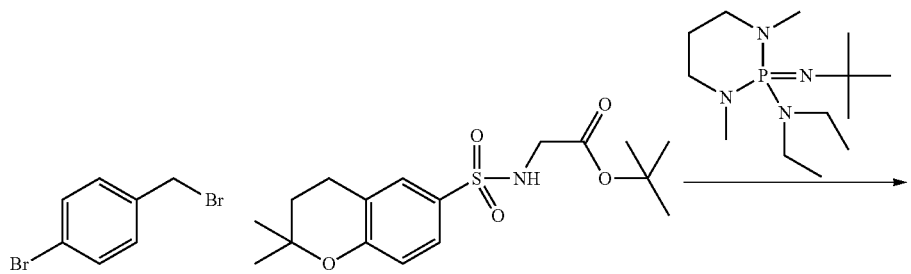

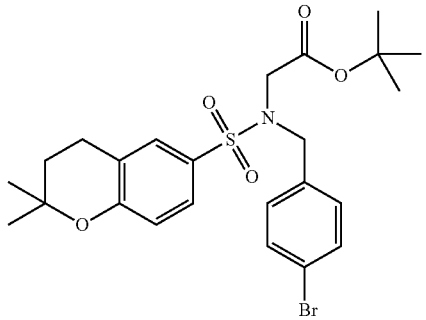

Intermediate B tert-butyl 2-(N-(4-bromobenzyl)-2,2-dimethylchroman-6-sulfonamido)acetate

To a solution of tert-butyl 2-(2,2-dimethylchroman-6-sulfonamido)acetate (500 mg, 1.407 mmol) in MeCN (15 mL) was added resin-supported BEMP (786 mg, 1.547 mmol) and 1-bromo-4-(bromomethyl)benzene (602 mg, 2.409 mmol). The mixture was heated in a microwave synthesizer at 90° C. for 3 hours. The reaction mixture was filtered, rinsed alternatively by dichloromethane and methanol. The filtrate was concentrated to give a reddish orange residue, which was purified by silica chromatography to obtain a white powder (632 mg, 86% yield). $^1$H NMR (500 MHz, CDCl3) δ 7.59-7.55 (m, 2H), 7.43 (d, J=8.3 Hz, 2H), 7.14 (d, J=8.3 Hz, 2H), 6.84 (d, J=9.1 Hz, 1H), 4.45 (s, 2H), 3.78 (s, 2H), 2.79 (t, J=6.7 Hz, 2H), 1.83 (t, J=6.7 Hz, 2H), 1.35 (s, 6H), 1.33 (s, 9H). LRMS [ESI, MH$^+$] m/z calcd for C24H31BrNO5S 524.11, found 524.1.

Intermediate C tert-butyl 2-(N-(3-bromobenzyl)-2,2-dimethylchroman-6-sulfonamido)acetate

To the solution of tert-butyl 2-(2,2-dimethylchroman-6-sulfonamido)acetate (500 mg, 1.407 mmol) in MeCN (15 mL) was added resin-supported BEMP (786 mg, 1.547 mmol) and 1-bromo-3-(bromomethyl)benzene (598 mg, 2.391 mmol). The mixture was heated in a microwave synthesizer at 90° C. for 3 hours. The reaction mixture was filtered, rinsed alternatively with dichloromethane and methanol. The filtrate was concentrated to give a reddish orange residue, which was purified by silica chromatography to obtain a white powder (620 mg, 84% yield). $^1$H NMR (500 MHz, CDCl3) δ 7.60-7.54 (m, 2H), 7.40 (d, J=7.4 Hz, 1H), 7.35 (s, 1H), 7.19 (dt, J=15.1, 7.6 Hz, 2H), 6.88-6.81 (m, 1H), 4.47 (s, 2H), 3.80 (s, 2H), 2.80 (t, J=6.7 Hz, 2H), 1.83 (t, J=6.7 Hz, 2H), 1.35 (s, 6H), 1.35 (s, 9H). LRMS [ESI, MH$^+$] m/z calcd for C24H31BrNO5S 524.11, found 524.1.

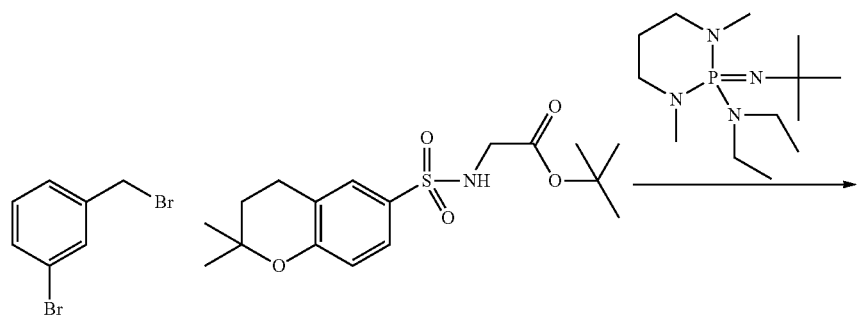

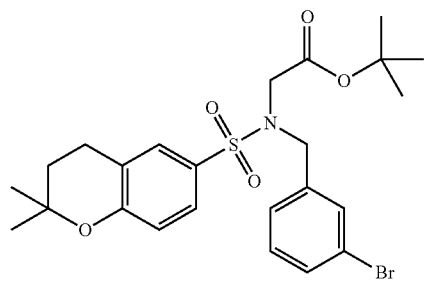

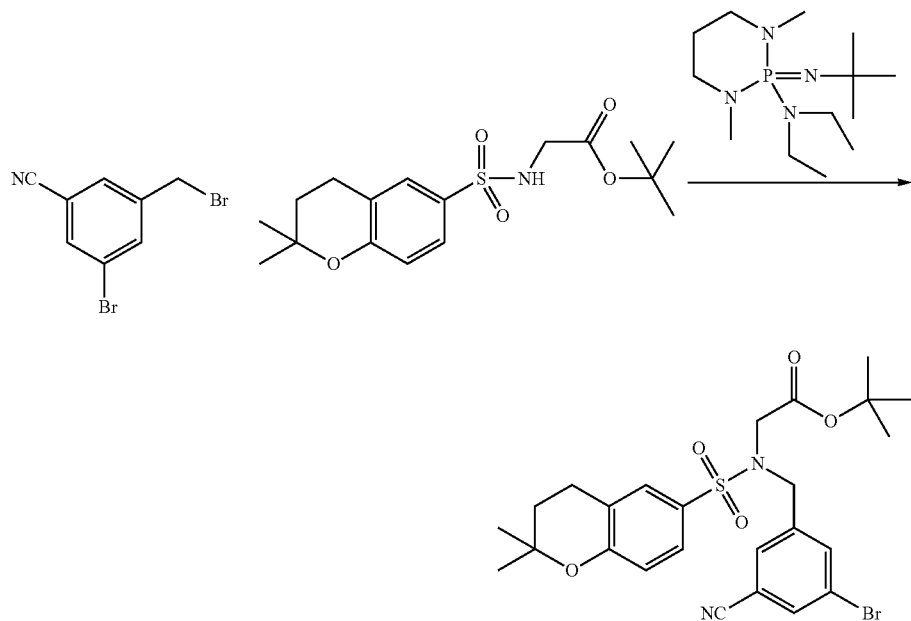

Intermediate D tert-butyl 2-(N-(3-bromo-5-cyanobenzyl)-2,2-dimethylchroman-6-sulfonamido)acetate To the solution of tert-butyl 2-(2,2-dimethylchroman-6-sulfonamido)acetate (500 mg, 1.407 mmol) in MeCN (15 mL) was added resin-supported BEMP (786 mg, 1.547 mmol) and 3-bromo-5-(bromomethyl)benzonitrile (503 mg, 1.829 mmol). The mixture was heated in a microwave synthesizer at 90° C. for 3 hours. The reaction mixture was filtered, rinsed alternatively with dichloromethane and methanol. The filtrate was concentrated to give a reddish orange residue, which was purified by silica chromatography to obtain a white powder (616 mg, 80% yield). $^1$H NMR (500 MHz, CDCl3) δ 7.69 (d, J=8.6 Hz, 2H), 7.57-7.52 (m, 2H), 7.49 (s, 1H), 6.85 (d, J=9.3 Hz, 1H), 4.49 (s, 2H), 3.82 (s, 2H), 2.81 (t, J=6.7 Hz, 2H), 1.84 (t, J=6.7 Hz, 2H), 1.36 (s, 9H), 1.36 (s, 6H). LRMS [ESI, MH$^+$] m/z calcd for C25H30BrN2O5S 549.11, found 549.1.

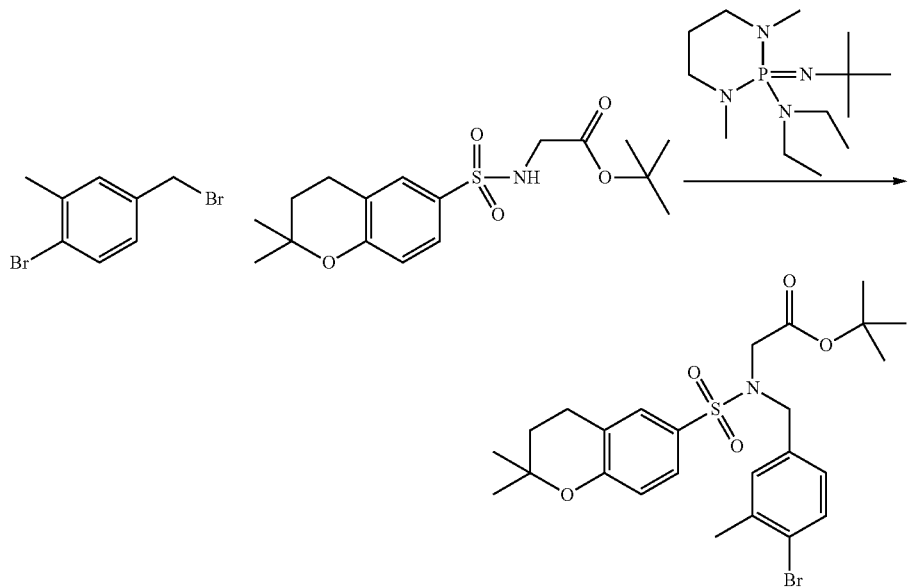

Intermediate E tert-butyl 2-(N-(4-bromo-3-methylbenzyl)-2,2-dimethylchroman-6-sulfonamido)acetate To the solution of tert-butyl 2-(2,2-dimethylchroman-6-sulfonamido)acetate (500 mg, 1.407 mmol) in MeCN (15 mL) was added resin-supported BEMP (786 mg, 1.547 mmol) and 1-bromo-4-(bromomethyl)-2-methylbenzene (631 mg, 2.391 mmol). The mixture was heated in a microwave synthesizer at 90° C. for 3 hours. The reaction mixture was filtered, rinsed alternatively by dichloromethane and methanol. The filtrate was concentrated to give a reddish orange residue, which was purified by silica chromatography to obtain a white powder (516 mg, 68% yield). $^1$H NMR (500 MHz, CDCl3) δ 7.58 (d, J=2.2 Hz, 1H), 7.57 (s, 1H), 7.44 (d, J=8.1 Hz, 1H), 7.09 (s, 1H), 6.92 (dd, J=8.2, 2.1 Hz, 1H), 6.84 (d, J=9.3 Hz, 1H), 4.42 (s, 2H), 3.78 (s, 2H), 2.79 (t, J=6.8 Hz, 2H), 2.34 (s, 3H), 1.82 (t, J=6.7 Hz, 2H LRMS [ESI, MH$^+$] m/z calcd for C25H33BrNO5S 538.13, found 538.1.

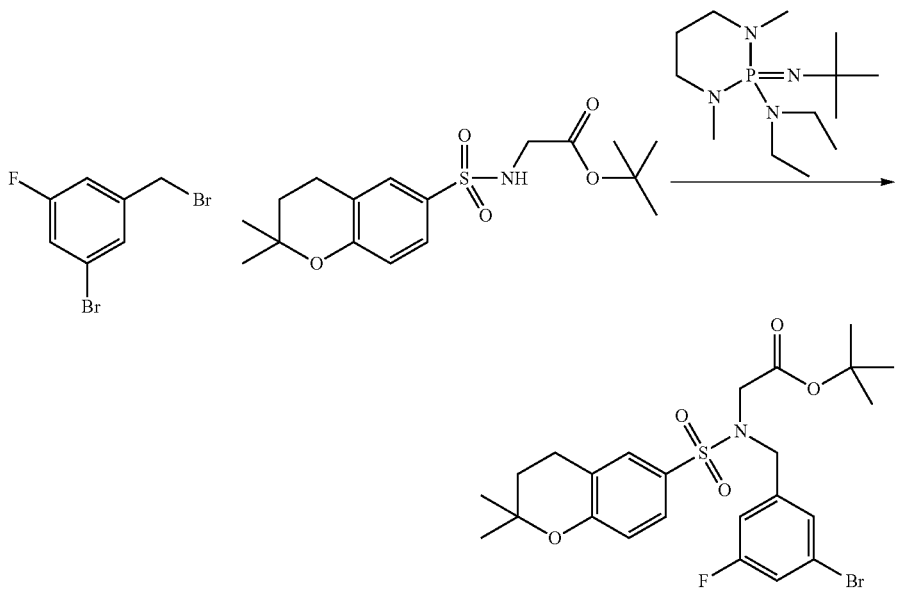

Intermediate F tert-butyl 2-(N-(3-bromo-5-fluorobenzyl)-2,2-dimethylchroman-6-sulfonamido)acetate To the solution of tert-butyl 2-(2,2-dimethylchroman-6-sulfonamido)acetate (500 mg, 1.407 mmol) in MeCN (15 mL) was added resin-supported BEMP (786 mg, 1.547 mmol) and 1-bromo-3-(bromomethyl)-5-fluorobenzene (501 mg, 1.871 mmol). The mixture was heated in a microwave synthesizer at 90° C. for 3 hours. The reaction mixture was filtered, rinsed alternatively by dichloromethane and methanol. The filtrate was concentrated to give a reddish orange residue, which was purified by silica chromatography to obtain a white powder (688 mg, 86% yield). $^1$H NMR (500 MHz, CDCl3) δ 7.56 (d, J=6.2 Hz, 2H), 7.18-7.12 (m, 2H), 6.95 (d, J=9.0 Hz, 1H), 6.87-6.80 (m, 1H), 4.46 (s, 2H), 3.82 (s, 2H), 2.80 (t, J=6.7 Hz, 2H), 1.83 (t, J=6.7 Hz, 2H), 1.36 (s, 9H), 1.35 (s, 6H). $^{19}$F NMR (471 MHz, CDCl3) δ LRMS [ESI, MH$^+$] m/z calcd for C24H30BrFNO5S 542.10, found 542.1.

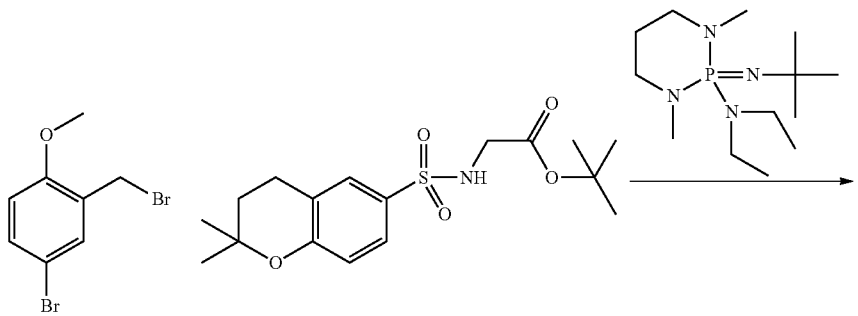

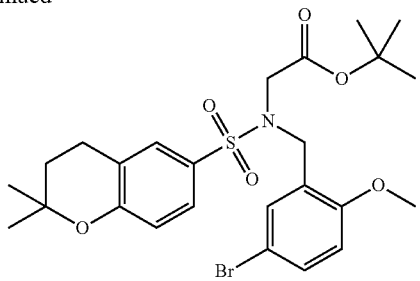

Intermediate G tert-butyl 2-(N-(5-bromo-2-methoxybenzyl)-2,2-dimethylchroman-6-sulfonamido)acetate To the solution of tert-butyl 2-(2,2-dimethylchroman-6-sulfonamido)acetate (500 mg, 1.407 mmol) in MeCN (15 mL) was added resin-supported BEMP (786 mg, 1.547 mmol) and 4-bromo-2-(bromomethyl)-1-methoxybenzene (500 mg, 1.786 mmol). The mixture was heated in a microwave synthesizer at 90° C. for 3 hours. The reaction mixture was filtered, rinsed alternatively by dichloromethane and methanol. The filtrate was concentrated to give a reddish orange residue, which was purified by silica chromatography to obtain a white powder (700 mg, 85% yield). $^1$H NMR (500 MHz, CDCl3) δ 7.56-7.50 (m, 2H), 7.34-7.29 (m, 2H), 6.81 (d, J=8.1 Hz, 1H), 6.66 (d, J=8.5 Hz, 1H), 4.47 (s, 2H), 3.88 (s, 2H), 3.71 (s, 3H), 2.78 (t, J=6.7 Hz, 2H), 1.82 (t, J=6.7 Hz, 2H), 1.38 (s, 9H), 1.34 (s, 6H). LRMS [ESI, MH$^-$] m/z calcd for C25H33BrNO6S 554.12, found 554.1.

EXAMPLES to obtain tert-butyl 2-(N-(biphenyl-3-ylmethyl)-2,2-dimethylchroman-6-sulfonamido)acetate as an oil (26 mg, 84% yield). $^1$H NMR (500 MHz, CDCl3) δ 7.64-7.60 (m, 2H), 7.54-7.49 (m, 3H), 7.44-7.40 (m, 3H), 7.38 (dd, J=9.4, 5.8 Hz, 1H), 7.33 (ddd, J=6.7, 4.0, 1.2 Hz, 1H), 7.22 (d, J=7.7 Hz, 1H), 4.57 (s, 2H), 3.84 (s, 2H), 2.78 (t, J=6.7 Hz, 2H), 1.80 (t, J=6.7LRMS [ESI, MNa$^+$] m/z calcd for C30H35NO5SNa 544.21. found 544.32. To the solution of tert-butyl 2-(N-(biphenyl-3-ylmethyl)-2,2-dimethylchroman-6-sulfonamido)acetate (23 mg, 0.044 mmol) in DCM (1 mL) was added trifluoroacetic acid (0.102 mL, 1.323 mmol). The mixture was stirred at RT for 1 hour. The reaction mixture was concentrated to give a reddish residue, which was purified by preparative HPLC using MeCN—H2O-0.1% TFA as the solvent to obtain the product as a white powder (17 mg, 82% yield). $^1$H NMR (500 MHz, CDCl3) δ 7.61 (d, J=6.3 Hz, 1H), 7.60 (s, 1H), 7.51 (d, 1H), 7.50 (d, J=7.4 Hz, 2H), 7.41 (dd, J=13.4, 5.5 Hz, 2H), 7.39 (s, 1H), 7.36 (d, J=7.7 Hz, 1H), 7.34 (t, J=7.3 Hz, 1H), 7.19 (d, J=7.6 Hz, 1H), 6.87-6.83 (m, 1H), 4.52 (s, 2H), 3.97 (s, 2H), 2.77 (t, J=6.7 Hz, 2H), 1.79 (t, J=6.7 Hz, 2H), 1.33 (s, 6H). LRMS [ESI, (M-H)$^-$] m/z calcd for C26H26NO5S 464.15, found 464.32.

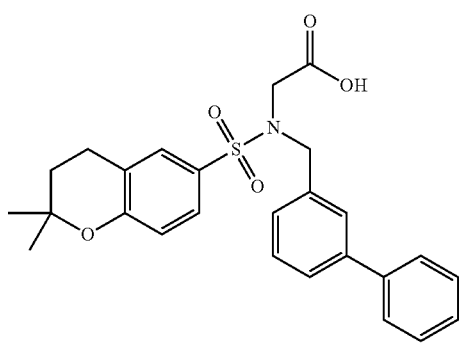 [SMILES: CC1(C)CCc2cc(S(=O)(=O)N(CC(=O)O)Cc3cccc(-c4ccccc4)c3)ccc2O1]

Example 1

2-(N-(biphenyl-3-ylmethyl)-2,2-dimethylchroman-6-sulfonamido)acetic acid

To a solution of tert-butyl 2-(2,2-dimethylchroman-6-sulfonamido)acetate (20 mg, 0.056 mmol) in acetonitrile (1 mL) was added 3-(bromomethyl)biphenyl (19.47 mg, 0.079 mmol) and resin-supportedBEMP (42.9 mg, 0.084 mmol). The mixture was heated in an oil bath at 90° C. overnight. The reaction mixture was filtered, and the filtrate was concentrated to give an orange residue, which was purified by preparative HPLC using MeCN—H2O-0.1% TFA as the solvent

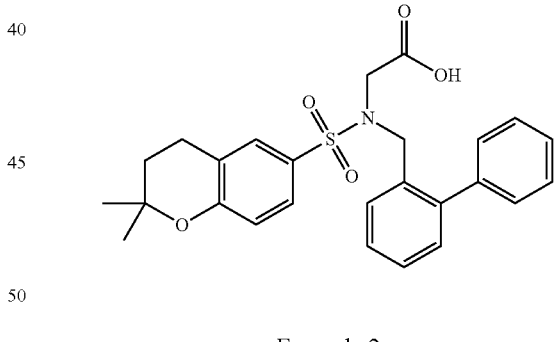

Example 2

2-(N-(biphenyl-2-ylmethyl)-2,2-dimethylchroman-6-sulfonamido)acetic acid

To a Wheaton vial containing 3-(bromomethyl)biphenyl (22.2 mg, 0.090 mmol) and resin-supported BEMP (52 mg, 0.095 mmol) was added a solution of tert-butyl 2-(2,2-dimethylchroman-6-sulfonamido)acetate (18 mg, 0.05 mmol) in acetonitrile (1 mL). The mixture was heated to 90° C. and shaken vigorously for two days. The reaction mixture was filtered, and the filtrate was concentrated. The crude product was taken in dichloromethane (0.5 mL) and trifluoroacetic acid (0.5 mL) was added. The mixture was shaken for 4 hours at room temperature. It was concentrated and the residue was purified by prep HPLC to obtain the product (15.3 mg, 66% yield in two steps). $^1$H NMR (600 MHz, DMSO/CDCl3) δ 7.52-7.46 (m, 1H), 7.46-7.41 (m, 2H), 7.41-7.33 (m, 5H), 7.23 (d, J=7.4 Hz, 2H), 7.19-7.14 (m, 1H), 6.77 (d, J=9.1 Hz, 1H), 4.40 (s, 2H), 3.63 (s, 2H), 2.75 (t, J=6.4 Hz, 2H), 1.82 (t, J=6.5 Hz, 2H), 1.34 (s, 6H). LRMS [ESI, MH$^+$] m/z calcd for C26H28NO5S 466.17, found 466.22.

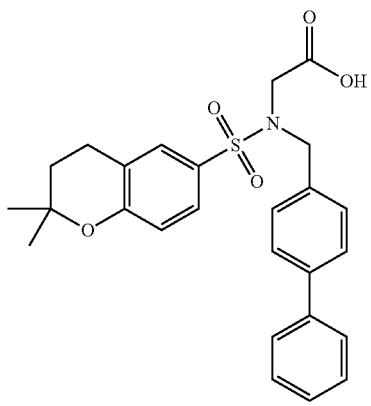 [SMILES: CC1(C)CCc2cc(S(=O)(=O)N(CC(=O)O)Cc3ccc(-c4ccccc4)cc3)ccc2O1]

Example 3

2-(N-(biphenyl-4-ylmethyl)-2,2-dimethylchroman-6-sulfonamido)acetic acid

To a solution of tert-butyl 2-(2,2-dimethylchroman-6-sulfonamido)acetate (40 mg, 0.113 mmol) in acetonitrile (2 mL) was added 3-(bromomethyl)biphenyl (38.9 mg, 0.158 mmol) and resin-supported BEMP (74.5 mg, 0.164 mmol). The mixture was heated in an oil bath at 90° C. overnight. The reaction mixture was filtered, and the filtrate was concentrated to dryness. The crude mixture was taken in DCM (2 mL) and trifluoroacetic acid was added (1 mL). The mixture was stirred at RT for 1 hr and was concentrated to give a off white residue, which was purified by preparative HPLC using MeCN—H2O-0.1% TFA as the solvent to obtain the product as a white powder (25 mg, 45% in two steps). $^1$H NMR (400 MHz, CDCl3) δ 7.66-7.61 (m, 2H), 7.60 (d, J=1.4 Hz, 1H), 7.59-7.56 (m, 2H), 7.55 (d, J=1.7 Hz, 1H), 7.49-7.43 (m, 2H), 7.40-7.35 (m, 1H), 7.32 (d, J=8.2 Hz, 2H), 6.89 (dd, J=8.5, 7.2 Hz, 1H), 4.52 (s, 2H), 3.99 (s, 2H), 2.83 (t, J=6.7 Hz, 2H), 1.86 (t, J=6.7 Hz, 2H), 1.38 (s, 6H). LRMS [ESI, MH$^+$] m/z calcd for C26H28NO5S 466.17. found 466.1.

The following examples were prepared according to the methodology depicted in the above scheme using the following conditions.

General Suzuki Coupling Procedure:

To reaction vials containing separately various aryl boronic acids (0.210 mmol) was added aqueous K$_3$PO$_4$ solution (2M, 0.140 mL, 0.280 mmol) and a common DMF stock solution of the starting material—substituted tert-butyl 2-(N-(bromobenzyl)-2,2-dimethylchroman-6-sulfonamido)acetates (Intermediates B-G) (1.5 mL each, 0.070 mmol). Pd(Ph$_3$P)$_4$ powder (about 8.09 mg, 7.00 µmol) was added into each tube, and the tubes were caped immediately before they were placed in oil bath (100~105° C.) and stirred overnight. Each crude reaction mixture was filtered by 0.45 um PVDF to give a clear sample, which was purified by preparative HPLC (CH$_3$CN—H$_2$O-0.1% TFA as the eluent) to yield white or pale yellow products. Each purified coupling product was then dissolved in dichloromethane (2 mL) and TFA (1 mL) was added. The solution was stirred at room temperature for 1 hour, and TFA and solvent was removed under vacuo to dryness. The residues were taken in DMF and filtered by 0.45 um PVDF to give clear solutions, which were purified by preparative HPLC (CH$_3$CN—H$_2$O-0.1% TFA as the eluent) to obtain the desired products.

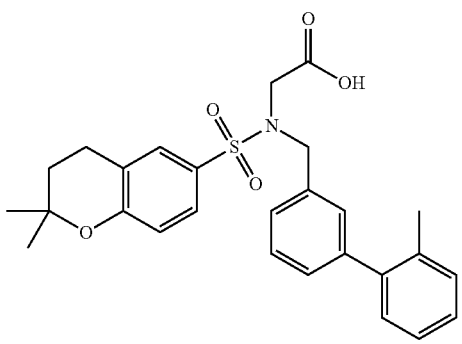

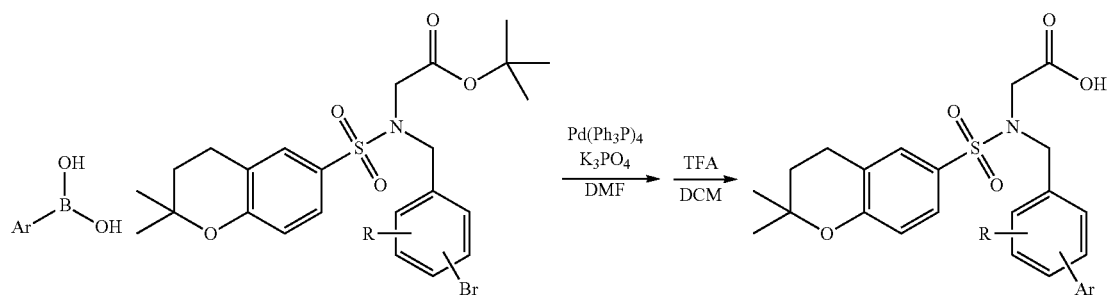

Example 4

2-(2,2-dimethyl-N-((2'-methylbiphenyl-3-yl)methyl) chroman-6-sulfonamido)acetic acid ¹H NMR (500 MHz, CDCl3) δ 7.61-7.56 (m, 2H), 7.34 (t, J=7.6 Hz, 1H), 7.27-7.22 (m, 3H), 7.22-7.16 (m, 2H), 7.14 (d, J=1.7 Hz, 2H), 6.81 (t, J=9.7 Hz, 1H), 4.49 (s, 2H), 3.97 (s, 2H), 2.76 (t, J=6.7 Hz, 2H), 2.20 (s, 3H), 1.79 (t, J=6.7 Hz, 2H), 1.33 (s, 6H). LRMS [ESI, MH⁺] m/z calcd for C27H30NO5S 480.18, found 480.2.

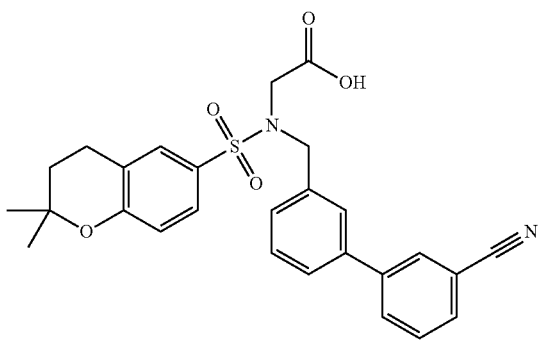 [SMILES: CC1(C)CCc2cc(S(=O)(=O)N(CC(=O)O)Cc3cccc(-c4cccc(C#N)c4)c3)ccc2O1]

Example 5

2-(N-((3'-cyanobiphenyl-3-yl)methyl)-2,2-dimethyl-chroman-6-sulfonamido)acetic acid ¹H NMR (500 MHz, CDCl3) δ 7.78 (d, J=1.6 Hz, 1H), 7.75-7.70 (m, 1H), 7.62 (dt, J=7.7, 1.2 Hz, 1H), 7.59 (dd, J=6.5, 2.4 Hz, 2H), 7.53 (t, J=7.8 Hz, 1H), 7.47 (d, J=7.9 Hz, 1H), 7.41 (dd, J=8.5, 6.7 Hz, 2H), 7.29-7.26 (m, 1H), 6.87-6.83 (m, 1H), 4.51 (s, 2H), 3.96 (s, 2H), 2.78 (t, J=6.7 Hz, 2H), 1.80 (t, J=6.7 Hz, 2H), 1.33 (s, 6H). LRMS [ESI, MH⁺] m/z calcd for C27H27N2O5S 491.16, found 491.2.

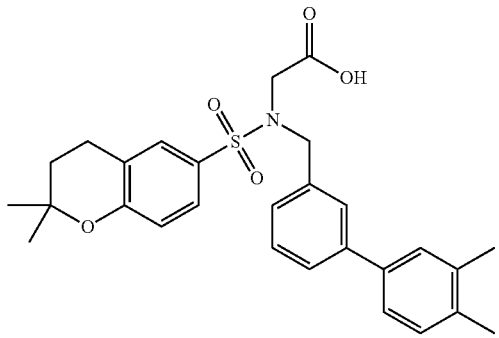

Example 6

2-(N-((3',4'-dimethylbiphenyl-3-yl)methyl)-2,2-dimethylchroman-6-sulfonamido)acetic acid ¹H NMR (500 MHz, CDCl3) δ 7.62-7.58 (m, 2H), 7.49 (d, J=7.8 Hz, 1H), 7.37-7.32 (m, 2H), 7.28 (s, 1H), 7.23 (dd, J=7.8, 1.8 Hz, 1H), 7.19-7.13 (m, 2H), 6.85 (d, J=8.3 Hz, 1H), 4.51 (s, 2H), 3.96 (s, 2H), 2.76 (t, J=6.7 Hz, 2H), 2.31 (s, 3H), 2.29 (s, 3H), 1.78 (t, J=6.7 Hz, 2H), 1.32 (s, 6H). LRMS [ESI, MH⁺] m/z calcd for C28H32NO5S 494.2, found 494.3.

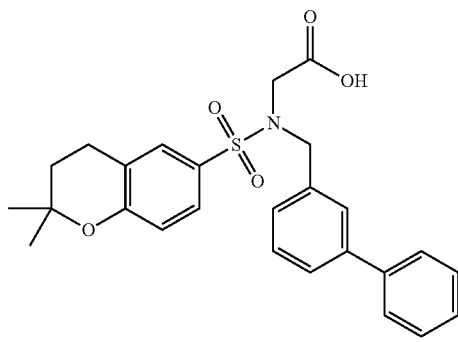

Example 7

2-(N-((3'-methoxybiphenyl-3-yl)methyl)-2,2-dimethylchroman-6-sulfonamido)acetic acid ¹H NMR (500 MHz, CDCl3) δ 7.62-7.58 (m, 2H), 7.50 (d, J=7.8 Hz, 1H), 7.39 (s, 1H), 7.36 (t, J=7.7 Hz, 1H), 7.33 (t, J=7.9 Hz, 1H), 7.20 (d, J=7.6 Hz, 1H), 7.08 (d, J=7.9 Hz, 1H), 7.06-7.03 (m, 1H), 6.88 (dd, J=8.2, 2.4 Hz, 1H), 6.86-6.82 (m, 1H), 4.51 (s, 2H), 3.96 (s, 2H), 3.85 (s, 3H), 2.76 (t, J=6.7 Hz, 2H), 1.79 (t, J=6.7 Hz, 2H), 1.32 (s, 6H). LRMS [ESI, MH⁺] m/z calcd for C27H30NO6S 496.18, found 496.2.

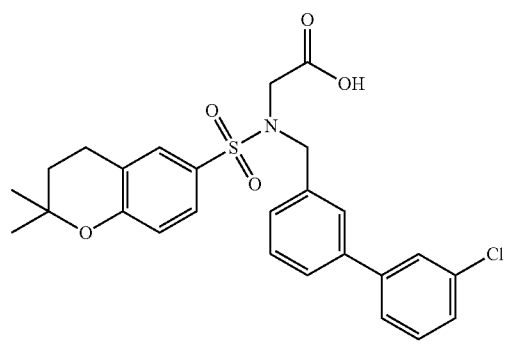 [SMILES: CC1(C)CCc2cc(S(=O)(=O)N(CC(=O)O)Cc3cccc(-c4cccc(Cl)c4)c3)ccc2O1]

Example 8

2-(N-((3'-chlorobiphenyl-3-yl)methyl)-2,2-dimethyl-chroman-6-sulfonamido)acetic acid ¹H NMR (500 MHz, CDCl3) δ 7.62-7.57 (m, 2H), 7.49-7.45 (m, 2H), 7.38 (d, J=7.7 Hz, 1H), 7.35 (dd, J=12.3, 4.7 Hz, 3H), 7.31 (dt, J=7.4, 1.8 Hz, 1H), 7.22 (d, J=7.6 Hz, 1H), 6.87-6.83 (m, 1H), 4.51 (s, 2H), 3.96 (s, 2H), 2.77 (t, J=6.7 Hz, 2H), 1.79 (t, J=6.7 Hz, 2H), 1.32 (s, 6H). LRMS [ESI, MH⁺] m/z calcd for C26H27ClNO5S 500.13, found 500.13.

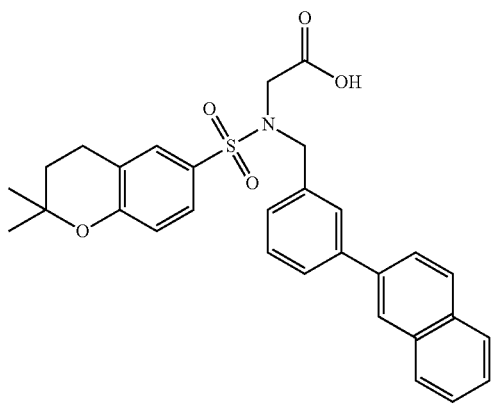 [SMILES: CC1(C)CCc2cc(S(=O)(=O)N(CC(=O)O)Cc3cccc(-c4ccc5ccccc5c4)c3)ccc2O1]

Example 9

2-(2,2-dimethyl-N-(3-(naphthalen-2-yl)benzyl)chroman-6-sulfonamido)acetic acid $^1$H NMR (500 MHz, CDCl3) δ 7.94 (d, J=1.1 Hz, 1H), 7.89 (d, J=8.6 Hz, 2H), 7.87-7.82 (m, 1H), 7.65-7.59 (m, 4H), 7.49 (pd, J=6.9, 3.5 Hz, 3H), 7.41 (t, J=7.7 Hz, 1H), 7.21 (d, J=7.6 Hz, 1H), 6.86 (d, J=8.4 Hz, 1H), 4.55 (s, 2H), 3.99 (s, 2H), 2.74 (t, J=6.7 Hz, 2H), 1.74 (t, J=6.7 Hz, 2H), 1.29 (s, 6H). LRMS [ESI, MH$^-$] m/z calcd for C30H30NO5S 516.18, found 516.2.

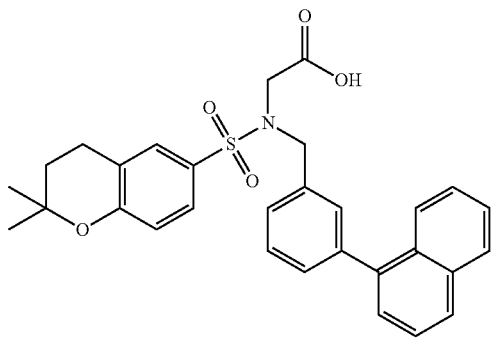 [SMILES: CC1(C)CCc2cc(S(=O)(=O)N(CC(=O)O)Cc3cccc(-c4cccc5ccccc45)c3)ccc2O1]

Example 10

2-(2,2-dimethyl-N-(3-(naphthalen-1-yl)benzyl)chroman-6-sulfonamido)acetic acid $^1$H NMR (500 MHz, CDCl3) δ 7.88 (d, J=8.1 Hz, 1H), 7.84 (d, J=8.2 Hz, 1H), 7.78 (d, J=8.5 Hz, 1H), 7.61-7.55 (m, 2H), 7.50 (d, J=7.3 Hz, 1H), 7.47 (d, J=7.0 Hz, 1H), 7.44-7.38 (m, 3H), 7.32 (d, J=7.0 Hz, 1H), 7.29 (dd, J=5.5, 3.2 Hz, 1H), 7.27 (s, 1H), 6.81-6.77 (m, 1H), 4.52 (s, 2H), 4.00 (s, 2H), 2.69 (t, J=6.7 Hz, 2H), 1.73 (t, J=6.7 Hz, 2H), 1.29 (s, 6H). LRMS [ESI, MH$^+$] m/z calcd for C30H30NO5S 516.18, found 516.2.

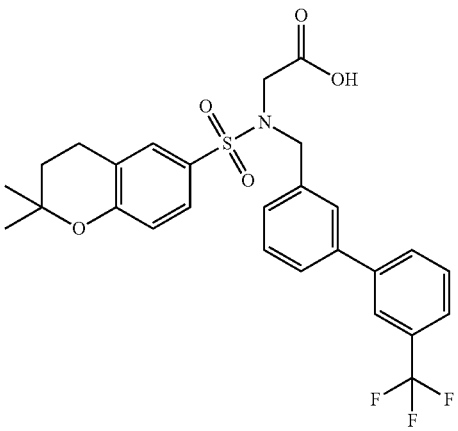 [SMILES: CC1(C)CCc2cc(S(=O)(=O)N(CC(=O)O)Cc3cccc(-c4cccc(C(F)(F)F)c4)c3)ccc2O1]

Example 11

2-(2,2-dimethyl-N-((3'-(trifluoromethyl)biphenyl-3-yl)methyl)chroman-6-sulfonamido)acetic acid $^1$H NMR (500 MHz, CDCl3) δ 7.76 (s, 1H), 7.67 (d, J=7.7 Hz, 1H), 7.60 (d, J=6.8 Hz, 3H), 7.55 (d, J=7.7 Hz, 1H), 7.51 (d, J=8.0 Hz, 1H), 7.41 (dd, J=8.6, 6.7 Hz, 2H), 7.26 (d, J=8.2 Hz, 1H), 6.87-6.82 (m, 1H), 4.53 (s, 2H), 3.96 (s, 2H), 2.77 (t, J=6.7 Hz, 2H), 1.79 (t, J=6.7 Hz, 2H), 1.32 (s, 6H). LRMS [ESI, MH$^-$] m/z calcd for C27H27F3NO5S 534.16, found 534.2.

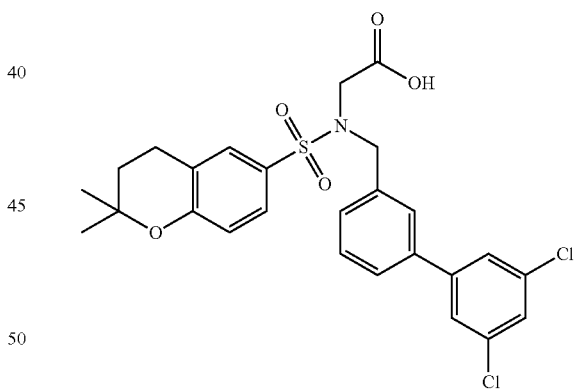

Example 12

2-(N-((3,5'-dichlorobiphenyl-3-yl)methyl)-2,2-dimethylchroman-6-sulfonamido)acetic acid $^1$H NMR (500 MHz, CDCl3) δ 7.61-7.57 (m, 2H), 7.44 (d, J=7.8 Hz, 1H), 7.39 (d, J=7.6 Hz, 1H), 7.37 (d, J=1.8 Hz, 2H), 7.34 (s, 1H), 7.32 (t, J=1.8 Hz, 1H), 7.26 (d, J=7.0 Hz, 1H), 6.87-6.83 (m, 1H), 4.51 (s, 2H), 3.95 (s, 2H), 2.77 (t, J=6.7 Hz, 2H), 1.79 (t, J=6.7 Hz, 2H), 1.32 (s, 6H). LRMS [ESI, MH$^+$] m/z calcd for C26H26Cl2NO5S 534.09, found 534.2.

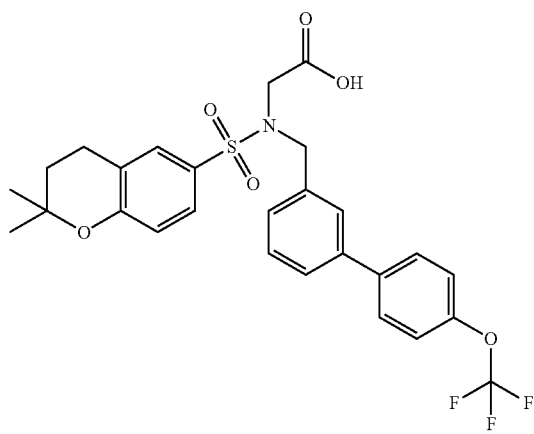 [SMILES: CC1(C)CCc2cc(S(=O)(=O)N(CC(=O)O)Cc3cccc(-c4ccc(OC(F)(F)F)cc4)c3)ccc2O1]

Example 13

2-(2,2-dimethyl-N-((4'-(trifluoromethoxy)biphenyl-3-yl)methyl)chroman-6-sulfonamido)acetic acid ¹H NMR (500 MHz, CDCl3) δ 7.59 (dd, J=6.1, 2.5 Hz, 2H), 7.51-7.48 (m, 2H), 7.46 (d, J=7.8 Hz, 1H), 7.37 (t, J=7.7 Hz, 1H), 7.35 (s, 1H), 7.26 (d, J=8.3 Hz, 2H), 7.20 (d, J=7.6 Hz, 1H), 6.87-6.82 (m, 1H), 4.51 (s, 2H), 3.95 (s, 2H), 2.76 (t, J=6.7 Hz, 2H), 1.79 (t, J=6.7 Hz, 2H), 1.32 (s, 6H). LRMS [ESI, MH⁺] m/z calcd for C27H27F3NO6S 550.15, found 550.2.

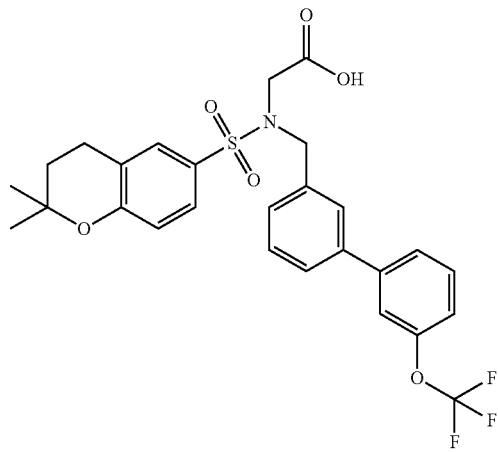 [SMILES: CC1(C)CCc2cc(S(=O)(=O)N(CC(=O)O)Cc3cccc(-c4cccc(OC(F)(F)F)c4)c3)ccc2O1]

Example 14

2-(2,2-dimethyl-N-((3'-(trifluoromethoxy)biphenyl-3-yl)methyl)chroman-6-sulfonamido)acetic acid ¹H NMR (500 MHz, CDCl3) δ 7.60 (dd, J=6.0, 2.5 Hz, 2H), 7.48 (d, J=7.8 Hz, 1H), 7.46-7.42 (m, 2H), 7.39 (dd, J=8.8, 6.5 Hz, 2H), 7.35 (s, 1H), 7.24 (d, J=9.6 Hz, 1H), 7.19 (d, J=7.0 Hz, 1H), 6.86-6.82 (m, 1H), 4.52 (s, 2H), 3.96 (s, 2H), 2.77 (t, J=6.7 Hz, 2H), 1.79 (t, J=6.7 Hz, 2H), 1.32 (s, 6H). LRMS [ESI, MH⁺] m/z calcd for C27H27F3NO6S 550.15, found 550.2.

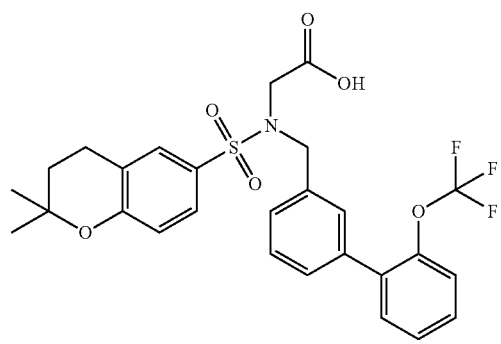 [SMILES: CC1(C)CCc2cc(S(=O)(=O)N(CC(=O)O)Cc3cccc(-c4ccccc4OC(F)(F)F)c3)ccc2O1]

Example 15

2-(2,2-dimethyl-N-((2'-(trifluoromethoxy)biphenyl-3-yl)methyl)chroman-6-sulfonamido)acetic acid ¹H NMR (500 MHz, CDCl3) δ 7.63-7.56 (m, 2H), 7.40-7.30 (m, 6H), 7.28-7.23 (m, 2H), 6.83 (d, J=8.4 Hz, 1H), 4.51 (s, 2H), 3.95 (s, 2H), 2.77 (t, J=6.7 Hz, 2H), 1.79 (t, J=6.7 Hz, 2H), 1.33 (s, 6H). LRMS [ESI, MH⁺] m/z calcd for C27H27F3NO6S 550.15, found 550.1.

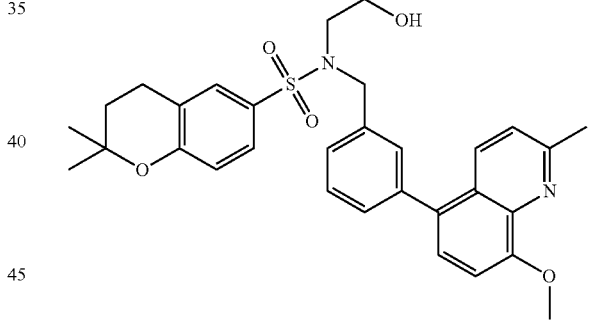

Example 16

2-(N-(3-(8-methoxy-2-methylquinolin-5-yl)benzyl)-2,2-dimethylchroman-6-sulfonamido)acetic acid. TFA ¹H NMR (500 MHz, CDCl3) δ 8.69 (d, J=8.8 Hz, 1H), 7.68 (d, J=8.9 Hz, 1H), 7.59 (d, J=8.1 Hz, 1H), 7.57 (d, J=1.9 Hz, 1H), 7.53 (dd, J=8.6, 2.2 Hz, 1H), 7.41 (t, J=7.6 Hz, 1H), 7.38 (s, 1H), 7.32 (d, J=8.3 Hz, 1H), 7.27 (dd, J=12.7, 4.7 Hz, 2H), 6.79 (d, J=8.6 Hz, 1H), 4.41 (s, 2H), 4.06 (s, 3H), 3.88 (s, 2H), 2.99 (s, 3H), 2.75 (t, J=6.6 Hz, 2H), 1.81-1.73 (m, 2H), 1.31 (s, 6H). LRMS [ESI, MH⁺] m/z calcd for C31H33N2O6S 561.21, found 560.2.

29

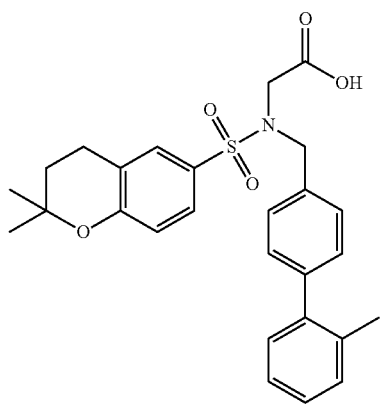

Example 17

2-(2,2-dimethyl-N-((2'-methylbiphenyl-4-yl)methyl)chroman-6-sulfonamido)acetic acid $^1$H NMR (500 MHz, CDCl3) δ 7.63 (d, J=2.1 Hz, 1H), 7.60 (dd, J=8.6, 2.3 Hz, 1H), 7.31-7.24 (m, 6H), 7.22 (dd, J=8.3, 3.2 Hz, 1H), 7.18 (d, J=6.5 Hz, 1H), 6.85 (d, J=8.6 Hz, 1H), 4.50 (s, 2H), 3.98 (s, 2H), 2.82 (t, J=6.7 Hz, 2H), 2.24 (s, 3H), 1.83 (t, J=6.7 Hz, 2H), 1.35 (s, 6H). LRMS [ESI, MH$^+$] m/z calcd for C27H30NO5S 480.18, found 480.2.

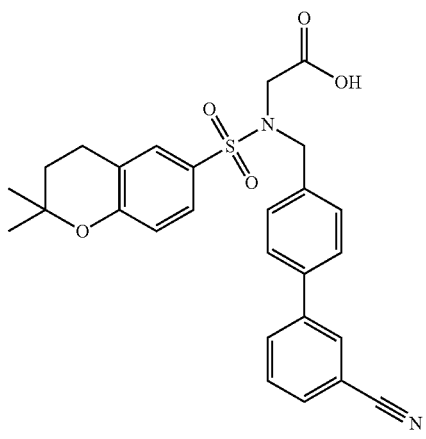 [SMILES: CC1(C)CCc2cc(S(=O)(=O)N(CC(=O)O)Cc3ccc(-c4cccc(C#N)c4)cc3)ccc2O1]

Example 18

2-(N-((3'-cyanobiphenyl-4-yl)methyl)-2,2-dimethyl-chroman-6-sulfonamido)acetic acid $^1$H NMR (500 MHz, CDCl3) δ 7.83 (d, J=1.6 Hz, 1H), 7.78 (d, J=7.9 Hz, 1H), 7.64-7.61 (m, 2H), 7.60 (dd, J=8.6, 2.3 Hz, 1H), 7.54 (t, J=7.8 Hz, 1H), 7.51 (d, J=8.2 Hz, 2H), 7.35 (d, J=8.1 Hz, 2H), 6.86 (d, J=8.5 Hz, 1H), 4.50 (s, 2H), 3.96 (s, 2H), 2.82 (t, J=6.7 Hz, 2H), 1.84 (t, J=6.7 Hz, 2H), 1.36 (s, 6H). LRMS [ESI, MH$^+$] m/z calcd for C27H27N2O5S 491.16, found 491.2.

30

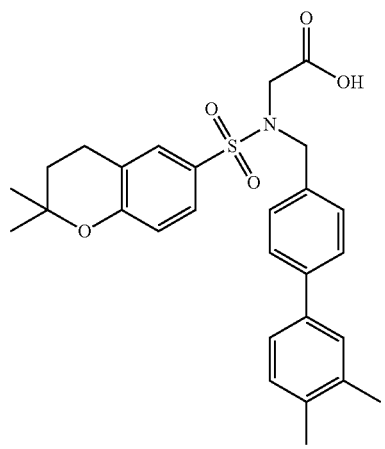

Example 19

2-(N-((3',4'-dimethylbiphenyl-4-yl)methyl)-2,2-dimethylchroman-6-sulfonamido)acetic acid $^1$H NMR (500 MHz, CDCl3) δ 7.62-7.57 (m, 2H), 7.51 (d, J=8.1 Hz, 2H), 7.33 (s, 1H), 7.29 (d, J=7.8 Hz, 1H), 7.26 (d, J=8.1 Hz, 2H), 7.19 (d, J=7.8 Hz, 1H), 6.85 (d, J=8.3 Hz, 1H), 4.48 (s, 2H), 3.95 (s, 2H), 2.80 (t, J=6.7 Hz, 2H), 2.32 (s, 3H), 2.29 (s, 3H), 1.82 (t, J=6.7 Hz, 2H), 1.35 (s, 6H). LRMS [ESI, MH$^+$] m/z calcd for C28H32NO5S 494.2, found 494.2.

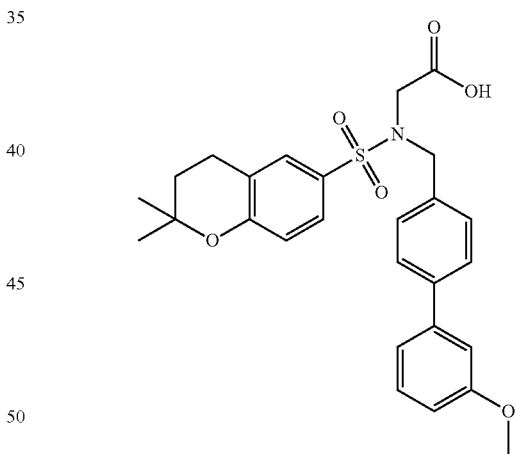

Example 20

2-(N-((3'-methoxybiphenyl-4-yl)methyl)-2,2-dimethylchroman-6-sulfonamido)acetic acid $^1$H NMR (500 MHz, CDCl3) δ 7.62-7.58 (m, 2H), 7.52 (d, J=8.1 Hz, 2H), 7.34 (t, J=7.9 Hz, 1H), 7.28 (d, J=8.1 Hz, 2H), 7.14 (d, J=7.7 Hz, 1H), 7.09-7.06 (m, 1H), 6.89 (dd, J=8.2, 2.5 Hz, 1H), 6.85 (d, J=8.3 Hz, 1H), 4.48 (s, 2H), 3.95 (s, 2H), 3.85 (s, 3H), 2.80 (t, J=6.7 Hz, 2H), 1.82 (t, J=6.7 Hz, 2H), 1.35 (s, 6H). LRMS [ESI, MH$^+$] m/z calcd for 27H30NO6S 496.18, found 496.2.

31

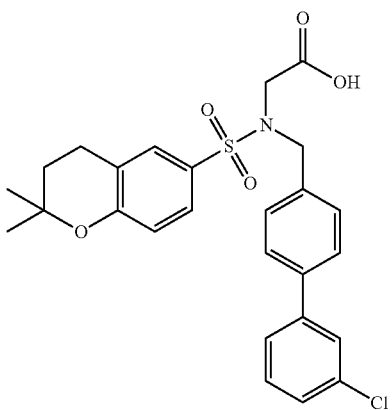 [SMILES: CC1(C)CCc2cc(S(=O)(=O)N(CC(=O)O)Cc3ccc(-c4cccc(Cl)c4)cc3)ccc2O1]

Example 21

2-(N-((3'-chlorobiphenyl-4-yl)methyl)-2,2-dimethyl-chroman-6-sulfonamido)acetic acid ¹H NMR (500 MHz, CDCl3) δ 7.62-7.57 (m, 2H), 7.53 (t, J=1.8 Hz, 1H), 7.49 (d, J=8.2 Hz, 2H), 7.43 (dt, J=7.6, 1.4 Hz, 1H), 7.35 (t, J=7.7 Hz, 1H), 7.33-7.27 (m, 3H), 6.85 (d, J=8.3 Hz, 1H), 4.49 (s, 2H), 3.95 (s, 2H), 2.80 (t, J=6.7 Hz, 2H), 1.83 (t, J=6.7 Hz, 2H), 1.35 (s, 6H). LRMS [ESI, MH⁺] m/z calcd for C26H27ClNO5S 500.13, found 500.2.

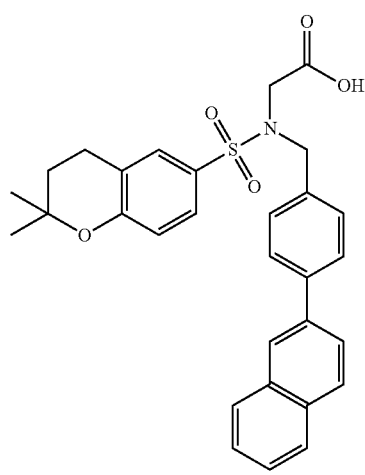

Example 22

2-(2,2-dimethyl-N-(4-(naphthalen-2-yl)benzyl)chroman-6-sulfonamido)acetic acid

¹H NMR (500 MHz, CDCl3) δ 8.01 (s, 1H), 7.89 (t, J=8.9 Hz, 2H), 7.87-7.84 (m, 1H), 7.70 (dd, J=8.5, 1.8 Hz, 1H), 7.66 (d, J=8.2 Hz, 2H), 7.63-7.59 (m, 2H), 7.52-7.46 (m, 2H), 7.33 (d, J=8.1 Hz, 2H), 6.87 (d, J=8.9 Hz, 1H), 4.51 (s, 2H), 3.98 (s, 2H), 2.81 (t, J=6.7 Hz, 2H), 1.83 (t, J=6.7 Hz, 2H), 1.35 (s, 6H). LRMS [ESI, MH⁺] m/z calcd for C30H30NO5S 516.18, found 516.2.

32

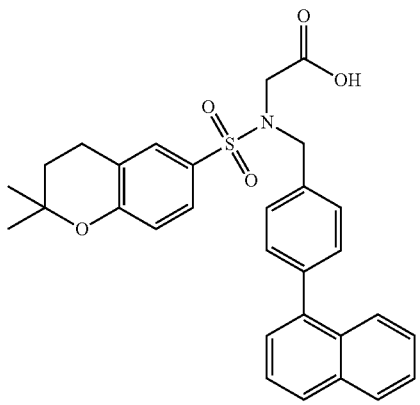 [SMILES: CC1(C)CCc2cc(S(=O)(=O)N(CC(=O)O)Cc3ccc(-c4cccc5ccccc45)cc3)ccc2O1]

Example 23

2-(2,2-dimethyl-N-(4-(naphthalen-1-yl)benzyl)chroman-6-sulfonamido)acetic acid

¹H NMR (500 MHz, CDCl3) δ 7.89 (d, J=8.1 Hz, 1H), 7.84 (t, J=8.6 Hz, 2H), 7.65 (d, J=2.0 Hz, 1H), 7.62 (dd, J=8.6, 2.3 Hz, 1H), 7.53-7.46 (m, 2H), 7.46-7.40 (m, 3H), 7.40-7.36 (m, 1H), 7.34 (d, J=8.0 Hz, 2H), 6.87 (d, J=8.6 Hz, 1H), 4.55 (s, 2H), 4.04 (s, 2H), 2.82 (t, J=6.7 Hz, 2H), 1.83 (t, J=6.7 Hz, 2H), 1.35 (s, 6H). LRMS [ESI, MH⁺] m/z calcd for C30H30NO5S 516.18, found 516.2.

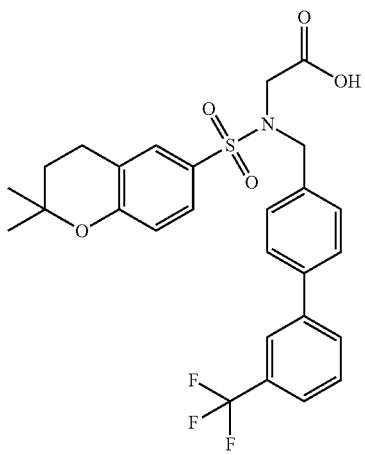 [SMILES: CC1(C)CCc2cc(S(=O)(=O)N(CC(=O)O)Cc3ccc(-c4cccc(C(F)(F)F)c4)cc3)ccc2O1]

Example 24

2-(2,2-dimethyl-N-((3'-(trifluoromethyl)biphenyl-4-yl)methyl)chroman-6-sulfonamido)acetic acid ¹H NMR (500 MHz, CDCl3) δ 7.79 (s, 1H), 7.73 (d, J=7.7 Hz, 1H), 7.62-7.58 (m, J=8.2 Hz, 3H), 7.55 (d, J=7.8 Hz, 1H), 7.54-7.51 (m, 2H), 7.32 (d, J=8.1 Hz, 2H), 6.86 (d, J=8.3 Hz, 1H), 4.50 (s, 2H), 3.96 (s, 2H), 2.80 (t, J=6.7 Hz, 2H), 1.83 (t, J=6.7 Hz, 2H), 1.34 (s, 6H). LRMS [ESI, MH⁺] m/z calcd for C27H27F3NO5S 534.16, found 534.2.

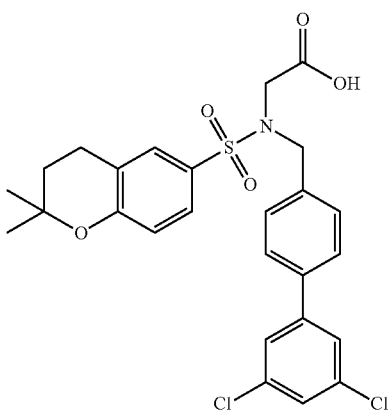 [SMILES: CC1(C)CCc2cc(S(=O)(=O)N(CC(=O)O)Cc3ccc(-c4cc(Cl)cc(Cl)c4)cc3)ccc2O1]

Example 25

2-(N-((3,5'-dichlorobiphenyl-4-yl)methyl)-2,2-dimethylchroman-6-sulfonamido)acetic acid $^1$H NMR (500 MHz, CDCl3) δ 7.62-7.57 (m, 2H), 7.46 (d, J=8.2 Hz, 2H), 7.41 (d, J=1.8 Hz, 2H), 7.33 (t, J=1.8 Hz, 1H), 7.31 (d, J=8.2 Hz, 2H), 6.85 (d, J=8.5 Hz, 1H), 4.48 (s, 2H), 3.95 (s, 2H), 2.80 (t, J=6.7 Hz, 2H), 1.83 (t, J=6.7 Hz, 2H), 1.35 (s, 6H). LRMS [ESI, MH$^+$] m/z calcd for C26H26Cl2NO5S 534.09, found 534.1.

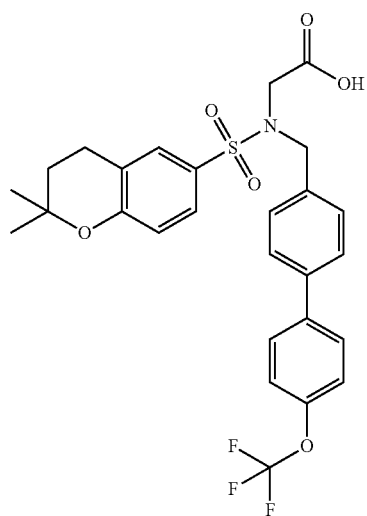 [SMILES: CC1(C)CCc2cc(S(=O)(=O)N(CC(=O)O)Cc3ccc(-c4ccc(OC(F)(F)F)cc4)cc3)ccc2O1]

Example 26

2-(2,2-dimethyl-N-((4'-(trifluoromethoxy)biphenyl-4-yl)methyl)chroman-6-sulfonamido)acetic acid $^1$H NMR (500 MHz, CDCl3) δ 7.62-7.58 (m, 2H), 7.56 (d, J=8.7 Hz, 2H), 7.49 (d, J=8.1 Hz, 2H), 7.31 (d, J=8.1 Hz, 2H), 7.27 (d, J=8.5 Hz, 2H), 6.86 (d, J=8.5 Hz, 1H), 4.49 (s, 2H), 3.95 (s, 2H), 2.81 (t, J=6.7 Hz, 2H), 1.83 (t, J=6.7 Hz, 2H), 1.35 (s, 6H). LRMS [ESI, MH$^+$] m/z calcd for C27H27F3NO6S 550.15, found 550.2.

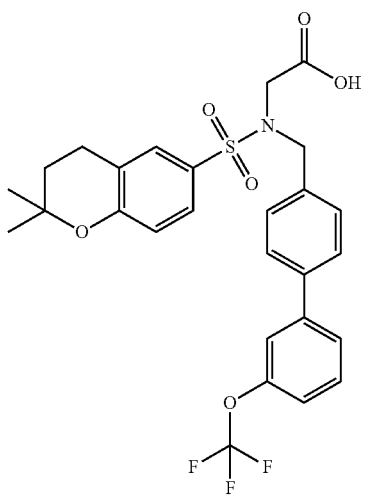 [SMILES: CC1(C)CCc2cc(S(=O)(=O)N(CC(=O)O)Cc3ccc(-c4cccc(OC(F)(F)F)c4)cc3)ccc2O1]

Example 27

2-(2,2-dimethyl-N-((3'-(trifluoromethoxy)biphenyl-4-yl)methyl)chroman-6-sulfonamido)acetic acid $^1$H NMR (500 MHz, CDCl3) δ 7.62-7.58 (m, 2H), 7.51 (d, J=8.2 Hz, 2H), 7.48 (d, J=7.9 Hz, 1H), 7.44 (t, J=7.8 Hz, 1H), 7.39 (s, 1H), 7.31 (t, J=7.3 Hz, 2H), 7.20 (d, J=7.9 Hz, 1H), 6.86 (d, J=8.4 Hz, 1H), 4.50 (s, 2H), 3.96 (s, 2H), 2.80 (t, J=6.7 Hz, 2H), 1.83 (t, J=6.7 Hz, 2H), 1.35 (s, 6H). LRMS [ESI, MH$^+$] m/z calcd for C27H27F3NO6S 550.15, found 550.2.

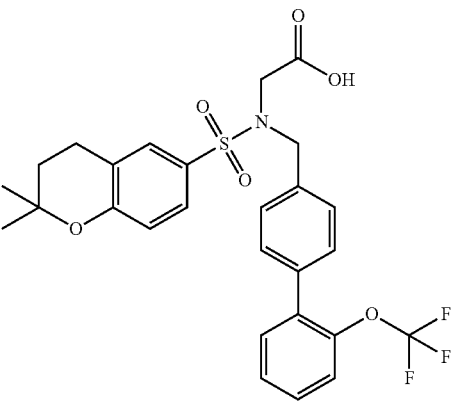 [SMILES: CC1(C)CCc2cc(S(=O)(=O)N(CC(=O)O)Cc3ccc(-c4ccccc4OC(F)(F)F)cc3)ccc2O1]

Example 28

2-(2,2-dimethyl-N-((2'-(trifluoromethoxy)biphenyl-4-yl)methyl)chroman-6-sulfonamido)acetic acid $^1$H NMR (500 MHz, CDCl3) δ 7.62 (s, 1H), 7.60 (dd, J=8.6, 2.3 Hz, 1H), 7.42-7.38 (m, 3H), 7.38-7.36 (m, 1H), 7.35 (d, J=6.9 Hz, 1H), 7.34-7.31 (m, 1H), 7.28 (d, J=8.1 Hz, 2H), 6.85 (d, J=8.6 Hz, 1H), 4.50 (s, 2H), 3.97 (s, 2H), 2.81 (t, J=6.7 Hz, 2H), 1.86-1.79 (m, 2H), 1.35 (s, 6H). LRMS [ESI, MH$^+$] m/z calcd for C27H27F3NO6S 550.15, found 550.2.

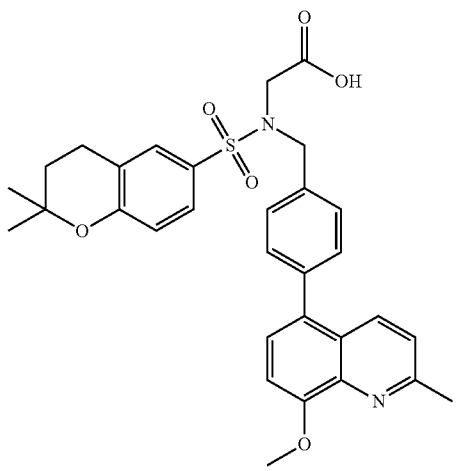

Example 29

2-(N-(4-(8-methoxy-2-methylquinolin-5-yl)benzyl)-
2,2-dimethylchroman-6-sulfonamido)acetic acid $^1$H NMR (500 MHz, CDCl3) δ 8.53 (d, J=8.8 Hz, 1H), 7.62 (d, J=2.1 Hz, 1H), 7.59-7.57 (m, 1H), 7.57-7.55 (m, 1H), 7.54 (d, J=8.2 Hz, 1H), 7.34 (d, J=8.0 Hz, 2H), 7.30 (d, J=8.3 Hz, 1H), 7.25 (d, J=8.0 Hz, 2H), 6.81 (d, J=8.6 Hz, 1H), 4.44 (s, 2H), 4.10 (s, 3H), 3.86 (s, 2H), 3.03 (s, 3H), 2.81 (t, J=6.7 Hz, 2H), 1.81 (t, J=6.7 Hz, 2H), 1.33 (s, 6H). LRMS [ESI, MH$^+$] m/z calcd for C31H33N2O6S 561.21, found 561.3.

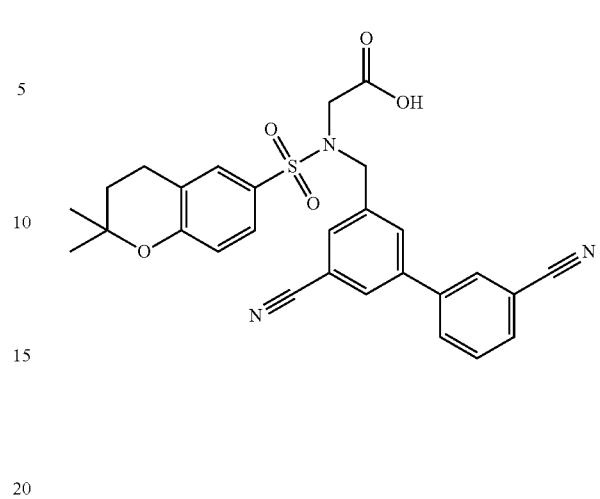

Example 31

2-(N-((3',5-dicyanobiphenyl-3-yl)methyl)-2,2-dimethylchroman-6-sulfonamido)acetic acid $^1$H NMR (500 MHz, CDCl3) δ 7.81-7.77 (m, 2H), 7.75 (t, J=3.0 Hz, 2H), 7.70 (d, J=7.7 Hz, 1H), 7.62-7.55 (m, 3H), 7.54 (s, 1H), 6.85 (d, J=8.4 Hz, 1H), 4.54 (s, 2H), 4.00 (s, 2H), 2.80 (t, J=6.7 Hz, 2H), 1.82 (t, J=6.7 Hz, 2H), 1.35 (s, 6H). LRMS [ESI, MH$^+$] m/z calcd for C28H26N3O5S 516.16, found 516.2.

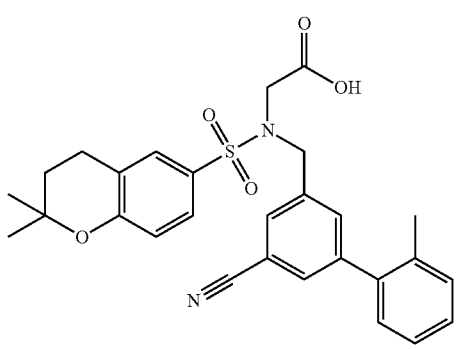 [SMILES: Cc1ccccc1-c1cc(C#N)cc(CN(CC(=O)O)S(=O)(=O)c2ccc3c(c2)CCC(C)(C)O3)c1]

Example 30

2-(N-((5-cyano-2'-methylbiphenyl-3-yl)methyl)-2,2-dimethylchroman-6-sulfonamido)acetic acid $^1$H NMR (500 MHz, CDCl3) δ 7.58 (s, 1H), 7.56 (dd, J=8.6, 2.3 Hz, 1H), 7.53 (s, 1H), 7.46 (d, J=5.2 Hz, 2H), 7.32-7.27 (m, 2H), 7.26-7.22 (m, 1H), 7.11 (d, J=7.5 Hz, 1H), 6.84 (d, J=8.6 Hz, 1H), 4.52 (s, 2H), 4.00 (s, 2H), 2.79 (t, J=6.7 Hz, 2H), 2.20 (s, 3H), 1.82 (t, J=6.7 Hz, 2H), 1.34 (s, 6H). LRMS [ESI, MH$^+$] m/z calcd for C28H29N2O5S 505.18, found 505.2.

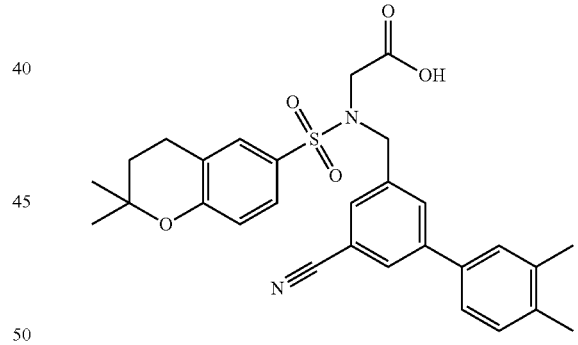

Example 32

2-(N-((5-cyano-3',4'-dimethylbiphenyl-3-yl)methyl)-
2,2-dimethylchroman-6-sulfonamido)acetic acid $^1$H NMR (500 MHz, CDCl3) δ 7.75 (s, 1H), 7.67 (s, 1H), 7.57 (dd, J=6.0, 2.7 Hz, 2H), 7.39 (s, 1H), 7.27 (s, 1H), 7.21 (s, 2H), 6.86-6.82 (m, 1H), 4.53 (s, 2H), 3.99 (s, 2H), 2.77 (t, J=6.7 Hz, 2H), 2.32 (s, 3H), 2.30 (s, 3H), 1.80 (t, J=6.7 Hz, 2H), 1.33 (s, 6H). LRMS [ESI, MH$^+$] m/z calcd for C29H31N2O5S 519.2, found 519.3.

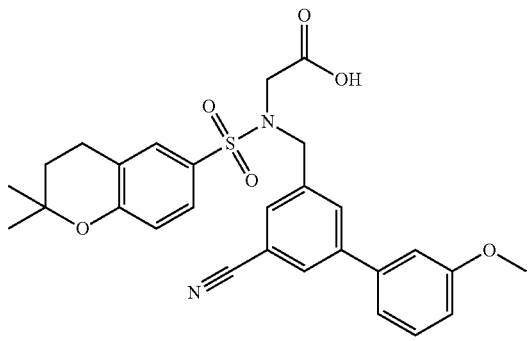

Example 33

2-(N-((5-cyano-3'-methoxybiphenyl-3-yl)methyl)-2,2-dimethylchroman-6-sulfonamido)acetic acid ¹H NMR (500 MHz, CDCl3) δ 7.76 (s, 1H), 7.69 (s, 1H), 7.60-7.55 (m, J=6.6 Hz, 2H), 7.43 (s, 1H), 7.37 (t, J=8.0 Hz, 1H), 7.06 (d, J=7.7 Hz, 1H), 7.03-7.01 (m, 1H), 6.95 (dd, J=8.2, 2.4 Hz, 1H), 6.88-6.82 (m, 1H), 4.53 (s, 2H), 3.99 (s, 2H), 3.86 (s, 3H), 2.78 (t, J=6.7 Hz, 2H), 1.81 (t, J=6.7 Hz, 2H), 1.34 (s, 6H). LRMS [ESI, MH⁺] m/z calcd for C28H29N2O6S 521.17, found 521.3.

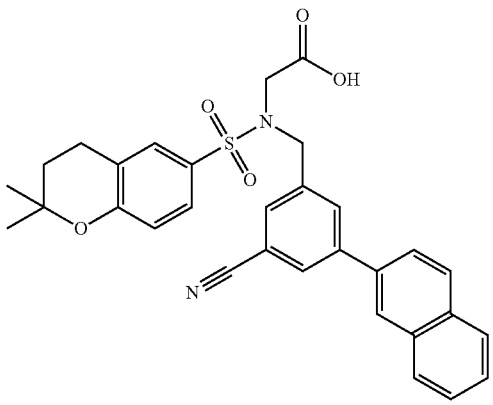

Example 35

2-(N-(3-cyano-5-(naphthalen-2-yl)benzyl)-2,2-dimethylchroman-6-sulfonamido)acetic acid ¹H NMR (500 MHz, CDCl3) δ 7.97 (s, 1H), 7.96-7.90 (m, 3H), 7.89 (s, 1H), 7.85 (s, 1H), 7.64-7.59 (m, 3H), 7.55-7.52 (m, 2H), 7.49 (s, 1H), 6.87 (d, J=9.5 Hz, 1H), 4.59 (s, 2H), 4.03 (s, 2H), 2.79 (d, J=6.7 Hz, 2H), 1.79 (t, J=6.6 Hz, 2H), 1.32 (s, 6H). LRMS [ESI, MH⁺] m/z calcd for C31H29N2O5S 541.18, found 541.2.

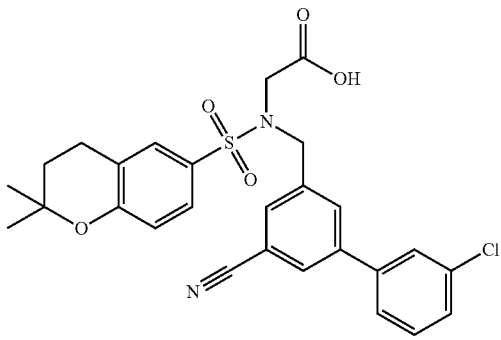 [SMILES: CC1(C)CCc2cc(S(=O)(=O)N(CC(=O)O)Cc3cc(C#N)cc(-c4cccc(Cl)c4)c3)ccc2O1]

Example 34

2-(N-((3'-chloro-5-cyanobiphenyl-3-yl)methyl)-2,2-dimethylchroman-6-sulfonamido)acetic acid ¹H NMR (500 MHz, CDCl3) δ 7.74 (d, J=1.3 Hz, 1H), 7.69 (s, 1H), 7.60-7.54 (m, 2H), 7.47 (s, 2H), 7.42-7.35 (m, 3H), 6.88-6.82 (m, 1H), 4.54 (s, 2H), 3.99 (s, 2H), 2.78 (t, J=6.6 Hz, 2H), 1.81 (t, J=6.7 Hz, 2H), 1.33 (s, 6H). LRMS [ESI, MH⁺] m/z calcd for C27H26ClN2O5S 525.13, found 525.2.

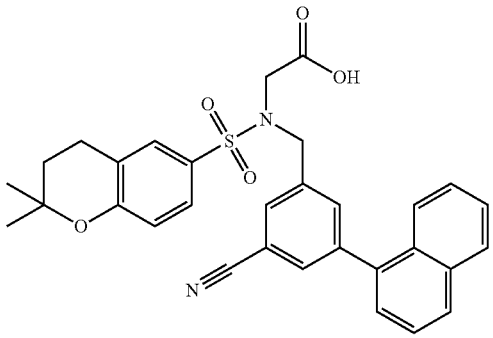 [SMILES: CC1(C)CCc2cc(S(=O)(=O)N(CC(=O)O)Cc3cc(C#N)cc(-c4cccc5ccccc45)c3)ccc2O1]

Example 36

2-(N-(3-cyano-5-(naphthalen-1-yl)benzyl)-2,2-dimethylchroman-6-sulfonamido)acetic acid ¹H NMR (500 MHz, CDCl3) δ 7.90 (t, J=8.1 Hz, 2H), 7.70 (s, 1H), 7.66 (d, J=8.3 Hz, 1H), 7.59 (d, J=6.9 Hz, 1H), 7.55 (dd, J=9.9, 4.2 Hz, 3H), 7.53-7.49 (m, 2H), 7.46 (dd, J=11.2, 4.1 Hz, 1H), 7.31 (d, J=6.6 Hz, 1H), 6.81 (d, J=8.5 Hz, 1H), 4.55 (s, 2H), 4.03 (s, 2H), 2.74 (t, J=6.7 Hz, 2H), 1.77 (t, J=6.7 Hz, 2H), 1.31 (s, 6H). LRMS [ESI, MH⁺] m/z calcd for C31H29N2O5S 541.18, found 541.2.

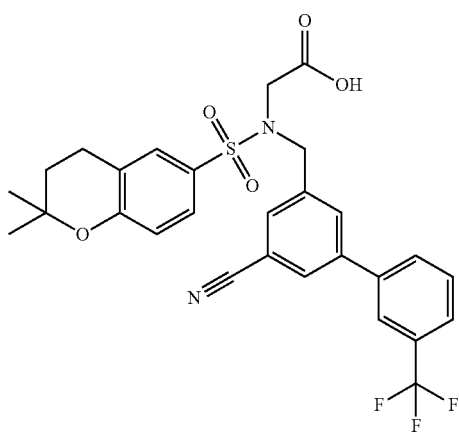 [SMILES: CC1(C)CCc2cc(S(=O)(=O)N(CC(=O)O)Cc3cc(C#N)cc(-c4cccc(C(F)(F)F)c4)c3)ccc2O1]

Example 37

2-(N-((5-cyano-3'-(trifluoromethyl)biphenyl-3-yl)methyl)-2,2-dimethylchroman-6-sulfonamido)acetic acid ¹H NMR (500 MHz, CDCl3) δ 7.78 (d, J=1.4 Hz, 1H), 7.75 (d, J=1.6 Hz, 2H), 7.70-7.66 (m, 2H), 7.61 (d, J=7.7 Hz, 1H), 7.59-7.55 (m, 2H), 7.52 (s, 1H), 6.87-6.82 (m, 1H), 4.55 (s, 2H), 4.00 (s, 2H), 2.79 (t, J=6.7 Hz, 2H), 1.81 (t, J=6.7 Hz, 2H), 1.34 (s, 6H). LRMS [ESI, MH⁺] m/z calcd for C28H26F3N2O5S 559.15, found 559.2.

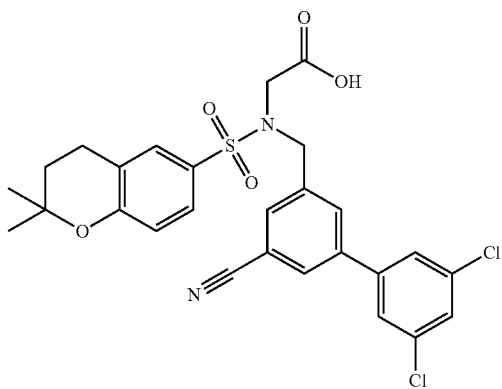 [SMILES: CC1(C)CCc2cc(S(=O)(=O)N(CC(=O)O)Cc3cc(C#N)cc(-c4cc(Cl)cc(Cl)c4)c3)ccc2O1]

Example 38

2-(N-((3,5'-dichloro-5-cyanobiphenyl-3-yl)methyl)-2,2-dimethylchroman-6-sulfonamido)acetic acid ¹H NMR (500 MHz, CDCl3) δ 7.71 (s, 1H), 7.68 (s, 1H), 7.58-7.54 (m, 2H), 7.51 (s, 1H), 7.40 (t, J=1.7 Hz, 1H), 7.37 (d, J=1.7 Hz, 2H), 6.87-6.82 (m, 1H), 4.53 (s, 2H), 3.99 (s, 2H), 2.79 (t, J=6.7 Hz, 2H), 1.81 (t, J=6.7 Hz, 2H), 1.34 (s, 6H). LRMS [ESI, MH⁺] m/z calcd for C27H25Cl2N2O5S 559.09, found 559.2.

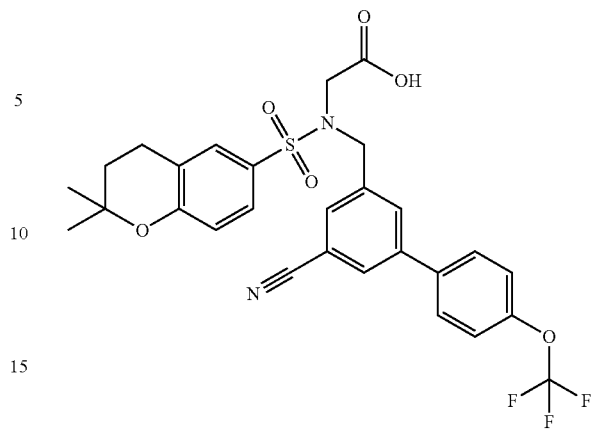

Example 39

2-(N-((5-cyano-4'-(trifluoromethoxy)biphenyl-3-yl)methyl)-2,2-dimethylchroman-6-sulfonamido)acetic acid ¹H NMR (500 MHz, CDCl3) δ 7.74 (s, 1H), 7.71 (s, 1H), 7.60-7.55 (m, 2H), 7.54-7.49 (m, 2H), 7.47 (s, 1H), 7.31 (d, J=8.4 Hz, 2H), 6.85 (d, J=8.3 Hz, 1H), 4.54 (s, 2H), 3.99 (s, 2H), 2.79 (t, J=6.7 Hz, 2H), 1.82 (t, J=6.7 Hz, 2H), 1.34 (s, 6H). LRMS [ESI, MH⁺] m/z calcd for C28H26F3N2O6S 575.15, found 575.2.

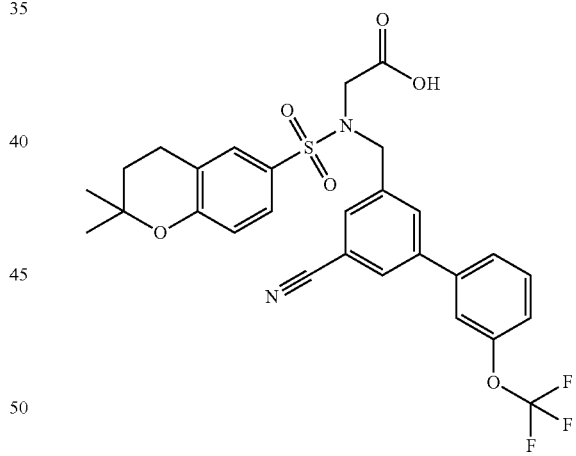

Example 40

2-(N-((5-cyano-3'-(trifluoromethoxy)biphenyl-3-yl)methyl)-2,2-dimethylchroman-6-sulfonamido)acetic acid ¹H NMR (500 MHz, CDCl3) δ 7.75 (s, 1H), 7.73 (s, 1H), 7.59-7.55 (m, 2H), 7.50 (t, J=7.9 Hz, 2H), 7.43 (d, J=7.8 Hz, 1H), 7.35 (s, 1H), 7.28 (d, J=8.0 Hz, 1H), 6.85 (d, J=9.0 Hz, 1H), 4.55 (s, 2H), 4.00 (s, 2H), 2.79 (t, J=6.7 Hz, 2H), 1.82 (t, J=6.7 Hz, 2H), 1.34 (s, 6H). LRMS [ESI, MH⁺] m/z calcd for C28H26F3N2O6S 575.15, found 575.2.

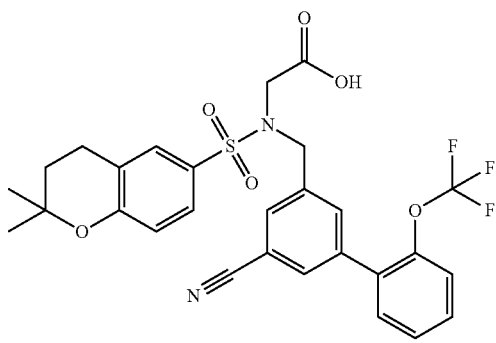 [SMILES: CC1(C)CCc2cc(S(=O)(=O)N(CC(=O)O)Cc3cc(C#N)cc(-c4ccccc4OC(F)(F)F)c3)ccc2O1]

Example 41

2-(N-((5-cyano-2'-(trifluoromethoxy)biphenyl-3-yl)methyl)-2,2-dimethylchroman-6-sulfonamido)acetic acid $^1$H NMR (500 MHz, CDCl3) δ 7.67 (s, 1H), 7.60-7.57 (m, 2H), 7.56 (dd, J=8.6, 2.3 Hz, 1H), 7.50 (s, 1H), 7.48-7.42 (m, 1H), 7.41-7.37 (m, 1H), 7.37-7.33 (m, 2H), 6.83 (d, J=8.6 Hz, 1H), 4.54 (s, 2H), 3.98 (s, 2H), 2.79 (t, J=6.7 Hz, 2H), 1.81 (t, J=6.7 Hz, 2H), 1.34 (s, 6H). LRMS [ESI, MH$^+$] m/z calcd for C28H26F3N2O6S 575.15, found 575.2.

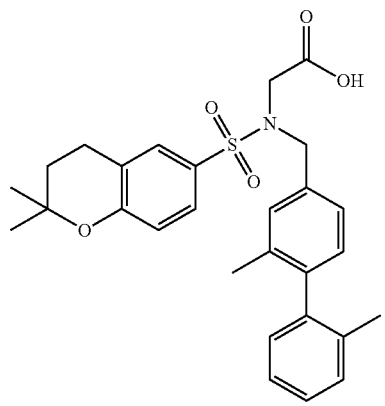

Example 43

2-(N-((2,2'-dimethylbiphenyl-4-yl)methyl)-2,2-dimethylchroman-6-sulfonamido)acetic acid $^1$H NMR (500 MHz, CDCl3) δ 7.64 (d, J=2.2 Hz, 1H), 7.61 (dd, J=8.6, 2.3 Hz, 1H), 7.25 (d, J=4.0 Hz, 2H), 7.21 (dt, J=12.3, 4.3 Hz, 1H), 7.07-7.02 (m, 4H), 6.86 (d, J=8.6 Hz, 1H), 4.47 (s, 2H), 4.00 (s, 2H), 2.83 (t, J=6.7 Hz, 2H), 2.01 (s, 3H), 1.99 (s, 3H), 1.84 (t, J=6.7 Hz, 2H), 1.35 (s, 6H). LRMS [ESI, MH$^+$] m/z calcd for C28H32NO5S 494.2, found 494.3.

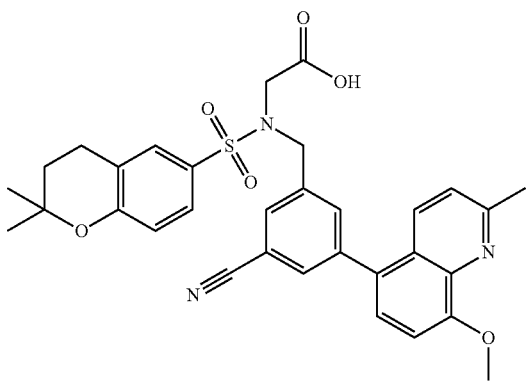

Example 42

2-(N-(3-cyano-5-(8-methoxy-2-methylquinolin-5-yl)benzyl)-2,2-dimethylchroman-6-sulfonamido)acetic acid $^1$H NMR (500 MHz, CDCl3) δ 8.52 (d, J=8.8 Hz, 1H), 7.81 (s, 1H), 7.58 (d, J=8.8 Hz, 1H), 7.55 (dd, J=4.9, 2.5 Hz, 4H), 7.51 (dd, J=8.6, 2.2 Hz, 1H), 7.27 (d, J=8.3 Hz, 1H), 6.82 (d, J=8.6 Hz, 1H), 4.39 (s, 2H), 4.07 (s, 3H), 3.89 (s, 2H), 2.92 (s, 3H), 2.79 (t, J=6.6 Hz, 2H), 1.81 (t, J=6.7 Hz, 2H), 1.34 (s, 6H). LRMS [ESI, MH$^-$] m/z calcd for C32H32N3O6S 586.2, found 586.2.

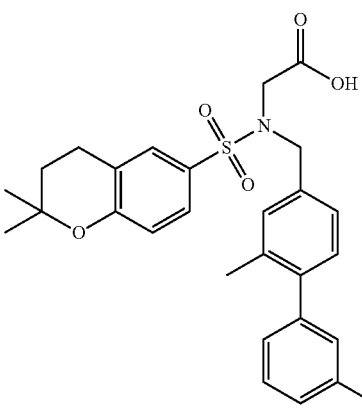

Example 44

2-(N-((3'-cyano-2-methylbiphenyl-4-yl)methyl)-2,2-dimethylchroman-6-sulfonamido)acetic acid $^1$H NMR (500 MHz, CDCl3) δ 7.65-7.61 (m, 2H), 7.60 (dd, J=8.6, 2.3 Hz, 1H), 7.57 (d, J=1.0 Hz, 1H), 7.52 (dd, J=6.5, 3.0 Hz, 2H), 7.11 (s, 3H), 6.86 (d, J=8.6 Hz, 1H), 4.47 (s, 2H), 3.97 (s, 2H), 2.82 (t, J=6.7 Hz, 2H), 2.18 (s, 3H), 1.84 (t, J=6.7 Hz, 2H), 1.35 (s, 6H). LRMS [ESI, MH$^+$] m/z calcd for C28H29N2O5S 505.18, found 505.2.

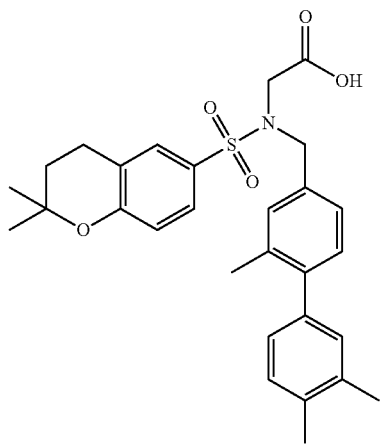

Example 45

2-(2,2-dimethyl-N-((2,3,4'-trimethylbiphenyl-4-yl)methyl)chroman-6-sulfonamido)acetic acid $^1$H NMR (500 MHz, CDCl3) δ 7.62 (s, 1H), 7.60 (dd, J=8.6, 2.3 Hz, 1H), 7.18-7.12 (m, 2H), 7.05 (s, 1H), 7.05-6.99 (m, 3H), 6.85 (d, J=8.6 Hz, 1H), 4.46 (s, 2H), 3.98 (s, 2H), 2.81 (t, J=6.7 Hz, 2H), 2.30 (s, 3H), 2.29 (s, 3H), 2.21 (s, 3H), 1.83 (t, J=6.7 Hz, 2H), 1.35 (s, 6H). LRMS [ESI, MH$^+$] m/z calcd for C29H34NO5S 508.22, found 508.3.

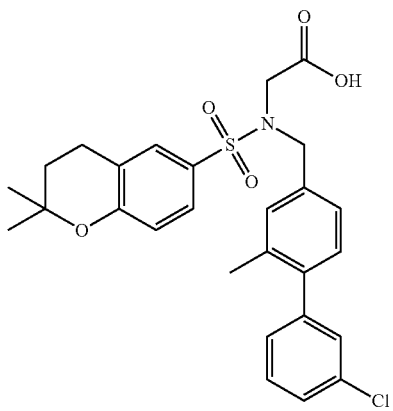

Example 47

2-(N-((3'-chloro-2-methylbiphenyl-4-yl)methyl)-2,2-dimethylchroman-6-sulfonamido)acetic acid $^1$H NMR (500 MHz, CDCl3) δ 7.62 (d, J=2.2 Hz, 1H), 7.60 (dd, J=8.6, 2.4 Hz, 1H), 7.35-7.29 (m, 2H), 7.27 (d, J=2.1 Hz, 1H), 7.17-7.14 (m, 1H), 7.13-7.10 (m, 1H), 7.09-7.04 (m, 2H), 6.85 (d, J=8.6 Hz, 1H), 4.46 (s, 2H), 3.97 (s, 2H), 2.86-2.76 (m, 2H), 2.19 (s, 3H), 1.83 (t, J=6.7 Hz, 2H), 1.35 (s, 6H). LRMS [ESI, MH$^+$] m/z calcd for C27H29ClNO5S 514.15, found 514.2.

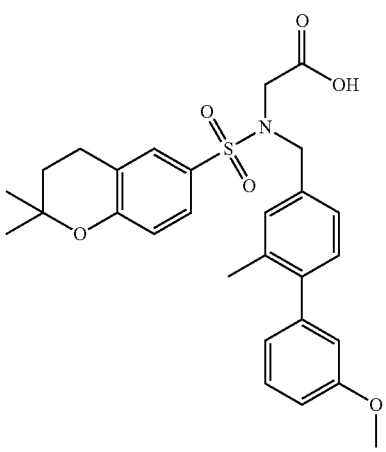

Example 46

2-(N-((3'-methoxy-2-methylbiphenyl-4-yl)methyl)-2,2-dimethylchroman-6-sulfonamido)acetic acid $^1$H NMR (500 MHz, CDCl3) δ 7.62 (s, 1H), 7.60 (dd, J=8.6, 2.3 Hz, 1H), 7.31 (t, J=7.9 Hz, 1H), 7.18-7.13 (m, 1H), 7.07-7.02 (m, 2H), 6.88 (dd, J=8.4, 2.6 Hz, 1H), 6.86 (dd, J=8.1, 2.5 Hz, 2H), 6.83-6.78 (m, 1H), 4.46 (s, 2H), 3.97 (d, J=11.2 Hz, 2H), 3.82 (s, 3H), 2.82 (t, J=6.7 Hz, 2H), 2.21 (s, 3H), 1.83 (t, J=6.7 Hz, 2H), 1.35 (s, 6H). LRMS [ESI, MH$^+$] m/z calcd for C28H32NO6S 510.2, found 510.2.

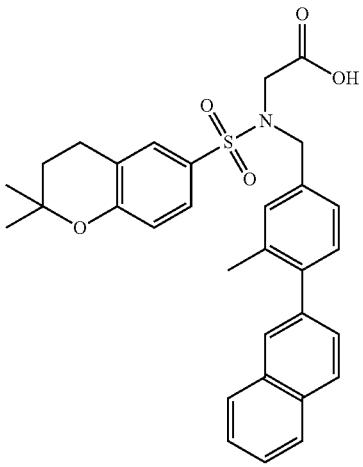 [SMILES: Cc1cc(CN(CC(=O)O)S(=O)(=O)c2ccc3c(c2)CCC(C)(C)O3)ccc1-c1ccc2ccccc2c1]

Example 48

2-(2,2-dimethyl-N-(3-methyl-4-(naphthalen-2-yl)benzyl)chroman-6-sulfonamido)acetic acid $^1$H NMR (500 MHz, CDCl3) δ 7.89-7.82 (m, 3H), 7.73 (s, 1H), 7.65 (d, J=2.2 Hz, 1H), 7.62 (dd, J=8.6, 2.4 Hz, 1H), 7.52-7.47 (m, 2H), 7.42 (dd, J=8.4, 1.7 Hz, 1H), 7.25 (d, J=8.3 Hz, 1H), 7.13-7.07 (m, 2H), 6.87 (d, J=8.6 Hz, 1H), 4.50 (s, 2H), 4.01 (s, 2H), 2.83 (t, J=6.7 Hz, 2H), 2.25 (s, 3H), 1.84 (t, J=6.7 Hz, 2H), 1.35 (s, 6H). LRMS [ESI, MH$^+$] m/z calcd for C31H32NO5S 530.2, found 530.3.

45

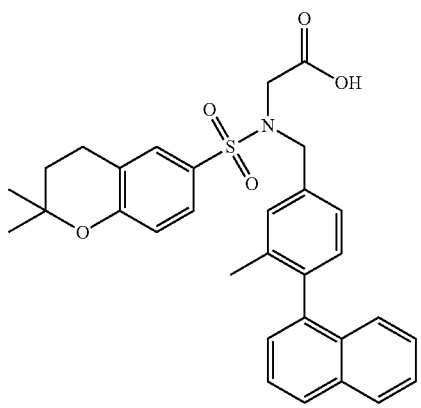 [SMILES: Cc1cc(CN(CC(=O)O)S(=O)(=O)c2ccc3c(c2)CCC(C)(C)O3)ccc1-c1cccc2ccccc12]

Example 49

2-(2,2-dimethyl-N-(3-methyl-4-(naphthalen-1-yl)benzyl)chroman-6-sulfonamido)acetic acid $^1$H NMR (500 MHz, CDCl3) δ 7.89 (d, J=8.2 Hz, 1H), 7.85 (d, J=8.2 Hz, 1H), 7.66 (s, 1H), 7.63 (dd, J=8.6, 2.2 Hz, 1H), 7.52-7.48 (m, 1H), 7.48-7.44 (m, 1H), 7.37 (d, J=3.8 Hz, 2H), 7.28 (d, J=6.9 Hz, 1H), 7.18 (d, J=7.6 Hz, 1H), 7.13 (s, 1H), 7.11 (d, J=7.8 Hz, 1H), 6.87 (d, J=8.6 Hz, 1H), 4.53 (s, 2H), 4.05 (s, 2H), 2.83 (t, J=6.7 Hz, 2H), 1.96 (s, 3H), 1.84 (t, J=6.7 Hz, 2H), 1.35 (s, 6H). LRMS [ESI, MH$^+$] m/z calcd for C31H32NO5S 530.2, found 530.3.

Example 50

2-(2,2-dimethyl-N-((2-methyl-3'-(trifluoromethyl)biphenyl-4-yl)methyl)chroman-6-sulfonamido)acetic acid $^1$H NMR (500 MHz, CDCl3) δ 7.63 (d, J=2.2 Hz, 1H), 7.61 (d, J=2.4 Hz, 1H), 7.59 (d, J=2.1 Hz, 1H), 7.55-7.50 (m, 2H), 7.46 (d, J=7.7 Hz, 1H), 7.15 (d, J=8.4 Hz, 1H), 7.11-7.07 (m, 2H), 6.86 (d, J=8.6 Hz, 1H), 4.47 (s, 2H), 3.97 (s, 2H), 2.82 (t, J=6.7 Hz, 2H), 2.19 (s, 3H), 1.84 (t, J=6.7 Hz, 2H), 1.35 (s, 6H). LRMS [ESI, MH$^+$] m/z calcd for C28H29F3NO5S 548.17, found 548.2.

46

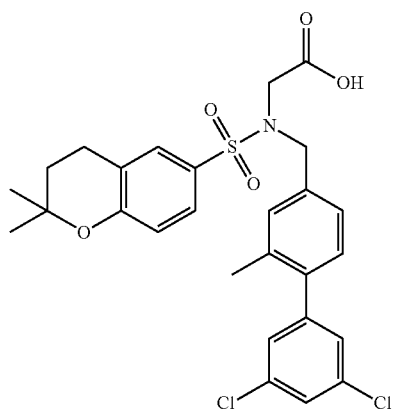 [SMILES: Cc1cc(CN(CC(=O)O)S(=O)(=O)c2ccc3c(c2)CCC(C)(C)O3)ccc1-c1cc(Cl)cc(Cl)c1]

Example 51

2-(N-((3',5'-dichloro-2-methylbiphenyl-4-yl)methyl)-2,2-dimethylchroman-6-sulfonamido)acetic acid $^1$H NMR (500 MHz, CDCl3) δ 7.62 (d, J=2.2 Hz, 1H), 7.59 (dd, J=8.6, 2.4 Hz, 1H), 7.34 (t, J=1.9 Hz, 1H), 7.16 (d, J=1.9 Hz, 2H), 7.12-7.05 (m, 3H), 6.85 (d, J=8.6 Hz, 1H), 4.46 (s, 2H), 3.96 (s, 2H), 2.82 (t, J=6.7 Hz, 2H), 2.19 (s, 3H), 1.84 (t, J=6.7 Hz, 2H), 1.35 (s, 6H). LRMS [ESI, MH$^+$] m/z calcd for C27H28Cl2NO5S 548.11, found 548.1.

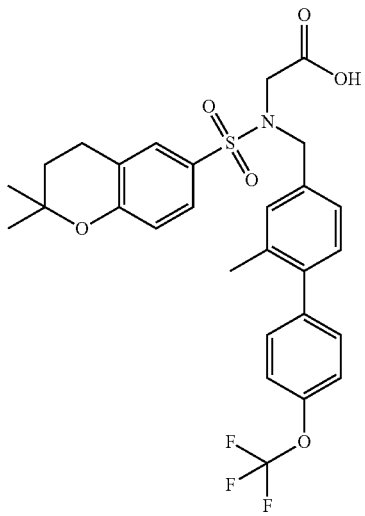 [SMILES: Cc1cc(CN(CC(=O)O)S(=O)(=O)c2ccc3c(c2)CCC(C)(C)O3)ccc1-c1ccc(OC(F)(F)F)cc1]

Example 52

2-(2,2-dimethyl-N-((2-methyl-4'-(trifluoromethoxy)biphenyl-4-yl)methyl)chroman-6-sulfonamido)acetic acid $^1$H NMR (500 MHz, CDCl3) δ 7.63 (d, J=2.2 Hz, 1H), 7.60 (dd, J=8.6, 2.3 Hz, 1H), 7.31-7.27 (m, 2H), 7.24 (d, J=8.4 Hz, 1H), 7.15-7.11 (m, 1H), 7.10-7.05 (m, 2H), 6.85 (d, J=8.6 Hz, 1H), 4.46 (s, 2H), 3.97 (s, 2H), 2.82 (t, J=6.7 Hz, 2H), 2.19 (s, 3H), 1.83 (t, J=6.7 Hz, 2H), 1.35 (s, 6H). LRMS [ESI, MH$^+$] m/z calcd for C28H29F3NO6S 564.17, found 564.2.

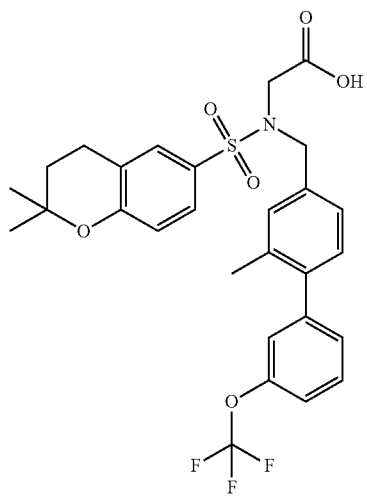 [SMILES: Cc1cc(CN(CC(=O)O)S(=O)(=O)c2ccc3c(c2)CCC(C)(C)O3)ccc1-c1cccc(OC(F)(F)F)c1]

Example 53

2-(2,2-dimethyl-N-((2-methyl-3'-(trifluoromethoxy)biphenyl-4-yl)methyl)chroman-6-sulfonamido)acetic acid ¹H NMR (500 MHz, CDCl3) δ 7.62 (s, 1H), 7.60 (dd, J=8.6, 2.3 Hz, 1H), 7.42 (t, J=7.9 Hz, 1H), 7.20 (t, J=8.4 Hz, 2H), 7.16-7.11 (m, 2H), 7.10-7.06 (m, 2H), 6.86 (d, J=8.6 Hz, 1H), 4.47 (s, 2H), 3.97 (s, 2H), 2.82 (t, J=6.7 Hz, 2H), 2.20 (s, 3H), 1.84 (t, J=6.7 Hz, 2H), 1.35 (s, 6H). LRMS [ESI, MH⁺] m/z calcd for C28H29F3NO6S 564.17, found 564.2.

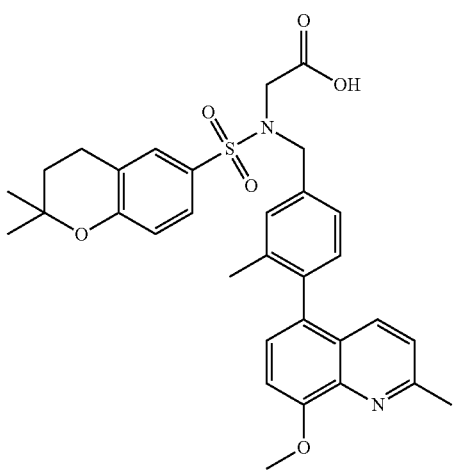

Example 55

2-(N-(4-(8-methoxy-2-methylquinolin-5-yl)-3-methylbenzyl)-2,2-dimethylchroman-6-sulfonamido)acetic acid ¹H NMR (500 MHz, CDCl3) δ 8.00 (d, J=8.7 Hz, 1H), 7.63 (d, J=1.9 Hz, 1H), 7.58 (dd, J=8.6, 2.2 Hz, 1H), 7.47 (d, J=8.7 Hz, 1H), 7.41 (d, J=8.0 Hz, 1H), 7.25 (d, J=7.9 Hz, 1H), 7.15 (s, 1H), 7.11 (d, J=7.9 Hz, 1H), 7.06 (d, J=7.7 Hz, 1H), 6.81 (d, J=8.6 Hz, 1H), 4.46 (s, 2H), 4.10 (s, 3H), 3.93 (s, 2H), 2.98 (s, 3H), 2.81 (t, J=6.7 Hz, 2H), 1.90 (s, 3H), 1.81 (t, J=6.7 Hz, 2H), 1.33 (s, 6H). LRMS [ESI, MH⁺] m/z calcd for C32H35N2O6S 575.22, found 575.3.

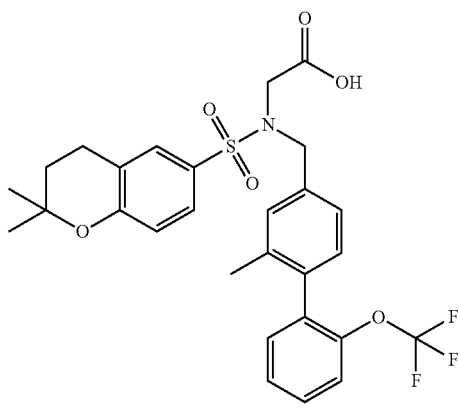 [SMILES: Cc1cc(CN(CC(=O)O)S(=O)(=O)c2ccc3c(c2)CCC(C)(C)O3)ccc1-c1ccccc1OC(F)(F)F]

Example 54

2-(2,2-dimethyl-N-((2-methyl-2'-(trifluoromethoxy)biphenyl-4-yl)methyl)chroman-6-sulfonamido)acetic acid ¹H NMR (500 MHz, CDCl3) δ 7.64 (d, J=2.1 Hz, 1H), 7.60 (dd, J=8.6, 2.3 Hz, 1H), 7.42-7.36 (m, 1H), 7.33 (t, J=7.0 Hz, 2H), 7.24 (dd, J=7.8, 1.6 Hz, 1H), 7.09 (d, J=7.6 Hz, 1H), 7.07-7.03 (m, 2H), 6.86 (d, J=8.6 Hz, 1H), 4.47 (s, 2H), 3.98 (s, 2H), 2.84-2.78 (m, 2H), 2.06 (s, 3H), 1.86-1.80 (m, 2H), 1.35 (s, 6H). LRMS [ESI, MH⁺] m/z calcd for C28H29F3NO6S 564.17, found 564.2.

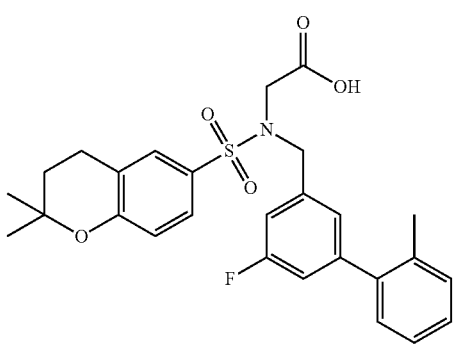 [SMILES: Cc1ccccc1-c1cc(F)cc(CN(CC(=O)O)S(=O)(=O)c2ccc3c(c2)CCC(C)(C)O3)c1]

Example 56

2-(N-((5-fluoro-2'-methylbiphenyl-3-yl)methyl)-2,2-dimethylchroman-6-sulfonamido)acetic acid ¹H NMR (500 MHz, CDCl3) δ 7.61-7.55 (m, 2H), 7.28-7.19 (m, 3H), 7.12 (d, J=7.4 Hz, 1H), 6.97-6.92 (m, 2H), 6.90 (d, J=9.1 Hz, 1H), 6.83 (d, J=8.4 Hz, 1H), 4.48 (s, 2H), 3.99 (s, 2H), 2.77 (t, J=6.7 Hz, 2H), 2.21 (s, 3H), 1.80 (t, J=6.7 Hz, 2H), 1.33 (s, 6H). LRMS [ESI, MH⁺] m/z calcd for C27H29FNO5S 498.18, found 498.3.

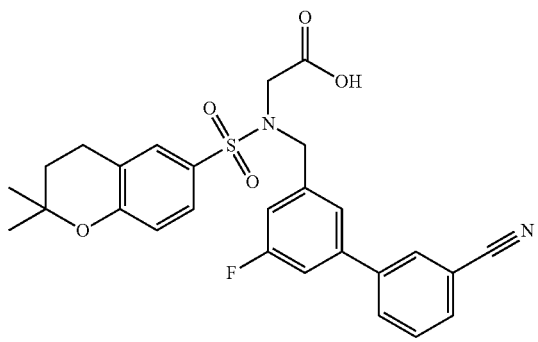 [SMILES: CC1(C)CCc2cc(S(=O)(=O)N(CC(=O)O)Cc3cc(F)cc(-c4cccc(C#N)c4)c3)ccc2O1]

Example 57

2-(N-((3'-cyano-5-fluorobiphenyl-3-yl)methyl)-2,2-dimethylchroman-6-sulfonamido)acetic acid ¹H NMR (500 MHz, CDCl3) δ 7.77 (d, J=1.6 Hz, 1H), 7.72 (dd, J=7.9, 1.2 Hz, 1H), 7.67-7.63 (m, 1H), 7.61-7.57 (m, 2H), 7.55 (t, J=7.8 Hz, 1H), 7.24 (s, 1H), 7.17 (dd, J=9.3, 1.8 Hz, 1H), 6.98 (d, J=8.8 Hz, 1H), 6.85 (d, J=9.0 Hz, 1H), 4.51 (s, 2H), 3.99 (s, 2H), 2.79 (t, J=6.7 Hz, 2H), 1.81 (t, J=6.7 Hz, 2H), 1.34 (s, 6H). LRMS [ESI, MH⁺] m/z calcd for C27H26FN2O5S 509.15, found 509.2.

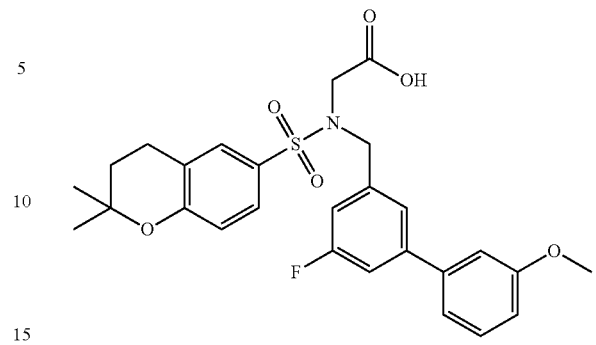

Example 59

2-(N-((5-fluoro-3'-methoxybiphenyl-3-yl)methyl)-2,2-dimethylchroman-6-sulfonamido)acetic acid ¹H NMR (500 MHz, CDCl3) δ 7.63-7.55 (m, 2H), 7.33 (t, J=7.9 Hz, 1H), 7.22-7.16 (m, 2H), 7.06 (dd, J=10.2, 3.3 Hz, 1H), 7.04-7.00 (m, 1H), 6.93-6.87 (m, 2H), 6.86-6.82 (m, 1H), 4.50 (s, 2H), 3.98 (s, 2H), 3.85 (s, 3H), 2.78 (t, J=6.7 Hz, 2H), 1.80 (t, J=6.7 Hz, 2H), 1.33 (s, 6H). LRMS [ESI, MH⁺] m/z calcd for C27H29FNO6S 514.17, found 514.2.

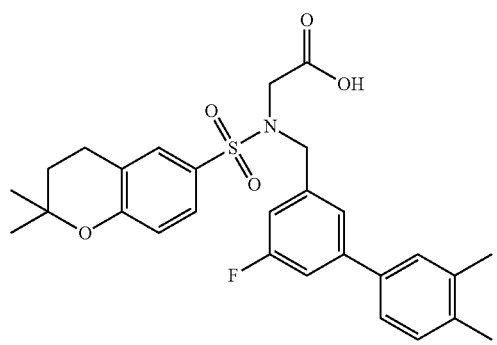

Example 58

2-(N-((5-fluoro-3',4'-dimethylbiphenyl-3-yl)methyl)-2,2-dimethylchroman-6-sulfonamido)acetic acid ¹H NMR (500 MHz, CDCl3) δ 7.65-7.56 (m, 2H), 7.26 (s, 1H), 7.24-7.15 (m, 4H), 6.91-6.78 (m, 2H), 4.50 (s, 2H), 3.98 (s, 2H), 2.77 (t, J=6.6 Hz, 2H), 2.31 (s, 3H), 2.29 (s, 3H), 1.79 (t, J=6.7 Hz, 2H), 1.32 (s, 6H). LRMS [ESI, MH⁺] m/z calcd for C28H31FNO5S 512.19, found 512.3.

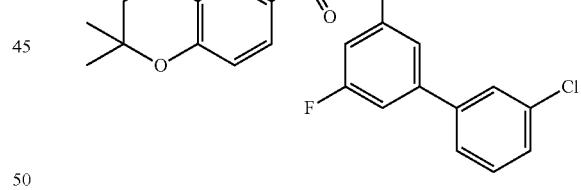

Example 60

2-(N-((3'-chloro-5-fluorobiphenyl-3-yl)methyl)-2,2-dimethylchroman-6-sulfonamido)acetic acid ¹H NMR (500 MHz, CDCl3) δ 7.61-7.55 (m, 2H), 7.47 (s, 1H), 7.38-7.31 (m, 3H), 7.19-7.14 (m, 2H), 6.93 (d, J=8.8 Hz, 1H), 6.87-6.82 (m, 1H), 4.50 (s, 2H), 3.98 (s, 2H), 2.78 (t, J=6.7 Hz, 2H), 1.80 (t, J=6.7 Hz, 2H), 1.33 (s, 6H). LRMS [ESI, MH⁺] m/z calcd for C26H26ClFNO5S 518.12, found 518.2.

51

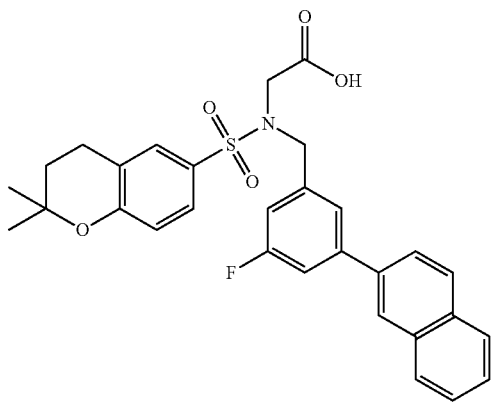 [SMILES: CC1(C)CCc2cc(S(=O)(=O)N(CC(=O)O)Cc3cc(F)cc(-c4ccc5ccccc5c4)c3)ccc2O1]

Example 61

2-(N-(3-fluoro-5-(naphthalen-2-yl)benzyl)-2,2-dimethylchroman-6-sulfonamido)acetic acid $^1$H NMR (500 MHz, CDCl3) δ 7.94 (s, 1H), 7.91-7.82 (m, 3H), 7.63-7.57 (m, 3H), 7.54-7.47 (m, 2H), 7.37-7.28 (m, 2H), 6.91 (d, J=8.9 Hz, 1H), 6.86 (d, J=9.3 Hz, 1H), 4.54 (s, 2H), 4.01 (s, 2H), 2.76 (t, J=6.7 Hz, 2H), 1.75 (t, J=6.7 Hz, 2H), 1.30 (s, 6H). LRMS [ESI, MH$^+$] m/z calcd for C30H29FNO5S 534.18, found 534.2.

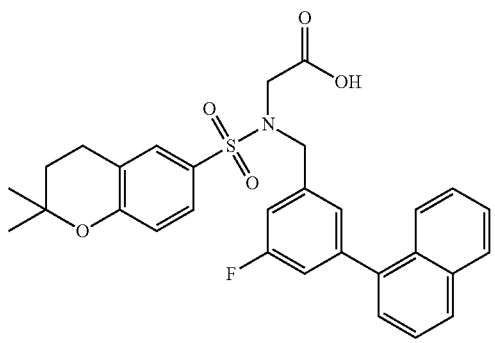 [SMILES: CC1(C)CCc2cc(S(=O)(=O)N(CC(=O)O)Cc3cc(F)cc(-c4cccc5ccccc45)c3)ccc2O1]

Example 62

2-(N-(3-fluoro-5-(naphthalen-1-yl)benzyl)-2,2-dimethylchroman-6-sulfonamido)acetic acid $^1$H NMR (500 MHz, CDCl3) δ 7.89 (d, J=8.1 Hz, 1H), 7.85 (d, J=8.2 Hz, 1H), 7.77 (d, J=8.4 Hz, 1H), 7.60-7.55 (m, 2H), 7.49 (t, J=7.6 Hz, 2H), 7.44 (dd, J=11.2, 4.0 Hz, 1H), 7.31 (t, J=7.6 Hz, 1H), 7.12 (d, J=9.1 Hz, 1H), 7.08 (s, 1H), 7.00 (d, J=9.1 Hz, 1H), 6.80 (d, J=8.4 Hz, 1H), 4.52 (s, 2H), 4.02 (s, 2H), 2.72 (t, J=6.7 Hz, 2H), 1.75 (t, J=6.7 Hz, 2H), 1.30 (s, 6H). LRMS [ESI, MH$^+$] m/z calcd for C30H29FNO5S 534.18, found 534.2.

52

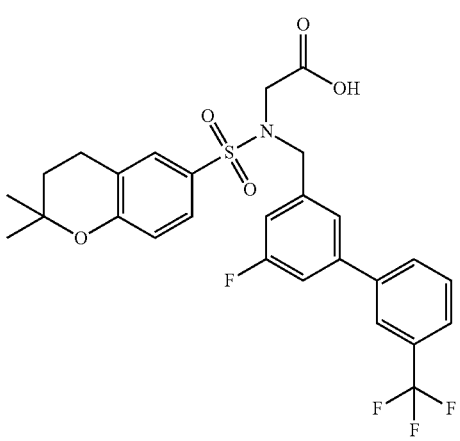 [SMILES: CC1(C)CCc2cc(S(=O)(=O)N(CC(=O)O)Cc3cc(F)cc(-c4cccc(C(F)(F)F)c4)c3)ccc2O1]

Example 63

2-(N-((5-fluoro-3'-(trifluoromethyl)biphenyl-3-yl)methyl)-2,2-dimethylchroman-6-sulfonamido)acetic acid $^1$H NMR (500 MHz, CDCl3) δ 7.73 (s, 1H), 7.67 (d, J=7.7 Hz, 1H), 7.63 (d, J=7.8 Hz, 1H), 7.61-7.53 (m, 3H), 7.23 (s, 1H), 7.20 (d, J=9.3 Hz, 1H), 6.97 (d, J=8.8 Hz, 1H), 6.87-6.82 (m, 1H), 4.52 (s, 2H), 3.99 (s, 2H), 2.78 (t, J=6.7 Hz, 2H), 1.80 (t, J=6.7 Hz, 2H), 1.33 (s, 6H). LRMS [ESI, MH$^+$] m/z calcd for C27H26F4NO5S 552.15, found 552.2.

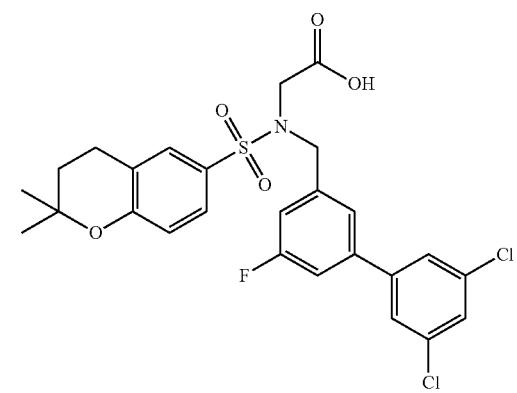 [SMILES: CC1(C)CCc2cc(S(=O)(=O)N(CC(=O)O)Cc3cc(F)cc(-c4cc(Cl)cc(Cl)c4)c3)ccc2O1]

Example 64

2-(N-((3,5'-dichloro-5-fluorobiphenyl-3-yl)methyl)-2,2-dimethylchroman-6-sulfonamido)acetic acid $^1$H NMR (500 MHz, CDCl3) δ 7.60-7.56 (m, 2H), 7.36 (s, 3H), 7.16 (s, 1H), 7.14 (dd, J=9.2, 2.0 Hz, 1H), 6.98 (d, J=8.8 Hz, 1H), 6.88-6.83 (m, 1H), 4.50 (s, 2H), 3.98 (s, 2H), 2.78 (t, J=6.7 Hz, 2H), 1.80 (t, J=6.7 Hz, 2H), 1.33 (s, 6H). LRMS [ESI, MH$^+$] m/z calcd for C26H25Cl2FNO5S 552.08, found 552.1.

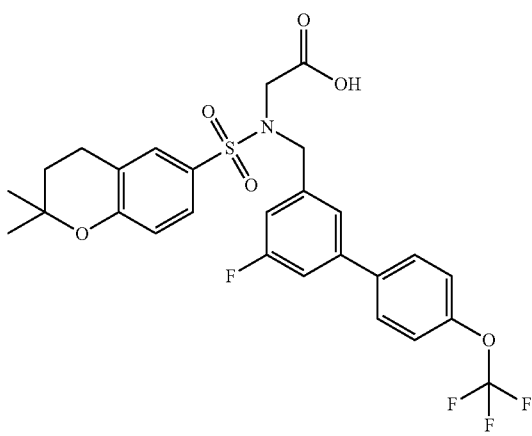 [SMILES: CC1(C)CCc2cc(S(=O)(=O)N(CC(=O)O)Cc3cc(F)cc(-c4ccc(OC(F)(F)F)cc4)c3)ccc2O1]

Example 65

2-(N-((5-fluoro-4'-(trifluoromethoxy)biphenyl-3-yl)methyl)-2,2-dimethylchroman-6-sulfonamido)acetic acid $^1$H NMR (500 MHz, CDCl3) δ 7.61-7.57 (m, 2H), 7.52-7.49 (m, 1H), 7.49-7.46 (m, 1H), 7.27 (d, J=8.3 Hz, 2H), 7.19-7.14 (m, 2H), 6.91 (d, J=8.9 Hz, 1H), 6.87-6.83 (m, 1H), 4.51 (s, 2H), 3.98 (s, 2H), 2.78 (t, J=6.7 Hz, 2H), 1.80 (t, J=6.7 Hz, 2H), 1.33 (s, 6H). LRMS [ESI, MH$^+$] m/z calcd for C27H26F4NO6S 568.14, found 568.2.

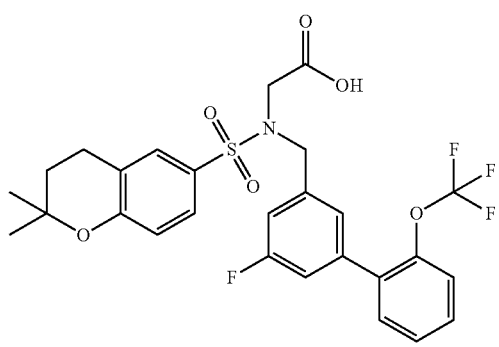 [SMILES: CC1(C)CCc2cc(S(=O)(=O)N(CC(=O)O)Cc3cc(F)cc(-c4ccccc4OC(F)(F)F)c3)ccc2O1]

Example 67

2-(N-((5-fluoro-2'-(trifluoromethoxy)biphenyl-3-yl)methyl)-2,2-dimethylchroman-6-sulfonamido)acetic acid $^1$H NMR (500 MHz, CDCl3) δ 7.60-7.56 (m, 2H), 7.42-7.37 (m, 1H), 7.36-7.35 (m, 1H), 7.35-7.31 (m, 2H), 7.12-7.08 (m, 1H), 7.07 (s, 1H), 6.94 (d, J=9.0 Hz, 1H), 6.83 (d, J=8.3 Hz, 1H), 4.50 (s, 2H), 3.98 (s, 2H), 2.78 (t, J=6.7 Hz, 2H), 1.80 (t, J=6.7 Hz, 2H), 1.33 (s, 6H). LRMS [ESI, MH$^+$] m/z calcd for C27H26F4NO6S 568.14, found 568.2.

Example 66

2-(N-((5-fluoro-3'-(trifluoromethoxy)biphenyl-3-yl)methyl)-2,2-dimethylchroman-6-sulfonamido)acetic acid $^1$H NMR (500 MHz, CDCl3) δ 7.61-7.56 (m, 2H), 7.45 (dd, J=10.0, 5.7 Hz, 1H), 7.41 (dd, J=6.5, 1.3 Hz, 1H), 7.33 (s, 1H), 7.22 (d, J=7.8 Hz, 1H), 7.20 (s, 1H), 7.17 (dd, J=9.4, 1.9 Hz, 1H), 6.95 (d, J=8.9 Hz, 1H), 6.86-6.82 (m, 1H), 4.51 (s, 2H), 3.98 (s, 2H), 2.78 (t, J=6.7 Hz, 2H), 1.80 (t, J=6.7 Hz, 2H), 1.33 (s, 6H). LRMS [ESI, MH$^+$] m/z calcd for C27H26F4NO6S 568.14, found 568.2.

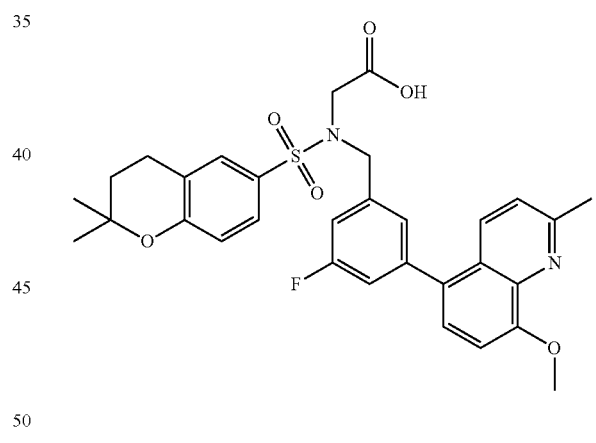

Example 68

2-(N-(3-fluoro-5-(8-methoxy-2-methylquinolin-5-yl)benzyl)-2,2-dimethylchroman-6-sulfonamido)acetic acid $^1$H NMR (500 MHz, CDCl3) δ 8.56 (d, J=8.7 Hz, 1H), 7.58 (s, 1H), 7.55 (dd, J=14.6, 5.6 Hz, 3H), 7.26-7.23 (m, 1H), 7.19 (s, 1H), 7.02 (d, J=8.3 Hz, 1H), 6.98 (d, J=8.4 Hz, 1H), 6.82 (d, J=8.6 Hz, 1H), 4.40 (s, 2H), 4.08 (s, 3H), 3.89 (s, 2H), 2.95 (s, 3H), 2.78 (t, J=6.5 Hz, 2H), 1.81 (t, J=6.7 Hz, 2H), 1.34 (s, 6H). LRMS [ESI, MH$^+$] m/z calcd for C31H32FN2O6S 579.2, found 579.3.

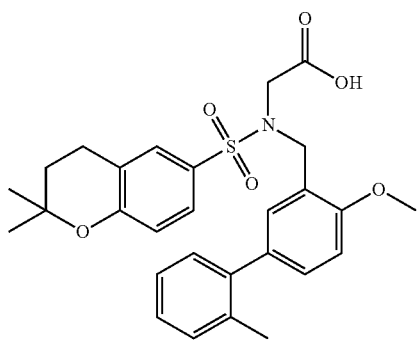

Example 69

2-(N-((4-methoxy-2'-methylbiphenyl-3-yl)methyl)-2,2-dimethylchroman-6-sulfonamido)acetic acid $^1$H NMR (500 MHz, CDCl3) δ 7.55-7.50 (m, 2H), 7.25-7.18 (m, 4H), 7.17 (d, J=2.2 Hz, 1H), 7.15-7.10 (m, 1H), 6.86 (d, J=8.4 Hz, 1H), 6.81-6.77 (m, 1H), 4.50 (s, 2H), 4.00 (s, 2H), 3.77 (s, 3H), 2.73 (t, J=6.7 Hz, 2H), 2.23 (s, 3H), 1.77 (t, J=6.7 Hz, 2H), 1.32 (s, 6H). LRMS [ESI, MH$^+$] m/z calcd for C28H32NO6S 510.2, found 510.3.

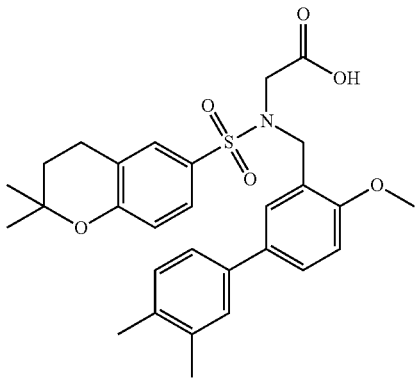

Example 71

2-(N-((4-methoxy-3',4'-dimethylbiphenyl-3-yl)methyl)-2,2-dimethylchroman-6-sulfonamido)acetic acid $^1$H NMR (500 MHz, CDCl3) δ 7.55 (dd, J=8.6, 2.3 Hz, 1H), 7.50 (d, J=2.2 Hz, 1H), 7.46 (dd, J=8.5, 2.3 Hz, 1H), 7.37 (d, J=2.3 Hz, 1H), 7.25 (d, J=1.2 Hz, 1H), 7.21-7.17 (m, 1H), 7.15 (d, J=7.8 Hz, 1H), 6.85 (d, J=8.5 Hz, 1H), 6.81 (d, J=8.6 Hz, 1H), 4.52 (s, 2H), 4.00 (s, 2H), 3.76 (s, 3H), 2.70 (t, J=6.7 Hz, 2H), 2.31 (s, 3H), 2.28 (s, 3H), 1.75 (t, J=6.7 Hz, 2H), 1.31 (s, 6H). LRMS [ESI, MH$^+$] m/z calcd for C29H34NO6S 524.21, found 524.3.

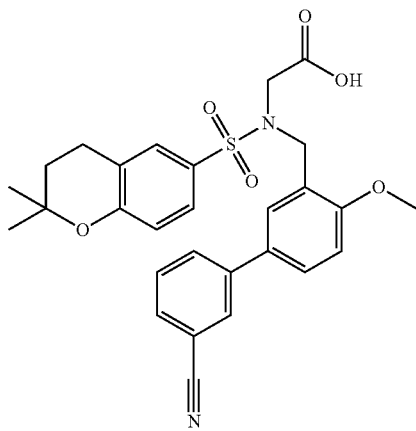

Example 70

2-(N-((3'-cyano-4-methoxybiphenyl-3-yl)methyl)-2,2-dimethylchroman-6-sulfonamido)acetic acid $^1$H NMR (500 MHz, CDCl3) δ 7.75 (d, J=1.5 Hz, 1H), 7.71-7.67 (m, 1H), 7.57 (dd, J=7.7, 1.3 Hz, 1H), 7.54 (dd, J=8.6, 2.3 Hz, 1H), 7.52-7.48 (m, 2H), 7.45 (dq, J=4.8, 2.4 Hz, 2H), 6.92-6.87 (m, 1H), 6.81 (d, J=8.6 Hz, 1H), 4.52 (s, 2H), 4.03 (s, 2H), 3.78 (s, 3H), 2.72 (t, J=6.7 Hz, 2H), 1.76 (t, J=6.7 Hz, 2H), 1.31 (s, 6H). LRMS [ESI, MH$^+$] m/z calcd for C28H29N2O6S 521.17, found 521.2.

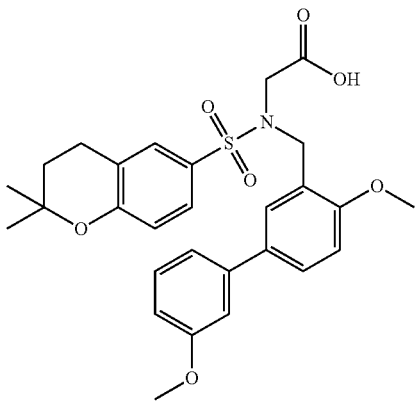

Example 72

2-(N-((3',4-dimethoxybiphenyl-3-yl)methyl)-2,2-dimethylchroman-6-sulfonamido)acetic acid $^1$H NMR (500 MHz, CDCl3) δ 7.54 (dd, J=8.6, 2.3 Hz, 1H), 7.50 (d, J=2.1 Hz, 1H), 7.47 (dd, J=8.5, 2.3 Hz, 1H), 7.41 (d, J=2.3 Hz, 1H), 7.31 (t, J=7.9 Hz, 1H), 7.06-7.03 (m, 1H), 7.03-7.00 (m, 1H), 6.88-6.83 (m, 2H), 6.80 (d, J=8.6 Hz, 1H), 4.52 (s, 2H), 4.02 (s, 2H), 3.85 (s, 3H), 3.76 (s, 3H), 2.70 (t, J=6.7 Hz, 2H), 1.75 (t, J=6.7 Hz, 2H), 1.31 (s, 6H). LRMS [ESI, MH$^+$] m/z calcd for C28H32NO7S 526.19, found 526.3.

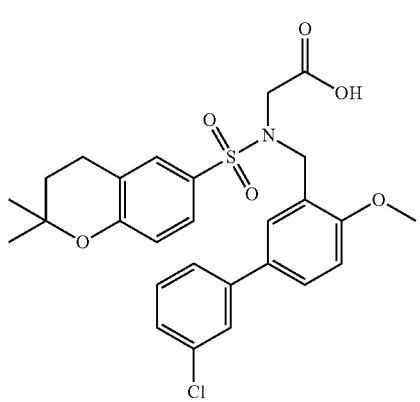

Example 73

2-(N-((3'-chloro-4-methoxybiphenyl-3-yl)methyl)-2,
2-dimethylchroman-6-sulfonamido)acetic acid $^1$H NMR (500 MHz, CDCl3) δ 7.54 (dd, J=8.6, 2.4 Hz, 1H), 7.51 (d, J=2.3 Hz, 1H), 7.46-7.42 (m, 2H), 7.38 (d, J=2.3 Hz, 1H), 7.35-7.30 (m, 2H), 7.27-7.24 (m, 1H), 6.87 (d, J=8.5 Hz, 1H), 6.80 (d, J=8.6 Hz, 1H), 4.53 (s, 2H), 4.03 (s, 2H), 3.77 (s, 3H), 2.70 (t, J=6.7 Hz, 2H), 1.75 (t, J=6.7 Hz, 2H), 1.31 (s, 6H). LRMS [ESI, MH$^+$] m/z calcd for C27H29ClNO6S 530.14, found 530.2.

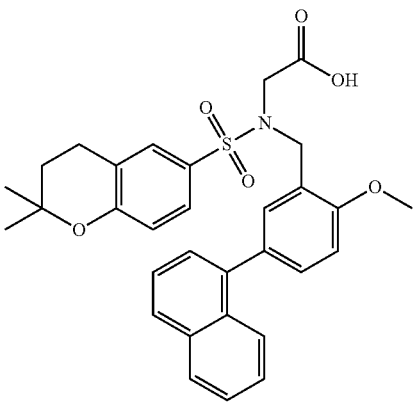

Example 75

2-(N-(2-methoxy-5-(naphthalen-1-yl)benzyl)-2,2-dimethylchroman-6-sulfonamido)acetic acid $^1$H NMR (500 MHz, CDCl3) δ 7.88 (d, J=8.1 Hz, 1H), 7.83 (t, J=8.5 Hz, 2H), 7.54-7.51 (m, 2H), 7.50 (d, J=7.0 Hz, 1H), 7.48-7.45 (m, 1H), 7.45-7.41 (m, 1H), 7.40 (dd, J=8.4, 2.2 Hz, 1H), 7.33-7.30 (m, 1H), 7.29 (d, J=2.1 Hz, 1H), 6.93 (d, J=8.4 Hz, 1H), 6.76 (d, J=8.3 Hz, 1H), 4.53 (s, 2H), 4.03 (s, 2H), 3.81 (s, 3H), 2.65 (t, J=6.7 Hz, 2H), 1.69 (t, J=6.7 Hz, 2H), 1.28 (s, 6H). LRMS [ESI, MH$^+$] m/z calcd for C31H32NO6S 546.2, found 546.3.

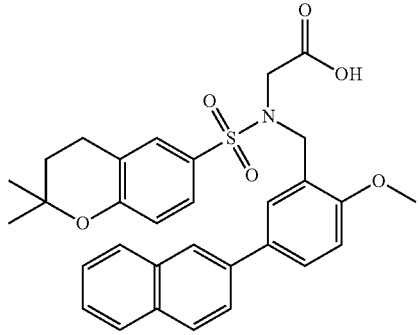

Example 74

2-(N-(2-methoxy-5-(naphthalen-2-yl)benzyl)-2,2-dimethylchroman-6-sulfonamido)acetic acid $^1$H NMR (500 MHz, CDCl3) δ 7.90 (s, 1H), 7.89-7.85 (m, 2H), 7.83 (d, J=7.9 Hz, 1H), 7.61 (ddd, J=8.4, 3.9, 2.1 Hz, 2H), 7.57 (dd, J=8.6, 2.4 Hz, 1H), 7.52 (dd, J=5.4, 2.3 Hz, 2H), 7.51-7.43 (m, 2H), 6.91 (d, J=8.5 Hz, 1H), 6.83 (d, J=8.6 Hz, 1H), 4.57 (s, 2H), 4.03 (s, 2H), 3.79 (s, 3H), 2.68 (t, J=6.7 Hz, 2H), 1.68 (t, J=6.7 Hz, 2H), 1.27 (s, 6H). LRMS [ESI, MH$^+$] m/z calcd for C31H32NO6S 546.2, found 546.2.

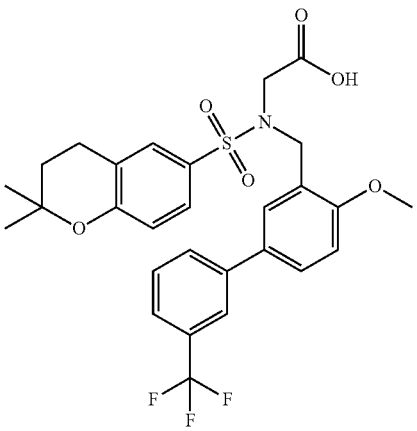

Example 76

2-(N-((4-methoxy-3'-(trifluoromethyl)biphenyl-3-yl)methyl)-2,2-dimethylchroman-6-sulfonamido)acetic acid $^1$H NMR (500 MHz, CDCl3) δ 7.72 (s, 1H), 7.64 (d, J=7.5 Hz, 1H), 7.56-7.46 (m, 5H), 7.44 (d, J=2.3 Hz, 1H), 6.89 (d, J=8.5 Hz, 1H), 6.80 (d, J=8.6 Hz, 1H), 4.53 (s, 2H), 3.78 (s, 3H), 2.70 (t, J=6.7 Hz, 2H), 1.75 (t, J=6.7 Hz, 2H), 1.30 (s, 6H). LRMS [ESI, MH$^+$] m/z calcd for C28H29F3NO6S 564.17, found 564.2.

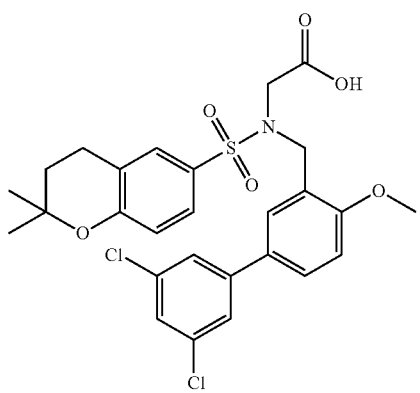

Example 77

2-(N-((3',5'-dichloro-4-methoxybiphenyl-3-yl)methyl)-2,2-dimethylchroman-6-sulfonamido)acetic acid $^1$H NMR (500 MHz, CDCl3) δ 7.54 (dd, J=8.6, 2.3 Hz, 1H), 7.51 (d, J=2.2 Hz, 1H), 7.42 (dd, J=8.5, 2.4 Hz, 1H), 7.37 (d, J=2.4 Hz, 1H), 7.33 (d, J=1.8 Hz, 2H), 7.28 (t, J=1.8 Hz, 1H), 6.87 (d, J=8.6 Hz, 1H), 6.81 (d, J=8.6 Hz, 1H), 4.52 (s, 3H), 4.02 (s, 2H), 3.78 (s, 3H), 2.71 (t, J=6.7 Hz, 2H), 1.76 (t, J=6.7 Hz, 2H), 1.31 (s, 6H). LRMS [ESI, MH$^+$] m/z calcd for C27H28Cl2NO6S 564.1, found 564.2.

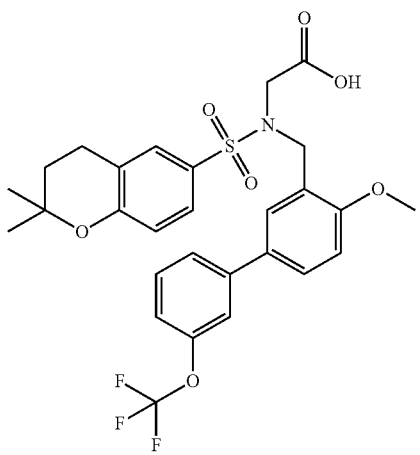

Example 79

2-(N-((4-methoxy-3'-(trifluoromethoxy)biphenyl-3-yl)methyl)-2,2-dimethylchroman-6-sulfonamido) acetic acid $^1$H NMR (500 MHz, CDCl3) δ 7.54 (dd, J=8.6, 2.3 Hz, 1H), 7.51 (d, J=2.1 Hz, 1H), 7.46 (dd, J=8.5, 2.4 Hz, 1H), 7.43-7.37 (m, 3H), 7.32 (s, 1H), 7.15 (d, J=7.5 Hz, 1H), 6.88 (d, J=8.5 Hz, 1H), 6.80 (d, J=8.6 Hz, 1H), 4.52 (s, 2H), 4.02 (s, 2H), 3.78 (s, 3H), 2.71 (t, J=6.7 Hz, 2H), 1.75 (t, J=6.7 Hz, 2H), 1.31 (s, 6H). LRMS [ESI, MH$^+$] m/z calcd for C28H29F3NO7S 580.16, found 580.2.

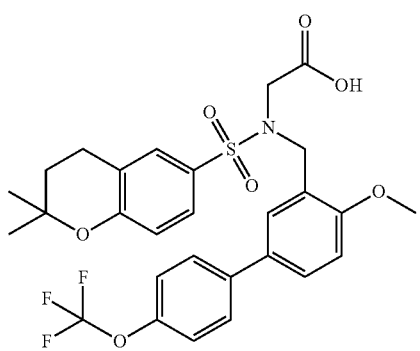

Example 78

2-(N-((4-methoxy-4'-(trifluoromethoxy)biphenyl-3-yl)methyl)-2,2-dimethylchroman-6-sulfonamido) acetic acid $^1$H NMR (500 MHz, CDCl3) δ 7.55 (dd, J=8.6, 2.4 Hz, 1H), 7.52 (d, J=2.1 Hz, 1H), 7.48-7.46 (m, 1H), 7.46-7.42 (m, 2H), 7.38 (d, J=2.3 Hz, 1H), 7.24 (d, J=8.1 Hz, 2H), 6.87 (d, J=8.5 Hz, 1H), 6.81 (d, J=8.6 Hz, 1H), 4.53 (s, 2H), 4.02 (s, 2H), 3.77 (s, 3H), 2.71 (t, J=6.7 Hz, 2H), 1.76 (t, J=6.7 Hz, 2H), 1.32 (s, 6H). LRMS [ESI, MH$^+$] m/z calcd for C28H29F3NO7S 580.16, found 580.2.

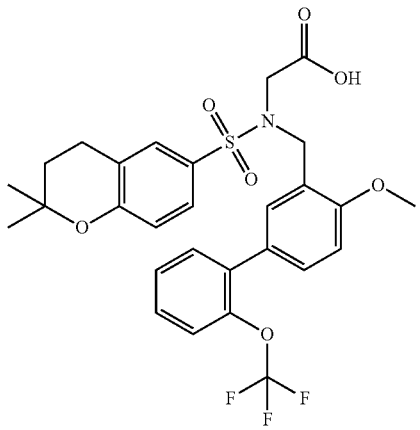

Example 80

2-(N-((4-methoxy-2'-(trifluoromethoxy)biphenyl-3-yl)methyl)-2,2-dimethylchroman-6-sulfonamido) acetic acid $^1$H NMR (500 MHz, CDCl3) δ 7.55-7.51 (m, 2H), 7.38 (dd, J=8.5, 2.3 Hz, 1H), 7.35-7.29 (m, 4H), 7.28 (d, J=2.2 Hz, 1H), 6.87 (d, J=8.5 Hz, 1H), 6.80-6.77 (m, 1H), 4.52 (s, 2H), 4.00 (s, 2H), 3.77 (s, 3H), 2.72 (t, J=6.7 Hz, 2H), 1.76 (t, J=6.7 Hz, 2H), 1.31 (s, 6H). LRMS [ESI, MH$^+$] m/z calcd for C28H29F3NO7S 580.16, found 580.2.

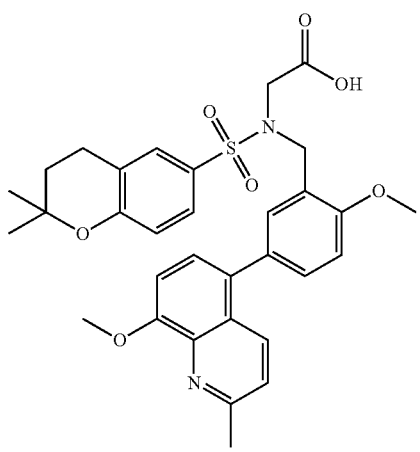

Example 81

2-(N-(2-methoxy-5-(8-methoxy-2-methylquinolin-5-yl)benzyl)-2,2-dimethylchroman-6-sulfonamido) acetic acid $^1$H NMR (500 MHz, CDCl3) δ 8.68 (d, J=8.8 Hz, 1H), 7.56 (d, J=8.8 Hz, 1H), 7.52 (s, 1H), 7.52-7.46 (m, 3H), 7.23-7.20 (m, 2H), 6.91 (d, J=8.5 Hz, 1H), 6.76 (d, J=8.6 Hz, 1H), 4.39 (s, 2H), 4.02 (s, 3H), 3.92 (s, 2H), 3.78 (s, 3H), 2.91 (s, 3H), 2.73 (t, J=6.6 Hz, 2H), 1.76 (t, J=6.7 Hz, 2H), 1.31 (s, 6H). LRMS [ESI, MH$^+$] m/z calcd for C32H35N2O7S 591.22, found 591.3.

Biological Methods

Plates

Black non-binding surface Corning plates (3655) were spotted with 0.9 μL of compound in twenty point 1:3 dilutions. The same volume of dimethyl sulfoxide (DMSO) was added to column 23 of the plate. In column 24, 0.9 μL of 2-(N-(4-cyclohexylphenyl)-2,2-dimethylchroman-6-sulfonamido)acetic acid was manually added as a blank to normalize the data.

Enzyme

A membrane prep from a stable HEK cell line expressing LG586 was prepared by the Cell Resource Group at BMS in Hopewell, N.J. The protein concentration of the membrane prep was 1.28 μg/μL. These stocks were kept at −80° C. in 1 mL aliquots. For the assay, membrane was thawed to room temperature and then added to the assay buffer, 100 mM HEPES in MQ water at pH 7.5. The concentration of the LG586 enzyme in the assay is 0.005 μg/mL.

Substrate

The substrate used in this assay was purchased from Sigma (N9876) p-nitrophenyl butyrate (PNP). The substrate is received in the liquid form and must be diluted with DMSO. Stocks were kept in −20° C. at 1M concentrations. The final concentration of the substrate is 250 μM.

Assay

Enzyme was added to the plates 80 μL/well using a Multidrop Combi (Thermo). The plates were incubated with the compound for 10 minutes at room temperature. Then 9 μL of substrate was added to each well and the plates were immediately read on the Viewlux Imager (Perkin Elmer) in absorbance mode with the excitation filter of 405 nm and emission filter of 564/250 nm. The read was kinetic, plates were read once every 30 seconds for 5 minutes and then slopes were calculated for each well and the data was reduced with in-house software.

TABLE 1

| Example Number | Structure | Data Range* | LE_LG586PNP_DR (IC50, uM) |
|---|---|---|---|
| 1 | 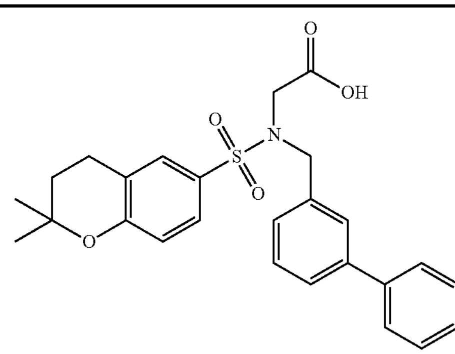 | | A |
| 2 | 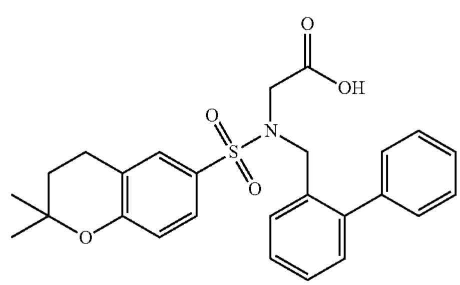 [SMILES: CC1(C)CCc2cc(S(=O)(=O)N(CC(=O)O)Cc3ccccc3-c3ccccc3)ccc2O1] | | B |

TABLE 1-continued
| Example Number | Structure | Data Range* | LE_LG5 86PNP_DR (IC50, uM) |
|---|---|---|---|
| 3 | 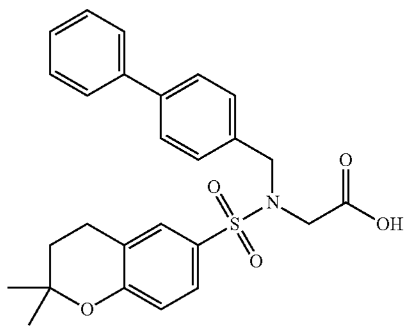 [SMILES: CC1(C)CCc2cc(S(=O)(=O)N(CC(=O)O)Cc3ccc(-c4ccccc4)cc3)ccc2O1] | | |
| 4 | 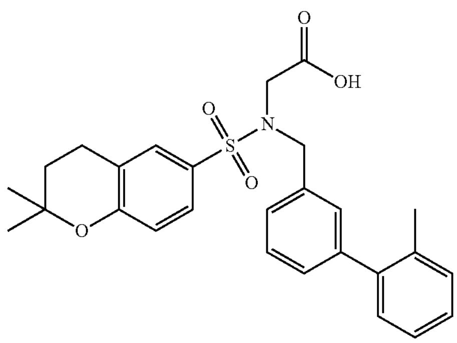 [SMILES: Cc1ccccc1-c1cccc(CN(CC(=O)O)S(=O)(=O)c2ccc3c(c2)CCC(C)(C)O3)c1] | A | 0.034 |
| 5 | 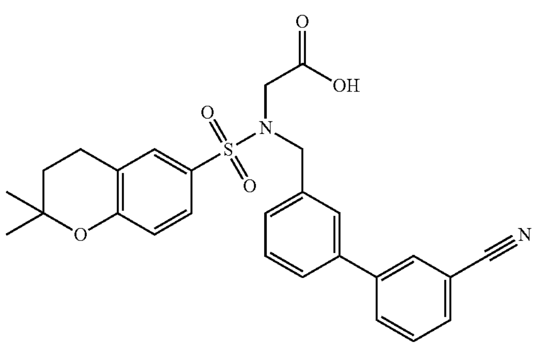 [SMILES: CC1(C)CCc2cc(S(=O)(=O)N(CC(=O)O)Cc3cccc(-c4cccc(C#N)c4)c3)ccc2O1] | B | |
| 6 | 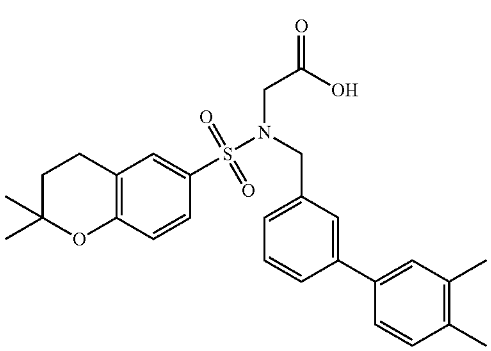 | A | |
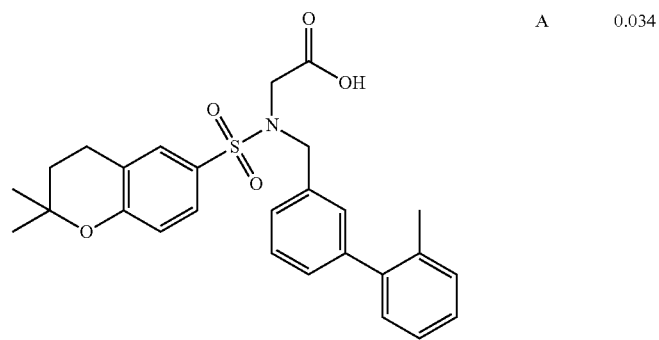
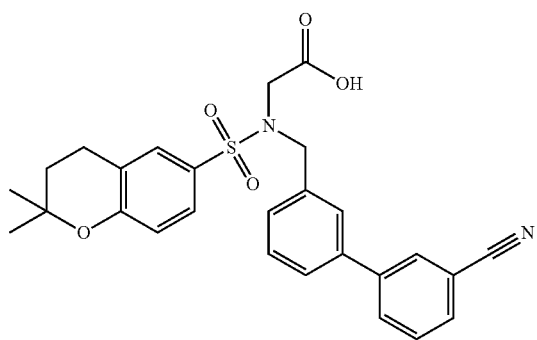
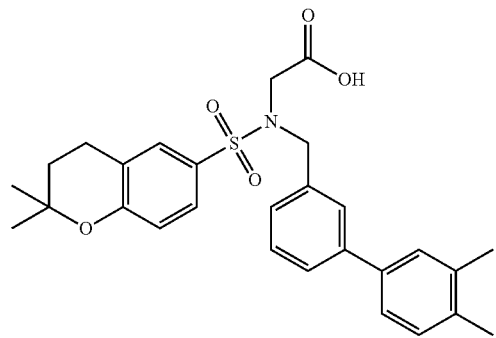

TABLE 1-continued

| Example Number | Structure | Data Range* | LE_LG5 86PNP_DR (IC50, uM) |
|---|---|---|---|
| 7 | 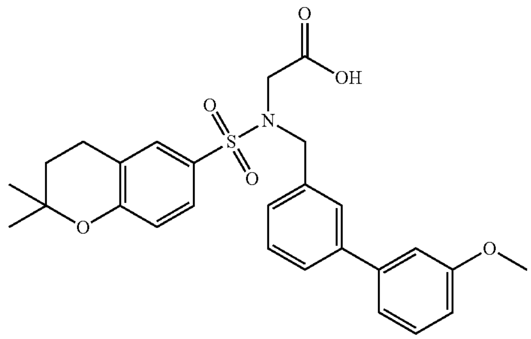 | A | |
| 8 | 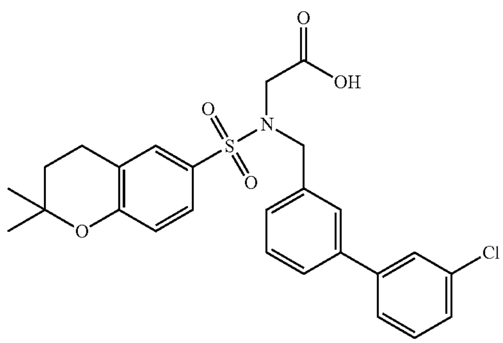 [SMILES: CC1(C)CCc2cc(S(=O)(=O)N(CC(=O)O)Cc3cccc(-c4cccc(Cl)c4)c3)ccc2O1] | A | |
| 9 | 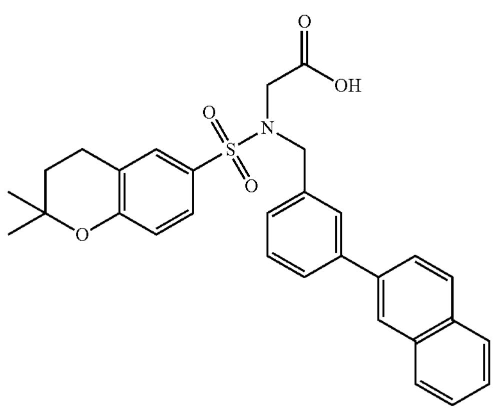 [SMILES: CC1(C)CCc2cc(S(=O)(=O)N(CC(=O)O)Cc3cccc(-c4ccc5ccccc5c4)c3)ccc2O1] | A | |
| 10 | 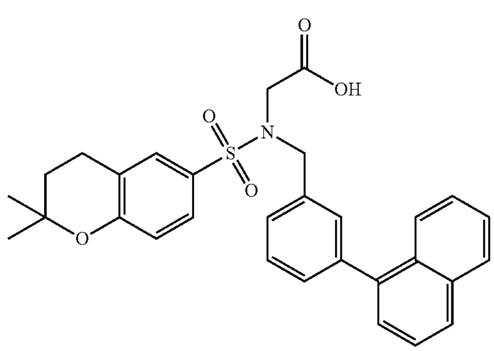 [SMILES: CC1(C)CCc2cc(S(=O)(=O)N(CC(=O)O)Cc3cccc(-c4cccc5ccccc45)c3)ccc2O1] | A | |

TABLE 1-continued
| Example Number | Structure | Data Range* | LE_LG5 86PNP_DR (IC50, uM) |
|---|---|---|---|
| 11 | 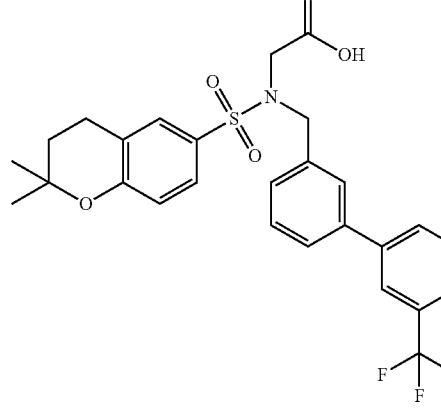 | A | |
| 12 | 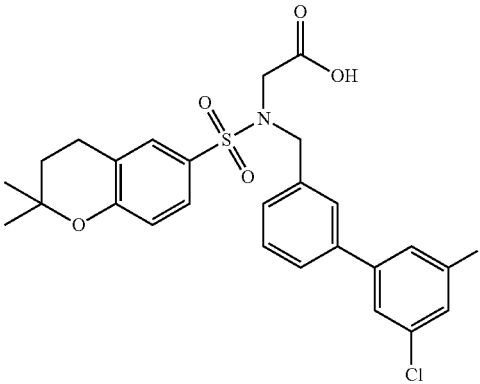 | A | |
| 13 | 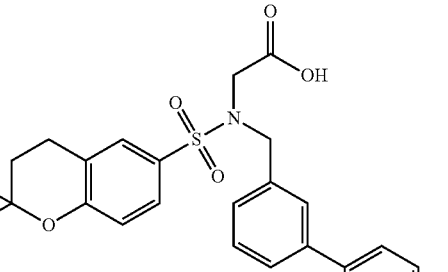 | A | 0.032 |

TABLE 1-continued

| Example Number | Structure | Data Range* | LE_LG5 86PNP_DR (IC50, uM) |
|---|---|---|---|
| 14 | 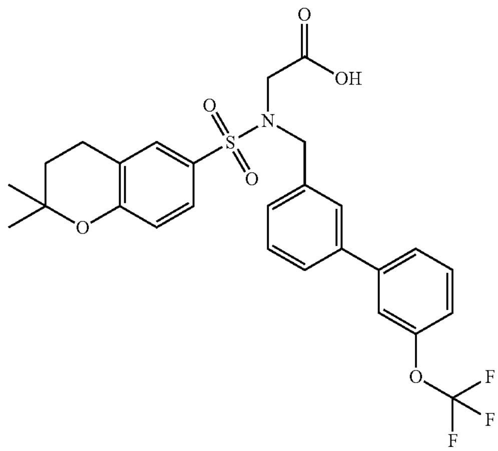 [SMILES: CC1(C)CCc2cc(S(=O)(=O)N(CC(=O)O)Cc3cccc(-c4cccc(OC(F)(F)F)c4)c3)ccc2O1] | A | |
| 15 | 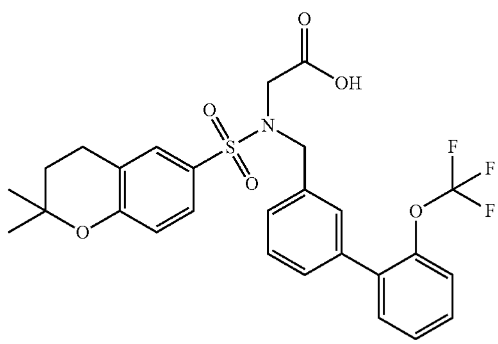 [SMILES: CC1(C)CCc2cc(S(=O)(=O)N(CC(=O)O)Cc3cccc(-c4ccccc4OC(F)(F)F)c3)ccc2O1] | A | |
| 16 | 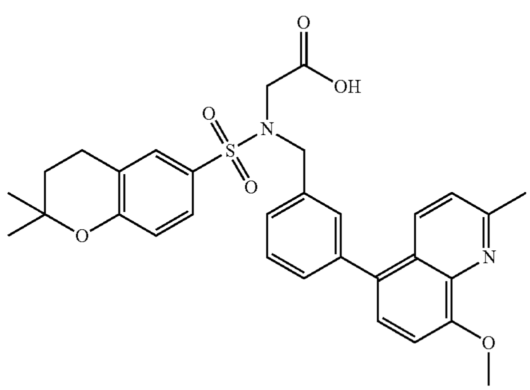 | C | |
| 17 | 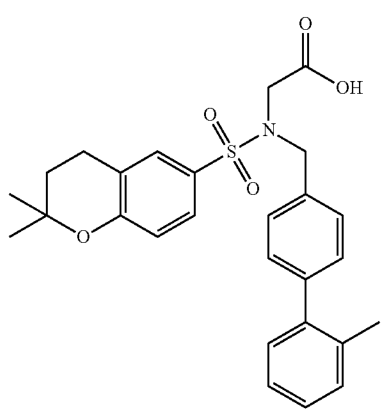 | A | |

TABLE 1-continued
| Example Number | Structure | Data Range* | LE_LG5 86PNP_DR (IC50, uM) |
|---|---|---|---|
| 18 | 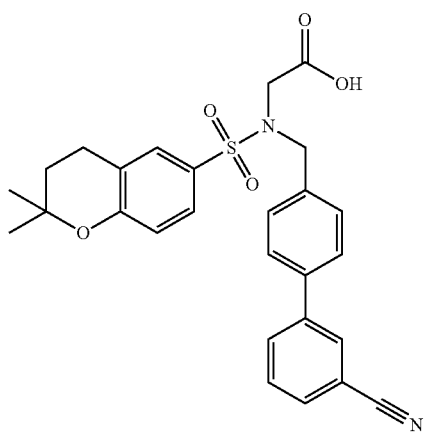 [SMILES: CC1(C)CCc2cc(S(=O)(=O)N(CC(=O)O)Cc3ccc(-c4cccc(C#N)c4)cc3)ccc2O1] | | A |
| 19 | 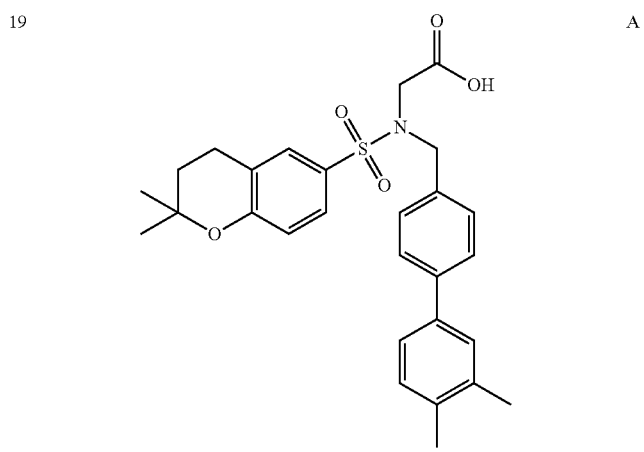 | | A |
| 20 | 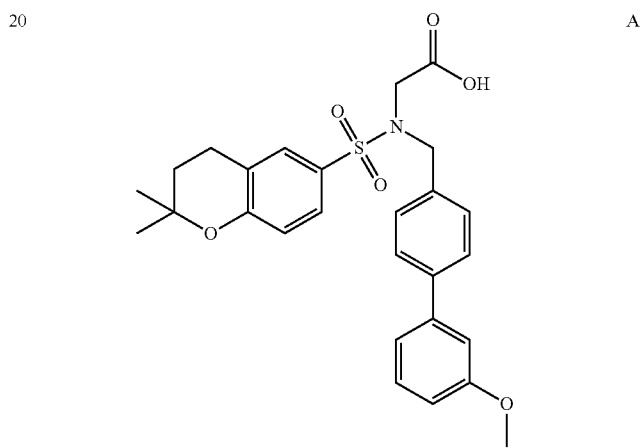 | | A |

TABLE 1-continued
| Example Number | Structure | Data Range* | LE_LG5 86PNP_DR (IC50, uM) |
|---|---|---|---|
| 21 | 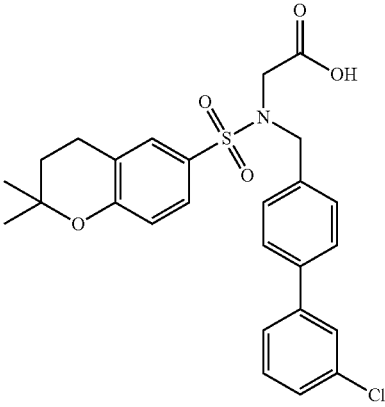 [SMILES: CC1(C)CCc2cc(S(=O)(=O)N(CC(=O)O)Cc3ccc(-c4cccc(Cl)c4)cc3)ccc2O1] | A | |
| 22 | 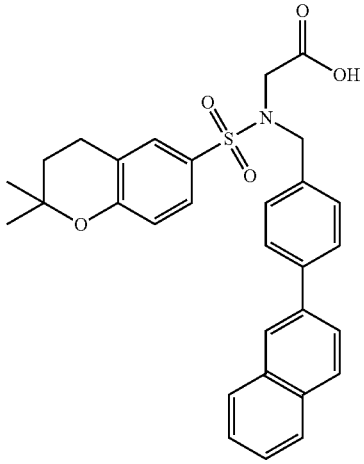 | A | |
| 23 | 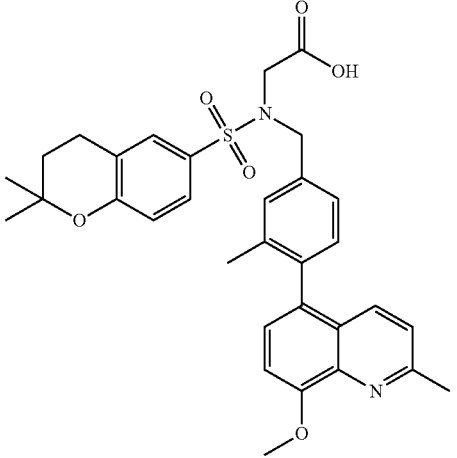 | A | 0.003 |

TABLE 1-continued
| Example Number | Structure | Data Range* | LE_LG5 86PNP_DR (IC50, uM) |
|---|---|---|---|
| 24 | 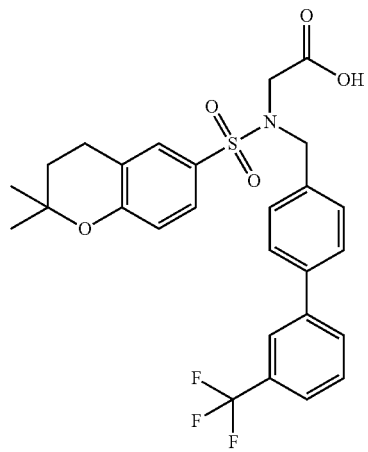 | A | |
| 25 | 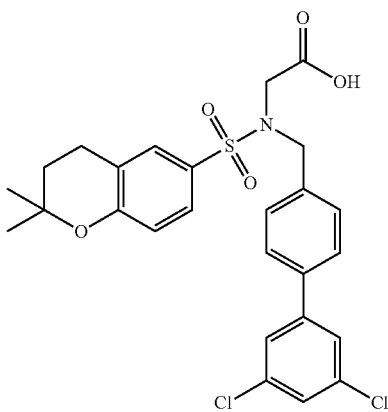 | A | |
| 26 | 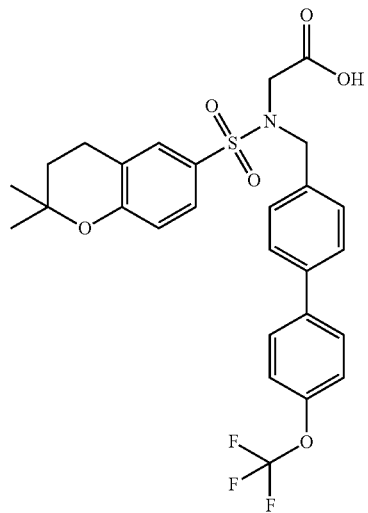 | A | |

TABLE 1-continued
| Example Number | Structure | Data Range* | LE_LG5 86PNP_DR (IC50, uM) |
|---|---|---|---|
| 27 | 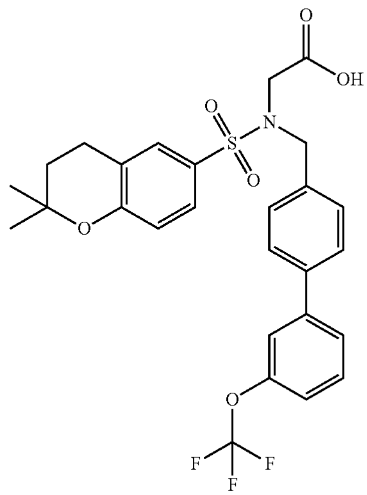 [SMILES: CC1(C)CCc2cc(S(=O)(=O)N(CC(=O)O)Cc3ccc(-c4cccc(OC(F)(F)F)c4)cc3)ccc2O1] | A | |
| 28 | 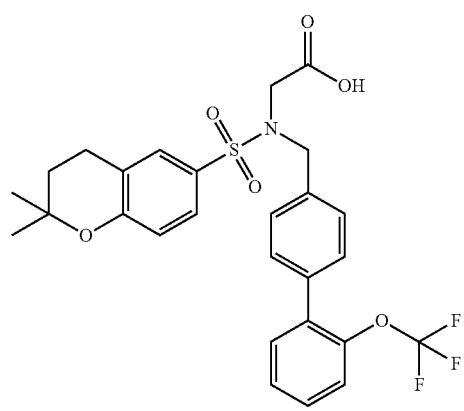 [SMILES: CC1(C)CCc2cc(S(=O)(=O)N(CC(=O)O)Cc3ccc(-c4ccccc4OC(F)(F)F)cc3)ccc2O1] | A | |
| 29 | 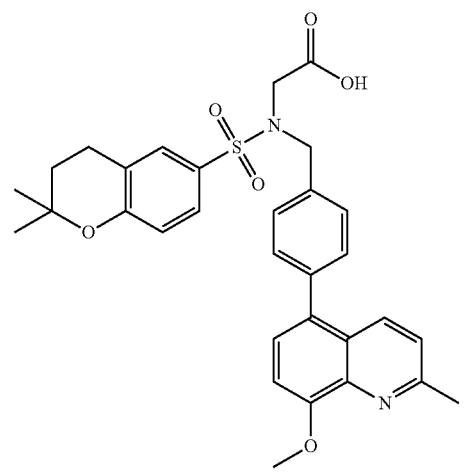 | B | 0.951 |

US 8,354,548 B2
TABLE 1-continued
| Example Number | Structure | Data Range* | LE_LG5 86PNP_DR (IC50, uM) |
|---|---|---|---|
| 30 | 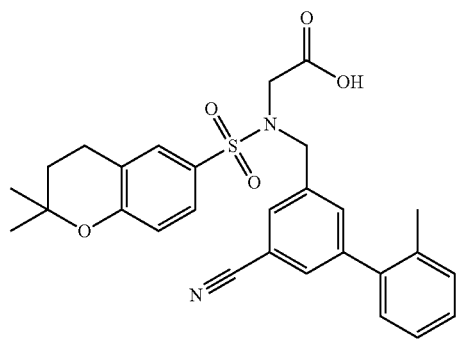 [SMILES: Cc1ccccc1-c1cc(C#N)cc(CN(CC(=O)O)S(=O)(=O)c2ccc3c(c2)CCC(C)(C)O3)c1] | B | |
| 31 | 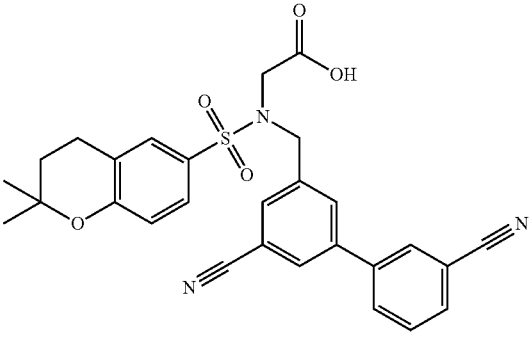 [SMILES: CC1(C)CCc2cc(S(=O)(=O)N(CC(=O)O)Cc3cc(C#N)cc(-c4cccc(C#N)c4)c3)ccc2O1] | B | |
| 32 | 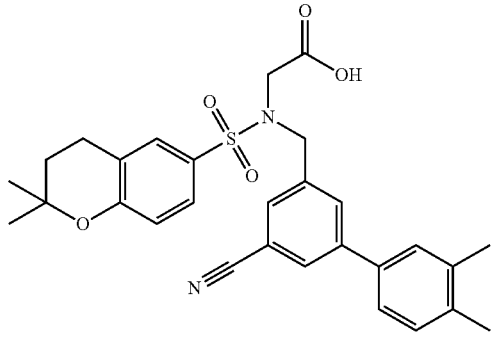 | A | |
| 33 | 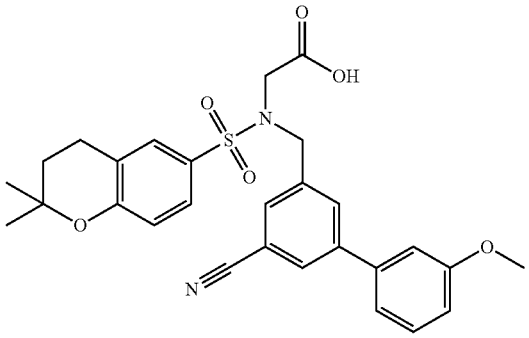 | B | |

TABLE 1-continued

| Example Number | Structure | Data Range* | LE_LG5 86PNP_DR (IC50, uM) |
|---|---|---|---|
| 34 | 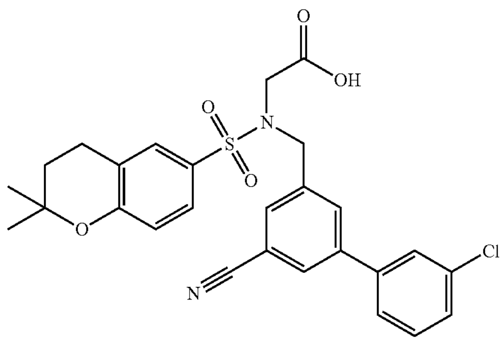 [SMILES: CC1(C)CCc2cc(S(=O)(=O)N(CC(=O)O)Cc3cc(C#N)cc(-c4cccc(Cl)c4)c3)ccc2O1] | A | |
| 35 | 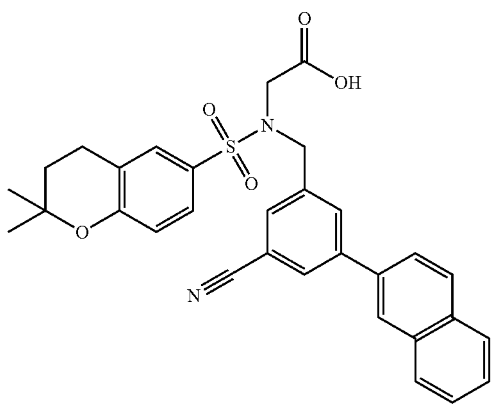 [SMILES: CC1(C)CCc2cc(S(=O)(=O)N(CC(=O)O)Cc3cc(C#N)cc(-c4ccc5ccccc5c4)c3)ccc2O1] | A | |
| 36 | 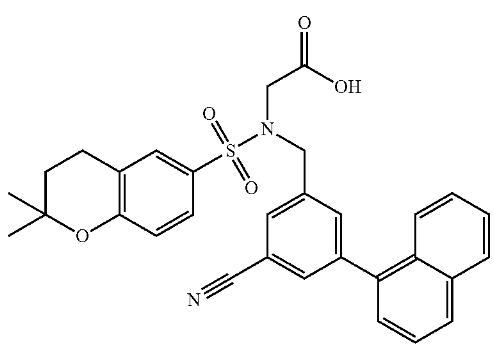 [SMILES: CC1(C)CCc2cc(S(=O)(=O)N(CC(=O)O)Cc3cc(C#N)cc(-c4cccc5ccccc45)c3)ccc2O1] | A | |
| 37 | 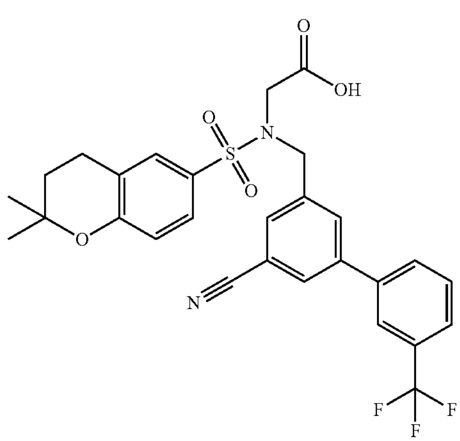 [SMILES: CC1(C)CCc2cc(S(=O)(=O)N(CC(=O)O)Cc3cc(C#N)cc(-c4cccc(C(F)(F)F)c4)c3)ccc2O1] | A | |

TABLE 1-continued
| Example Number | Structure | Data Range* | LE_LG5 86PNP_DR (IC50, uM) |
|---|---|---|---|
| 38 | 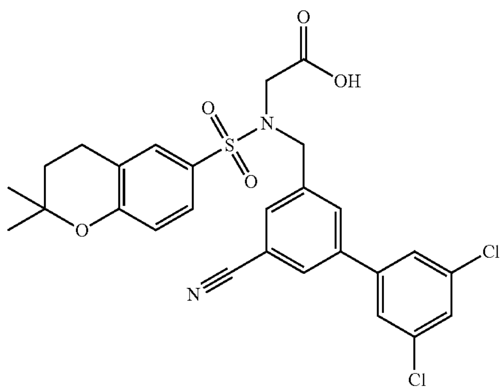 [SMILES: CC1(C)CCc2cc(S(=O)(=O)N(CC(=O)O)Cc3cc(C#N)cc(-c4cc(Cl)cc(Cl)c4)c3)ccc2O1] | A | |
| 39 | 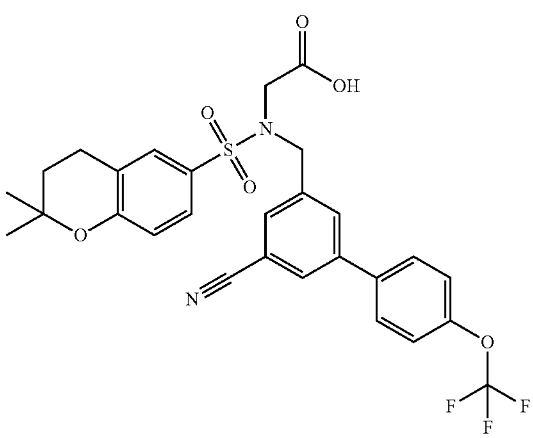 [SMILES: CC1(C)CCc2cc(S(=O)(=O)N(CC(=O)O)Cc3cc(C#N)cc(-c4ccc(OC(F)(F)F)cc4)c3)ccc2O1] | B | 0.133 |
| 40 | 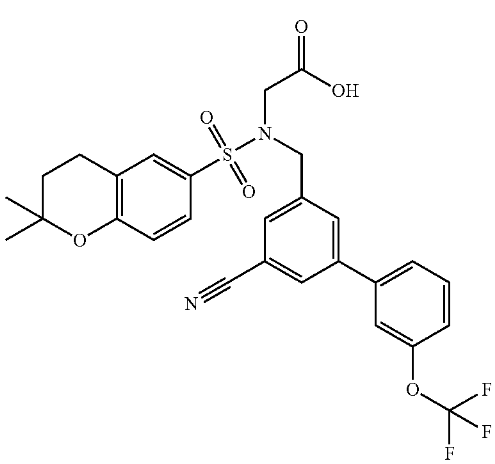 [SMILES: CC1(C)CCc2cc(S(=O)(=O)N(CC(=O)O)Cc3cc(C#N)cc(-c4cccc(OC(F)(F)F)c4)c3)ccc2O1] | A | |
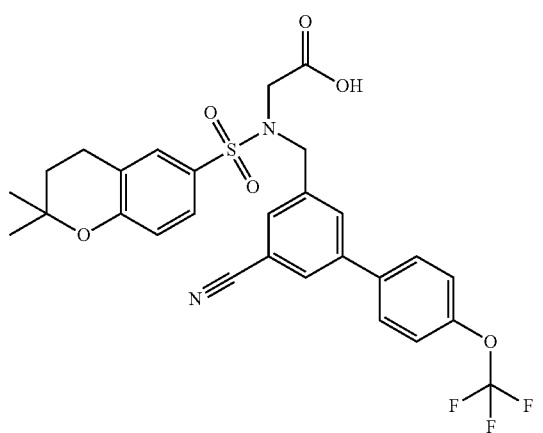
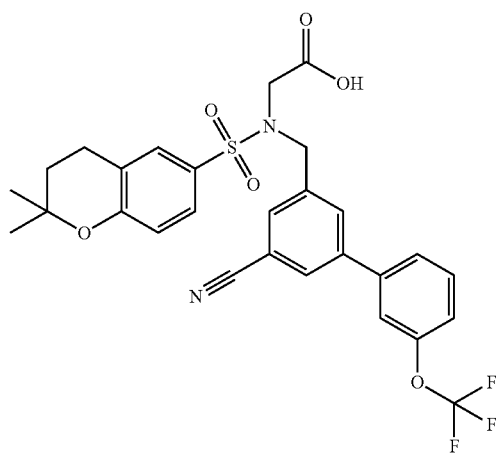

TABLE 1-continued
| Example Number | Structure | Data Range* | LE_LG5 86PNP_DR (IC50, uM) |
|---|---|---|---|
| 41 | 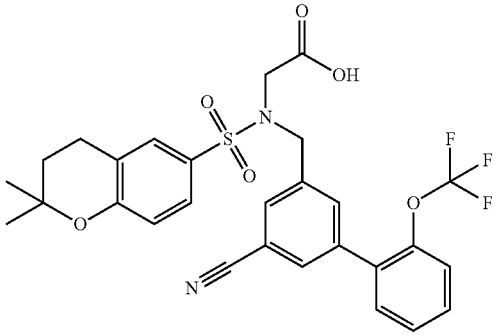 [SMILES: CC1(C)CCc2cc(S(=O)(=O)N(CC(=O)O)Cc3cc(C#N)cc(-c4ccccc4OC(F)(F)F)c3)ccc2O1] | A | |
| 42 | 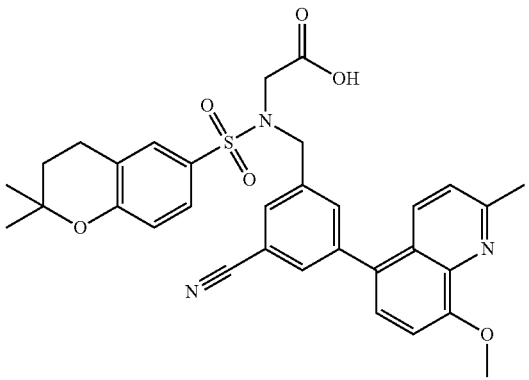 | C | 2.835 |
| 43 | 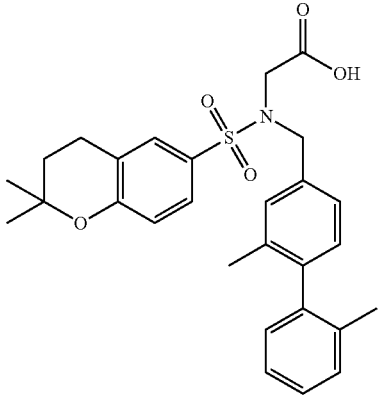 | A | |
| 44 | 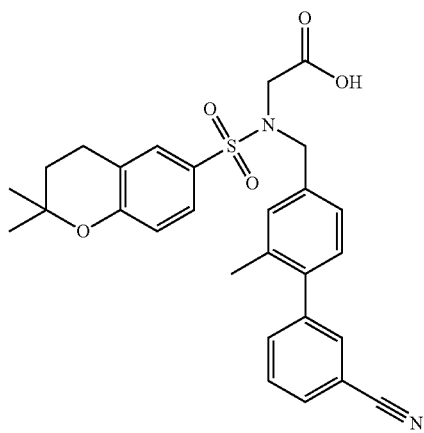 | A | |

TABLE 1-continued
| Example Number | Structure | Data Range* | LE_LG5 86PNP_DR (IC50, uM) |
|---|---|---|---|
| 45 | 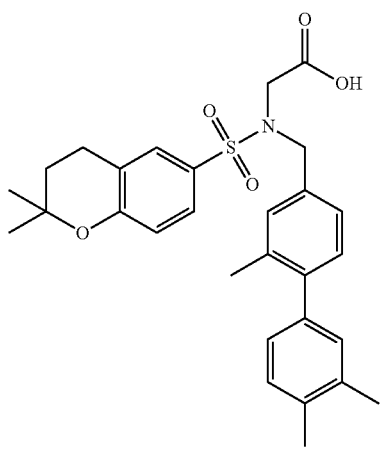 | A | |
| 46 | 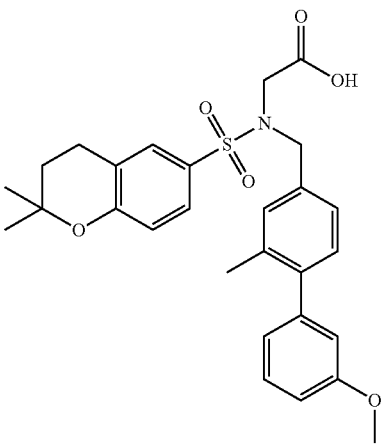 | A | |
| 47 | 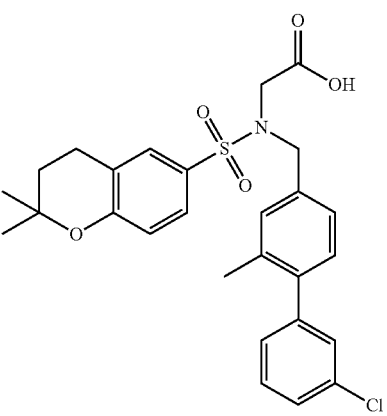 [SMILES: Cc1cc(CN(CC(=O)O)S(=O)(=O)c2ccc3c(c2)CCC(C)(C)O3)ccc1-c1cccc(Cl)c1] | A | |

TABLE 1-continued
| Example Number | Structure | Data Range* | LE_LG5 86PNP_DR (IC50, uM) |
|---|---|---|---|
| 48 | 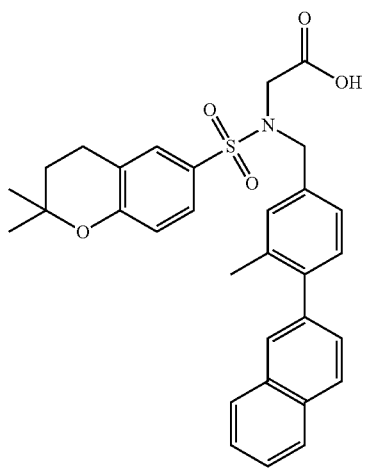 [SMILES: Cc1cc(CN(CC(=O)O)S(=O)(=O)c2ccc3c(c2)CCC(C)(C)O3)ccc1-c1ccc2ccccc2c1] | A | |
| 49 | 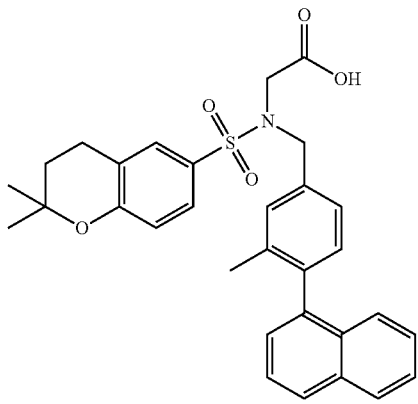 [SMILES: Cc1cc(CN(CC(=O)O)S(=O)(=O)c2ccc3c(c2)CCC(C)(C)O3)ccc1-c1cccc2ccccc12] | A | |
| 50 | 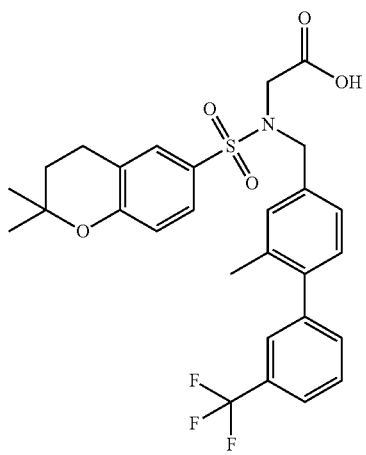 [SMILES: Cc1cc(CN(CC(=O)O)S(=O)(=O)c2ccc3c(c2)CCC(C)(C)O3)ccc1-c1cccc(C(F)(F)F)c1] | A | |

TABLE 1-continued
| Example Number | Structure | Data Range* | LE_LG5 86PNP_DR (IC50, uM) |
|---|---|---|---|
| 51 | 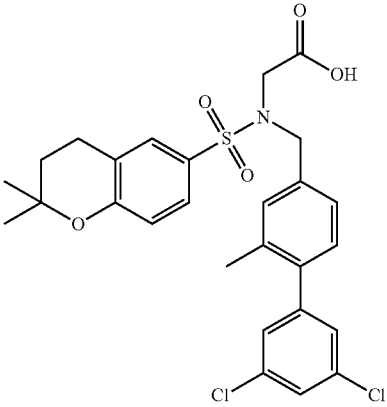 [SMILES: Cc1cc(CN(CC(=O)O)S(=O)(=O)c2ccc3c(c2)CCC(C)(C)O3)ccc1-c1cc(Cl)cc(Cl)c1] | A | |
| 52 | 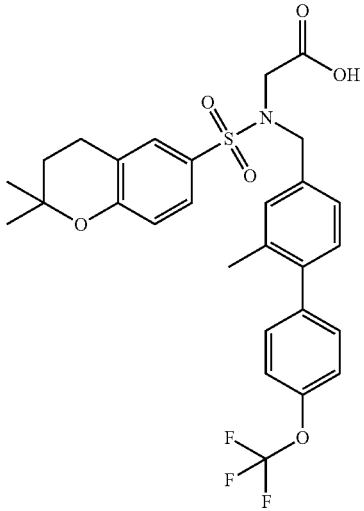 | A | |
| 53 | 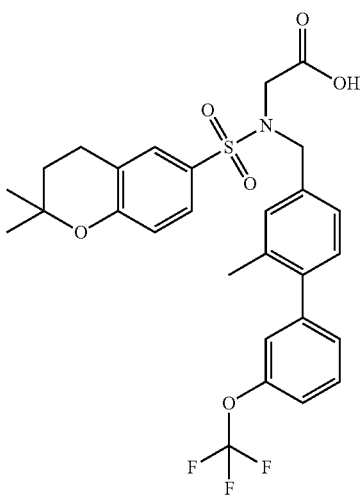 [SMILES: Cc1cc(CN(CC(=O)O)S(=O)(=O)c2ccc3c(c2)CCC(C)(C)O3)ccc1-c1cccc(OC(F)(F)F)c1] | A | |

TABLE 1-continued
| Example Number | Structure | Data Range* | LE_LG5 86PNP_DR (IC50, uM) |
|---|---|---|---|
| 54 | 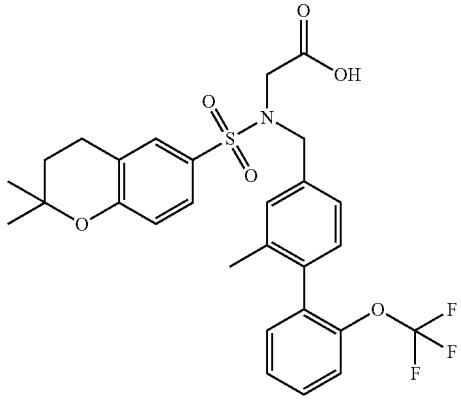 [SMILES: Cc1cc(CN(CC(=O)O)S(=O)(=O)c2ccc3c(c2)CCC(C)(C)O3)ccc1-c1ccccc1OC(F)(F)F] | A | |
| 55 | 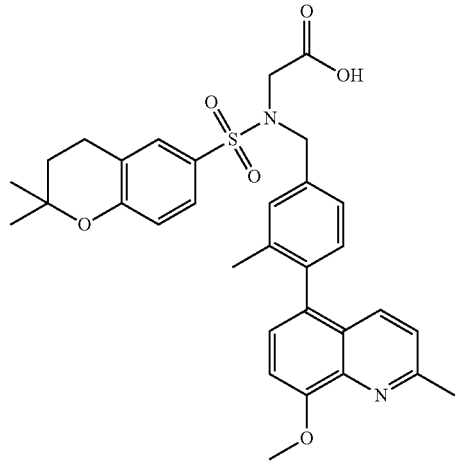 | B | |
| 56 | 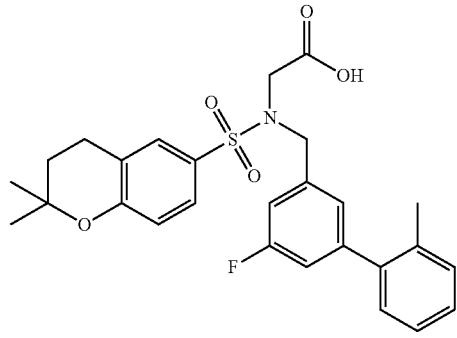 [SMILES: Cc1ccccc1-c1cc(F)cc(CN(CC(=O)O)S(=O)(=O)c2ccc3c(c2)CCC(C)(C)O3)c1] | A | 0.019 |
| 57 | 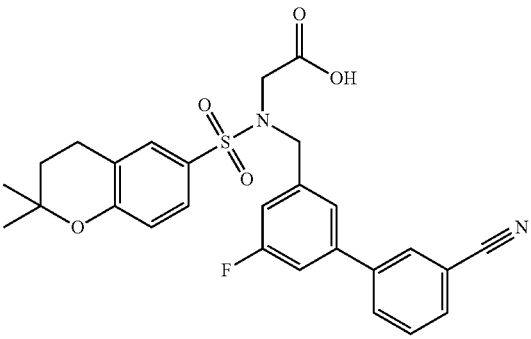 [SMILES: CC1(C)CCc2cc(S(=O)(=O)N(CC(=O)O)Cc3cc(F)cc(-c4cccc(C#N)c4)c3)ccc2O1] | A | 0.101 |

TABLE 1-continued

| Example Number | Structure | Data Range* | LE_LG5 86PNP_DR (IC50, uM) |
|---|---|---|---|
| 58 | 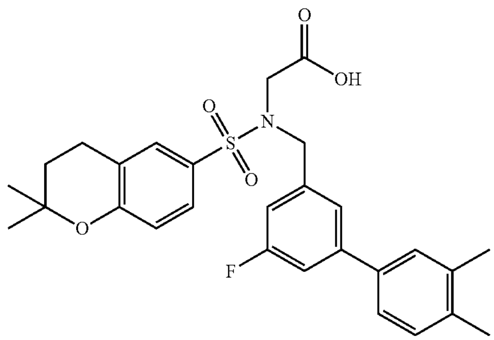 | A | |
| 59 | 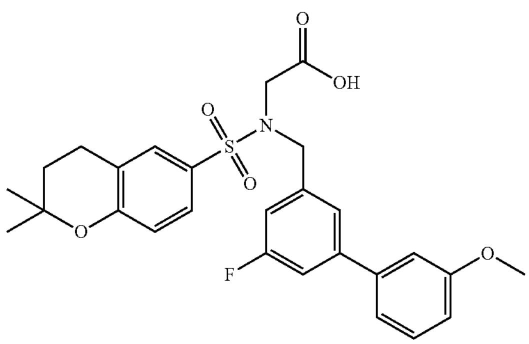 | A | |
| 60 | 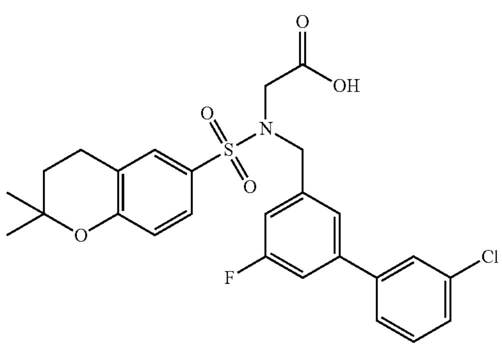 [SMILES: CC1(C)CCc2cc(S(=O)(=O)N(CC(=O)O)Cc3cc(F)cc(-c4cccc(Cl)c4)c3)ccc2O1] | A | |
| 61 | 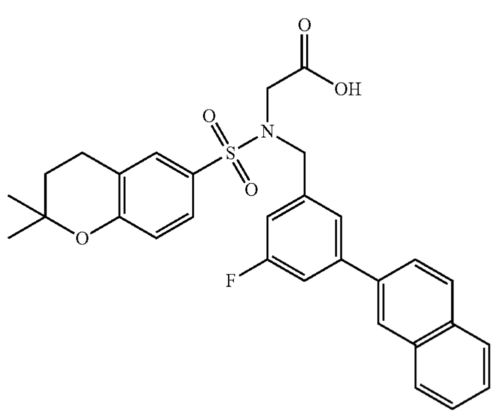 [SMILES: CC1(C)CCc2cc(S(=O)(=O)N(CC(=O)O)Cc3cc(F)cc(-c4ccc5ccccc5c4)c3)ccc2O1] | A | |

TABLE 1-continued

| Example Number | Structure | Data Range* | LE_LG5 86PNP_DR (IC50, uM) |
|---|---|---|---|
| 62 | 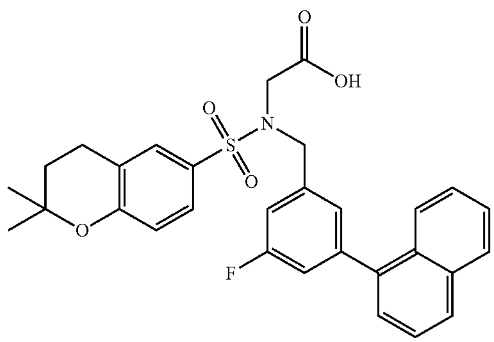 [SMILES: CC1(C)CCc2cc(S(=O)(=O)N(CC(=O)O)Cc3cc(F)cc(-c4cccc5ccccc45)c3)ccc2O1] | A | |
| 63 | 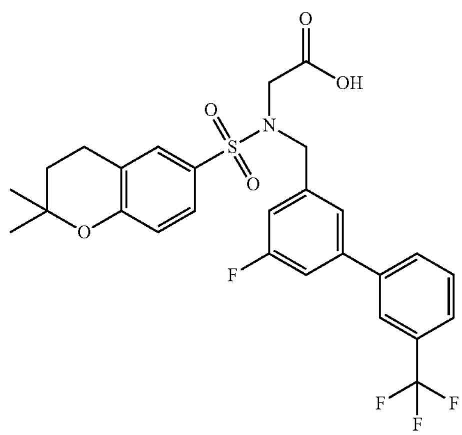 [SMILES: CC1(C)CCc2cc(S(=O)(=O)N(CC(=O)O)Cc3cc(F)cc(-c4cccc(C(F)(F)F)c4)c3)ccc2O1] | A | |
| 64 | 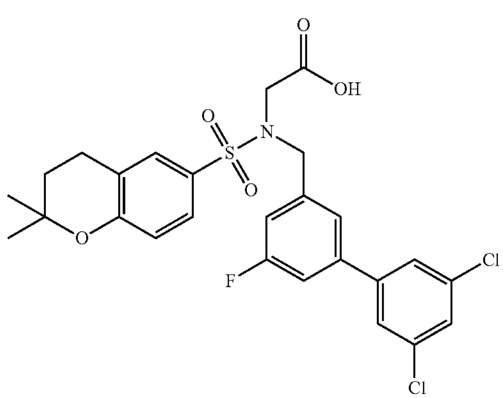 [SMILES: CC1(C)CCc2cc(S(=O)(=O)N(CC(=O)O)Cc3cc(F)cc(-c4cc(Cl)cc(Cl)c4)c3)ccc2O1] | A | |

TABLE 1-continued
| Example Number | Structure | Data Range* | LE_LG5 86PNP_DR (IC50, uM) |
|---|---|---|---|
| 65 | 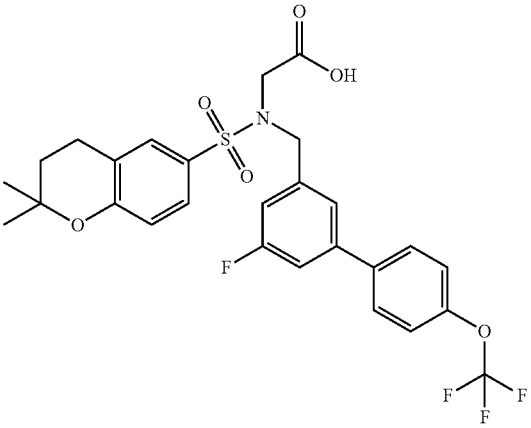 [SMILES: CC1(C)CCc2cc(S(=O)(=O)N(CC(=O)O)Cc3cc(F)cc(-c4ccc(OC(F)(F)F)cc4)c3)ccc2O1] | A | |
| 66 | 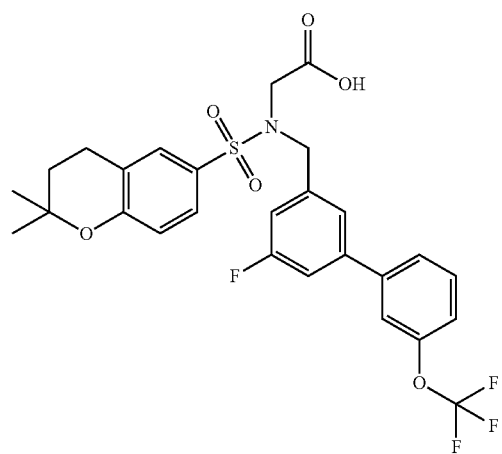 [SMILES: CC1(C)CCc2cc(S(=O)(=O)N(CC(=O)O)Cc3cc(F)cc(-c4cccc(OC(F)(F)F)c4)c3)ccc2O1] | A | |
| 67 | 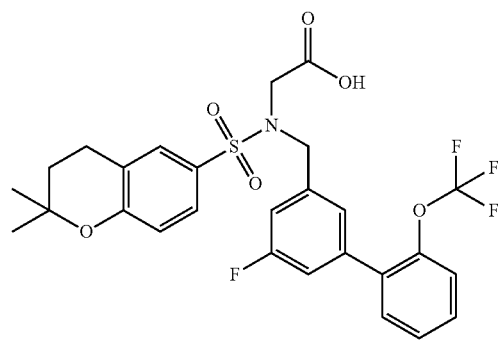 [SMILES: CC1(C)CCc2cc(S(=O)(=O)N(CC(=O)O)Cc3cc(F)cc(-c4ccccc4OC(F)(F)F)c3)ccc2O1] | A | |

TABLE 1-continued

| Example Number | Structure | Data Range* | LE_LG5 86PNP_DR (IC50, uM) |
|---|---|---|---|
| 68 | 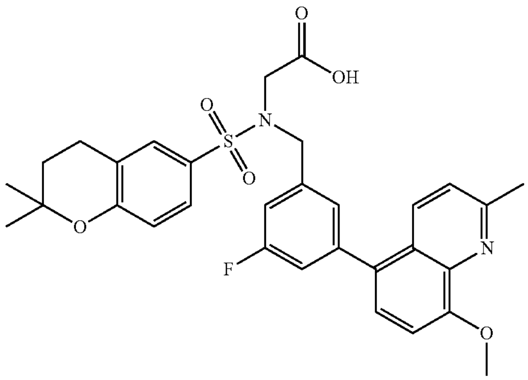 | C | 1.004 |
| 69 | 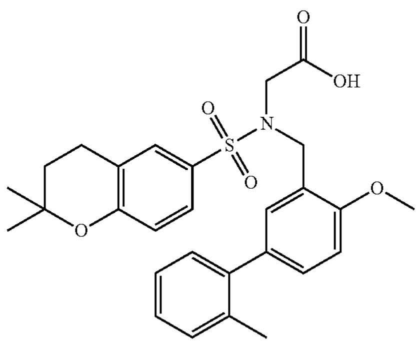 | B | |
| 70 | 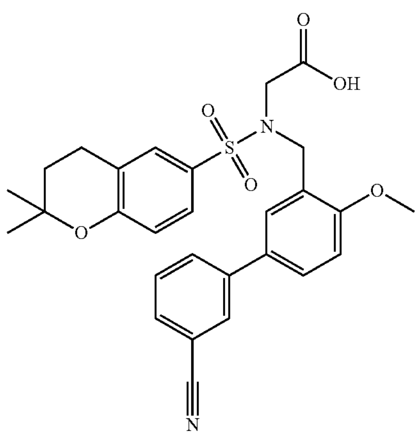 | C | 1.840 |
| 71 | 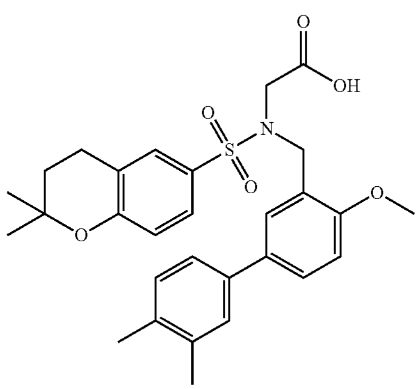 | B | |

TABLE 1-continued

| Example Number | Structure | Data Range* | LE_LG5 86PNP_DR (IC50, uM) |
|---|---|---|---|
| 72 | 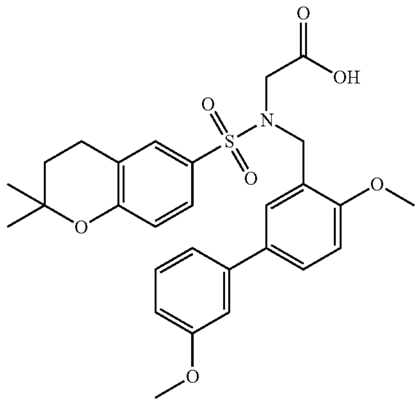 | B | |
| 73 | 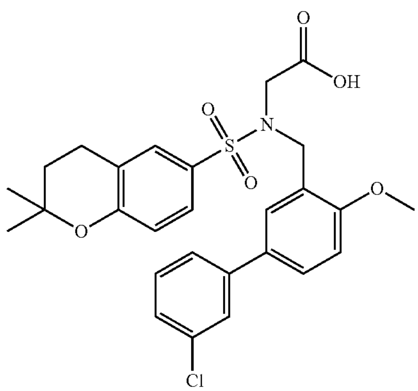 | B | |
| 74 | 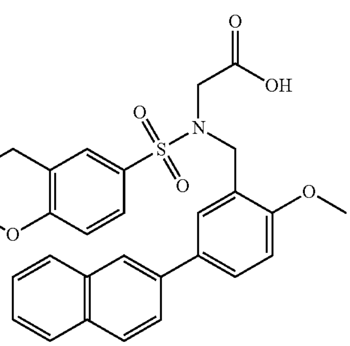 | B | |
| 75 | 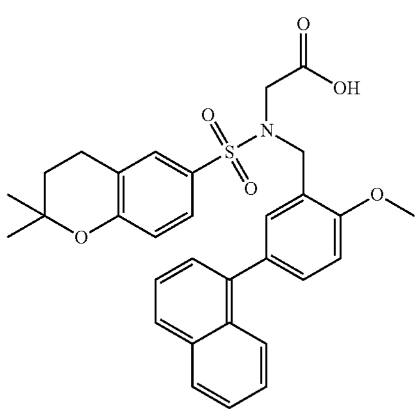 | B | 0.109 |

TABLE 1-continued
| Example Number | Structure | Data Range* | LE_LG5 86PNP_DR (IC50, uM) |
|---|---|---|---|
| 76 | 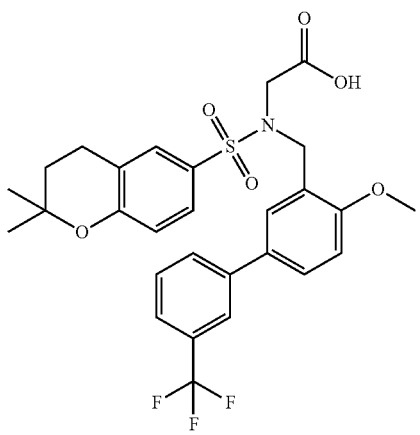 | A | |
| 77 | 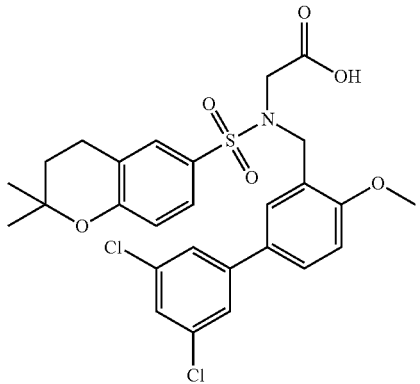 | A | |
| 78 | 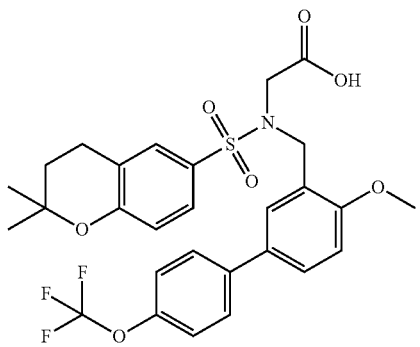 | B | |

TABLE 1-continued

| Example Number | Structure | Data Range* | LE_LG5 86PNP_DR (IC50, uM) |
|---|---|---|---|
| 79 | 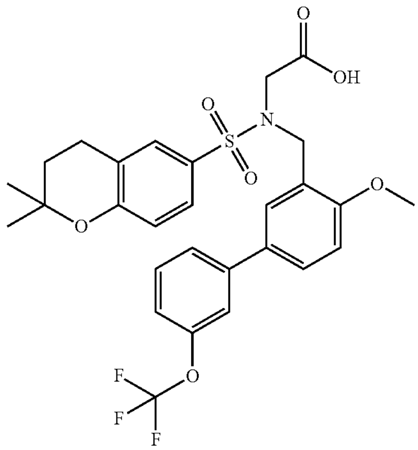 | A | |
| 80 | 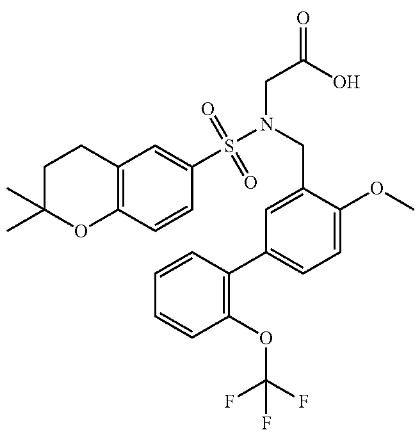 | A | |
| 81 | 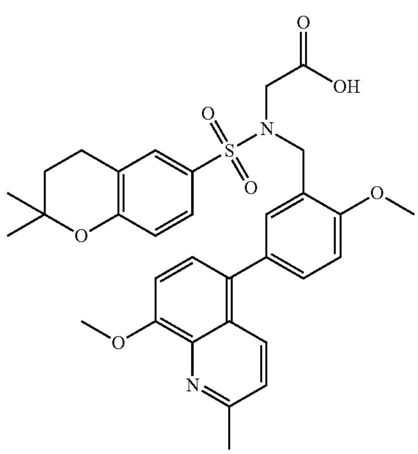 | C | 12.750 |

A = 0.002 – 0.100 μM
B = 0.101 – 1.003 μM
C = ≧1.004 μM

What is claimed is:

1. A compound of Formula (I)

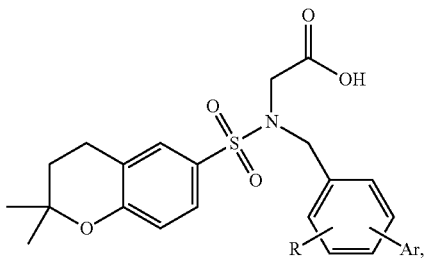

or a pharmaceutically acceptable salt thereof, wherein:
R is selected from hydrogen, cyano, halo, methoxy, and $C_{1-6}$alkyl; and
Ar is selected from phenyl, naphthyl, or quinolinyl, wherein each are substituted with 0, 1, or 2 substituents selected from the group consisting of $C_{1-6}$alkyl, $C_{1-6}$alkoxy, trifluoromethyl, trifluoromethoxy, cyano, and halo.

2. A compound of claim 1, or a pharmaceutically acceptable salt thereof, wherein Ar is phenyl.

3. A compound of claim 2, or a pharmaceutically acceptable salt thereof, wherein R is hydrogen.

4. A compound of claim 2, or a pharmaceutically acceptable salt thereof, wherein R is selected from cyano, halo, and $C_1$ alkyl.

5. A compound of claim 1, or a pharmaceutically acceptable salt thereof, wherein Ar is naphthyl.

6. A compound of claim 5, or a pharmaceutically acceptable salt thereof, wherein R is hydrogen.

7. A compound of claim 5, or a pharmaceutically acceptable salt thereof, wherein R is selected from cyano, halo, and $C_1$ alkyl.

8. A compound of claim 1, or a pharmaceutically acceptable salt thereof, wherein Ar is quinolinyl.

9. A compound of claim 8, or a pharmaceutically acceptable salt thereof, wherein R is hydrogen.

10. A compound of claim 8, or a pharmaceutically acceptable salt thereof, wherein R is selected from cyano, halo, and $C_1$ alkyl.

11. A compound selected from:
2-(N-(biphenyl-3-ylmethyl)-2,2-dimethylchroman-6-sulfonamido)acetic acid;
2-(N-(biphenyl-2-ylmethyl)-2,2-dimethylchroman-6-sulfonamido)acetic acid;
2-(N-(biphenyl-4-ylmethyl)-2,2-dimethylchroman-6-sulfonamido)acetic acid;
2-(2,2-dimethyl-N-((2'-methylbiphenyl-3-yl)methyl)chroman-6-sulfonamido)acetic acid;
2-(N-((3'-cyanobiphenyl-3-yl)methyl)-2,2-dimethylchroman-6-sulfonamido)acetic acid;
2-(N-((3',4'-dimethylbiphenyl-3-yl)methyl)-2,2-dimethylchroman-6-sulfonamido)acetic acid;
2-(N-((3'-methoxybiphenyl-3-yl)methyl)-2,2-dimethylchroman-6-sulfonamido)acetic acid;
2-(N-((3'-chlorobiphenyl-3-yl)methyl)-2,2-dimethylchroman-6-sulfonamido)acetic acid;
2-(2,2-dimethyl-N-(3-(naphthalen-2-yl)benzyl)chroman-6-sulfonamido)acetic acid;
2-(2,2-dimethyl-N-(3-(naphthalen-1-yl)benzyl)chroman-6-sulfonamido)acetic acid;
2-(2,2-dimethyl-N-((3'-(trifluoromethyl)biphenyl-3-yl)methyl)chroman-6-sulfonamido)acetic acid;
2-(N-((3',5'-dichlorobiphenyl-3-yl)methyl)-2,2-dimethylchroman-6-sulfonamido)acetic acid;
2-(2,2-dimethyl-N-((4'-(trifluoromethoxy)biphenyl-3-yl)methyl)chroman-6-sulfonamido)acetic acid;
2-(2,2-dimethyl-N-((3'-(trifluoromethoxy)biphenyl-3-yl)methyl)chroman-6-sulfonamido)acetic acid;
2-(2,2-dimethyl-N-((2'-(trifluoromethoxy)biphenyl-3-yl)methyl)chroman-6-sulfonamido)acetic acid;
2-(N-(3-(8-methoxy-2-methylquinolin-5-yl)benzyl)-2,2-dimethylchroman-6-sulfonamido)acetic acid, TFA;
2-(2,2-dimethyl-N-((2'-methylbiphenyl-4-yl)methyl)chroman-6-sulfonamido)acetic acid;
2-(N-((3'-cyanobiphenyl-4-yl)methyl)-2,2-dimethylchroman-6-sulfonamido)acetic acid;
2-(N-((3',4'-dimethylbiphenyl-4-yl)methyl)-2,2-dimethylchroman-6-sulfonamido)acetic acid;
2-(N-((3'-methoxybiphenyl-4-yl)methyl)-2,2-dimethylchroman-6-sulfonamido)acetic acid;
2-(N-((3'-chlorobiphenyl-4-yl)methyl)-2,2-dimethylchroman-6-sulfonamido)acetic acid;
2-(2,2-dimethyl-N-(4-(naphthalen-2-yl)benzyl)chroman-6-sulfonamido)acetic acid;
2-(2,2-dimethyl-N-(4-(naphthalen-1-yl)benzyl)chroman-6-sulfonamido)acetic acid;
2-(2,2-dimethyl-N-((3'-(trifluoromethyl)biphenyl-4-yl)methyl)chroman-6-sulfonamido)acetic acid;
2-(N-((3',5'-dichlorobiphenyl-4-yl)methyl)-2,2-dimethylchroman-6-sulfonamido)acetic acid;
2-(2,2-dimethyl-N-((4'-(trifluoromethoxy)biphenyl-4-yl)methyl)chroman-6-sulfonamido)acetic acid;
2-(2,2-dimethyl-N-((3'-(trifluoromethoxy)biphenyl-4-yl)methyl)chroman-6-sulfonamido)acetic acid;
2-(2,2-dimethyl-N-((2'-(trifluoromethoxy)biphenyl-4-yl)methyl)chroman-6-sulfonamido)acetic acid;
2-(N-(4-(8-methoxy-2-methylquinolin-5-yl)benzyl)-2,2-dimethylchroman-6-sulfonamido)acetic acid;
2-(N-((5-cyano-2'-methylbiphenyl-3-yl)methyl)-2,2-dimethylchroman-6-sulfonamido)acetic acid;
2-(N-((3',5-dicyanobiphenyl-3-yl)methyl)-2,2-dimethylchroman-6-sulfonamido)acetic acid;
2-(N-((5-cyano-3',4'-dimethylbiphenyl-3-yl)methyl)-2,2-dimethylchroman-6-sulfonamido)acetic acid;
2-(N-((5-cyano-3'-methoxybiphenyl-3-yl)methyl)-2,2-dimethylchroman-6-sulfonamido)acetic acid;
2-(N-((3'-chloro-5-cyanobiphenyl-3-yl)methyl)-2,2-dimethylchroman-6-sulfonamido)acetic acid;
2-(N-(3-cyano-5-(naphthalen-2-yl)benzyl)-2,2-dimethylchroman-6-sulfonamido)acetic acid;
2-(N-(3-cyano-5-(naphthalen-1-yl)benzyl)-2,2-dimethylchroman-6-sulfonamido)acetic acid;
2-(N-((5-cyano-3'-(trifluoromethyl)biphenyl-3-yl)methyl)-2,2-dimethylchroman-6-sulfonamido)acetic acid;
2-(N-((3',5'-dichloro-5-cyanobiphenyl-3-yl)methyl)-2,2-dimethylchroman-6-sulfonamido)acetic acid;

2-(N-((5-cyano-4'-(trifluoromethoxy)biphenyl-3-yl)methyl)-2,2-dimethylchroman-6-sulfonamido)acetic acid;
2-(N-((5-cyano-3'-(trifluoromethoxy)biphenyl-3-yl)methyl)-2,2-dimethylchroman-6-sulfonamido)acetic acid;
2-(N-((5-cyano-2'-(trifluoromethoxy)biphenyl-3-yl)methyl)-2,2-dimethylchroman-6-sulfonamido)acetic acid;
2-(N-(3-cyano-5-(8-methoxy-2-methylquinolin-5-yl)benzyl)-2,2-dimethylchroman-6-sulfonamido)acetic acid;
2-(N-((2,2'-dimethylbiphenyl-4-yl)methyl)-2,2-dimethylchroman-6-sulfonamido)acetic acid;
2-(N-((3'-cyano-2-methylbiphenyl-4-yl)methyl)-2,2-dimethylchroman-6-sulfonamido)acetic acid;
2-(2,2-dimethyl-N-((2,3',4'-trimethylbiphenyl-4-yl)methyl)chroman-6-sulfonamido)acetic acid;
2-(N-((3'-methoxy-2-methylbiphenyl-4-yl)methyl)-2,2-dimethylchroman-6-sulfonamido)acetic acid;
2-(N-((3'-chloro-2-methylbiphenyl-4-yl)methyl)-2,2-dimethylchroman-6-sulfonamido)acetic acid;
2-(2,2-dimethyl-N-(3-methyl-4-(naphthalen-2-yl)benzyl)chroman-6-sulfonamido)acetic acid;
2-(2,2-dimethyl-N-(3-methyl-4-(naphthalen-1-yl)benzyl)chroman-6-sulfonamido)acetic acid;
2-(2,2-dimethyl-N-((2-methyl-3'-(trifluoromethyl)biphenyl-4-yl)methyl)chroman-6-sulfonamido)acetic acid;
2-(N-((3',5'-dichloro-2-methylbiphenyl-4-yl)methyl)-2,2-dimethylchroman-6-sulfonamido)acetic acid;
2-(2,2-dimethyl-N-((2-methyl-4'-(trifluoromethoxy)biphenyl-4-yl)methyl)chroman-6-sulfonamido)acetic acid;
2-(2,2-dimethyl-N-((2-methyl-3'-(trifluoromethoxy)biphenyl-4-yl)methyl)chroman-6-sulfonamido)acetic acid;
2-(2,2-dimethyl-N-((2-methyl-2'-(trifluoromethoxy)biphenyl-4-yl)methyl)chroman-6-sulfonamido)acetic acid;
2-(N-(4-(8-methoxy-2-methylquinolin-5-yl)-3-methylbenzyl)-2,2-dimethylchroman-6-sulfonamido)acetic acid;
2-(N-((5-fluoro-2'-methylbiphenyl-3-yl)methyl)-2,2-dimethylchroman-6-sulfonamido)acetic acid;
2-(N-((3'-cyano-5-fluorobiphenyl-3-yl)methyl)-2,2-dimethylchroman-6-sulfonamido)acetic acid;
2-(N-((5-fluoro-3',4'-dimethylbiphenyl-3-yl)methyl)-2,2-dimethylchroman-6-sulfonamido)acetic acid;
2-(N-((5-fluoro-3'-methoxybiphenyl-3-yl)methyl)-2,2-dimethylchroman-6-sulfonamido)acetic acid;
2-(N-((3'-chloro-5-fluorobiphenyl-3-yl)methyl)-2,2-dimethylchroman-6-sulfonamido)acetic acid;
2-(N-(3-fluoro-5-(naphthalen-2-yl)benzyl)-2,2-dimethylchroman-6-sulfonamido)acetic acid;
2-(N-(3-fluoro-5-(naphthalen-1-yl)benzyl)-2,2-dimethylchroman-6-sulfonamido)acetic acid;
2-(N-((5-fluoro-3'-(trifluoromethyl)biphenyl-3-yl)methyl)-2,2-dimethylchroman-6-sulfonamido)acetic acid;
2-(N-((3',5'-dichloro-5-fluorobiphenyl-3-yl)methyl)-2,2-dimethylchroman-6-sulfonamido)acetic acid;
2-(N-((5-fluoro-4'-(trifluoromethoxy)biphenyl-3-yl)methyl)-2,2-dimethylchroman-6-sulfonamido)acetic acid;
2-(N-((5-fluoro-3'-(trifluoromethoxy)biphenyl-3-yl)methyl)-2,2-dimethylchroman-6-sulfonamido)acetic acid;
2-(N-((5-fluoro-2'-(trifluoromethoxy)biphenyl-3-yl)methyl)-2,2-dimethylchroman-6-sulfonamido)acetic acid;
2-(N-(3-fluoro-5-(8-methoxy-2-methylquinolin-5-yl)benzyl)-2,2-dimethylchroman-6-sulfonamido)acetic acid;
2-(N-((4-methoxy-2'-methylbiphenyl-3-yl)methyl)-2,2-dimethylchroman-6-sulfonamido)acetic acid;
2-(N-((3'-cyano-4-methoxybiphenyl-3-yl)methyl)-2,2-dimethylchroman-6-sulfonamido)acetic acid;
2-(N-((4-methoxy-3',4'-dimethylbiphenyl-3-yl)methyl)-2,2-dimethylchroman-6-sulfonamido)acetic acid;
2-(N-((3',4-dimethoxybiphenyl-3-yl)methyl)-2,2-dimethylchroman-6-sulfonamido)acetic acid;
2-(N-((3'-chloro-4-methoxybiphenyl-3-yl)methyl)-2,2-dimethylchroman-6-sulfonamido)acetic acid;
2-(N-(2-methoxy-5-(naphthalen-2-yl)benzyl)-2,2-dimethylchroman-6-sulfonamido)acetic acid;
2-(N-(2-methoxy-5-(naphthalen-1-yl)benzyl)-2,2-dimethylchroman-6-sulfonamido)acetic acid;
2-(N-((4-methoxy-3'-(trifluoromethyl)biphenyl-3-yl)methyl)-2,2-dimethylchroman-6-sulfonamido)acetic acid;
2-(N-((3',5'-dichloro-4-methoxybiphenyl-3-yl)methyl)-2,2-dimethylchroman-6-sulfonamido)acetic acid;
2-(N-((4-methoxy-4'-(trifluoromethoxy)biphenyl-3-yl)methyl)-2,2-dimethylchroman-6-sulfonamido)acetic acid;
2-(N-((4-methoxy-3'-(trifluoromethoxy)biphenyl-3-yl)methyl)-2,2-dimethylchroman-6-sulfonamido)acetic acid;
2-(N-((4-methoxy-2'-(trifluoromethoxy)biphenyl-3-yl)methyl)-2,2-dimethylchroman-6-sulfonamido)acetic acid; and
2-(N-(2-methoxy-5-(8-methoxy-2-methylquinolin-5-yl)benzyl)-2,2-dimethylchroman-6-sulfonamido)acetic acid;

or a pharmaceutically acceptable salt thereof.

12. A composition comprising a pharmaceutically acceptable amount of a compound of claim 1, or a pharmaceutically acceptable salt thereof, and a pharmaceutically acceptable carrier.

* * * * *